(12) United States Patent
Khairkhahan et al.

(10) Patent No.: US 11,622,759 B2
(45) Date of Patent: Apr. 11, 2023

(54) SYSTEMS AND METHODS FOR ANCHORING AN IMPLANT

(71) Applicant: Polares Medical Inc., Palo Alto, CA (US)

(72) Inventors: Alexander K. Khairkhahan, Palo Alto, CA (US); Michael D. Lesh, Mill Valley, CA (US); Alan R. Klenk, San Jose, CA (US); Craig Mar, Fremont, CA (US); Danielle Tene, Palo Alto, CA (US); Zaya Tun, Livermore, CA (US)

(73) Assignee: Polares Medical Inc., Palo Alto, CA (US)

( * ) Notice: Subject to any disclaimer, the term of this patent is extended or adjusted under 35 U.S.C. 154(b) by 364 days.

(21) Appl. No.: 16/376,500

(22) Filed: Apr. 5, 2019

(65) Prior Publication Data

US 2019/0298332 A1 Oct. 3, 2019

Related U.S. Application Data

(63) Continuation of application No. 14/749,344, filed on Jun. 24, 2015, now Pat. No. 10,251,635.

(Continued)

(51) Int. Cl.
*A61B 17/04* (2006.01)
*A61F 2/24* (2006.01)
*A61B 17/00* (2006.01)

(52) U.S. Cl.
CPC ...... *A61B 17/0401* (2013.01); *A61B 17/0487* (2013.01); *A61F 2/2454* (2013.01); *A61B 2017/00243* (2013.01); *A61B 2017/042* (2013.01); *A61B 2017/0409* (2013.01); *A61B 2017/0412* (2013.01); *A61B 2017/0417* (2013.01); *A61B 2017/0425* (2013.01);
(Continued)

(58) Field of Classification Search
None
See application file for complete search history.

(56) References Cited

U.S. PATENT DOCUMENTS 3,491,376 A 1/1970 Shiley
3,503,079 A 3/1970 Smith
(Continued)

FOREIGN PATENT DOCUMENTS

CN 102256568 12/2002
CN 1984621 6/2007
(Continued)

OTHER PUBLICATIONS

U.S. Appl. No. 16/129,194, filed Sep. 12, 2018, Khairkhahan et al.
(Continued)

*Primary Examiner* — Shaun L David
(74) *Attorney, Agent, or Firm* — Knobbe, Martens, Olson & Bear, LLP

(57) ABSTRACT

The invention relates in some aspects to a device for use in anchoring an implant, including anchors, sutures, implants, clips, tools, lassos, and methods of anchoring among other methods. Anchors as disclosed herein could be utilized to secure a coaptation assistance device, an annuloplasty ring, an artificial valve, cardiac patch, sensor, pacemaker, or other implants. The implant could be a mitral valve ring or artificial mitral valve in some embodiments.

20 Claims, 48 Drawing Sheets

Related U.S. Application Data

(60) Provisional application No. 62/016,582, filed on Jun. 24, 2014.

(52) U.S. Cl.
CPC ............... *A61B 2017/0427* (2013.01); *A61B 2017/0429* (2013.01); *A61B 2017/0437* (2013.01); *A61B 2017/0441* (2013.01); *A61B 2017/0443* (2013.01); *A61B 2017/0464* (2013.01); *A61B 2017/0488* (2013.01); *A61F 2/2445* (2013.01); *A61F 2/2457* (2013.01)

(56) References Cited

U.S. PATENT DOCUMENTS

| | | |
|---|---|---|
| 3,656,185 A | 4/1972 | Carpentier |
| 3,671,979 A | 6/1972 | Moulopoulos |
| 3,874,388 A | 4/1975 | King et al. |
| 3,898,701 A | 8/1975 | La Russa |
| 3,938,197 A | 2/1976 | Milo |
| 4,007,743 A | 2/1977 | Blake |
| 4,011,601 A | 3/1977 | Clune et al. |
| 4,042,979 A | 8/1977 | Angell |
| 4,078,268 A | 3/1978 | Possis |
| 4,204,283 A | 5/1980 | Bellhouse et al. |
| 4,218,783 A | 8/1980 | Reul et al. |
| 4,261,342 A | 4/1981 | Aranguren Duo |
| 4,263,680 A | 4/1981 | Ruel et al. |
| 4,275,469 A | 6/1981 | Gabbay |
| RE31,040 E | 9/1982 | Possis |
| 4,352,211 A | 10/1982 | Parravicini |
| 4,488,318 A | 12/1984 | Kaster |
| 4,490,859 A | 1/1985 | Black et al. |
| 4,491,986 A | 1/1985 | Gabbay |
| 4,561,129 A | 12/1985 | Arpesella |
| 4,687,483 A | 8/1987 | Fisher et al. |
| 4,705,516 A | 11/1987 | Barone et al. |
| 4,759,758 A | 7/1988 | Gabbay |
| 4,790,843 A | 12/1988 | Carpentier et al. |
| 4,960,424 A | 10/1990 | Grooters |
| 4,994,077 A | 2/1991 | Dobben |
| 5,002,567 A | 3/1991 | Bona et al. |
| 5,078,737 A | 1/1992 | Bona et al. |
| 5,131,905 A | 7/1992 | Grooters |
| 5,197,980 A | 3/1993 | Gorshkov et al. |
| 5,217,484 A | 6/1993 | Marks |
| 5,258,023 A | 11/1993 | Reger |
| 5,332,402 A | 7/1994 | Teitelbaum |
| 5,344,442 A | 9/1994 | Deac |
| 5,370,662 A * | 12/1994 | Stone ............... A61B 17/0401 606/232 |
| 5,397,347 A | 3/1995 | Cuilleron et al. |
| 5,397,348 A | 3/1995 | Campbell et al. |
| 5,413,599 A | 5/1995 | Imachi et al. |
| 5,487,760 A | 1/1996 | Villafana |
| 5,500,015 A | 3/1996 | Deac |
| 5,522,886 A | 6/1996 | Milo |
| 5,554,186 A | 9/1996 | Guo et al. |
| 5,582,616 A | 12/1996 | Bolduc et al. |
| 5,593,435 A | 1/1997 | Carpentier et al. |
| 5,626,613 A * | 5/1997 | Schmieding ....... A61B 17/0401 24/711.3 |
| 5,658,313 A | 8/1997 | Thal |
| 5,662,683 A * | 9/1997 | Kay .................. A61B 17/0401 606/232 |
| 5,662,704 A | 9/1997 | Gross |
| 5,716,370 A | 2/1998 | Williamson, IV et al. |
| 5,733,331 A | 3/1998 | Peredo |
| 5,824,065 A | 10/1998 | Gross |
| 5,824,066 A | 10/1998 | Gross |
| 5,824,067 A | 10/1998 | Gross |
| 5,855,601 A | 1/1999 | Bessler et al. |
| 5,888,240 A | 3/1999 | Carpentier et al. |
| 5,957,949 A | 9/1999 | Leonhardt et al. |
| 6,007,577 A | 12/1999 | Vanney et al. |
| 6,024,096 A | 2/2000 | Buckberg |
| 6,042,607 A | 3/2000 | Williamson, IV et al. |
| 6,045,497 A | 4/2000 | Schweich et al. |
| 6,045,573 A * | 4/2000 | Wenstrom, Jr. .... A61B 17/0401 606/232 |
| 6,063,114 A | 5/2000 | Nash et al. |
| 6,066,160 A | 5/2000 | Colvin et al. |
| 6,086,612 A | 7/2000 | Jansen |
| 6,113,631 A | 9/2000 | Jansen |
| 6,162,233 A | 12/2000 | Williamson, IV et al. |
| 6,217,610 B1 | 4/2001 | Carpentier et al. |
| 6,221,104 B1 | 4/2001 | Buckberg et al. |
| 6,250,308 B1 | 6/2001 | Cox |
| 6,264,602 B1 | 7/2001 | Mortier et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,312,447 B1 | 11/2001 | Grimes |
| 6,312,464 B1 | 11/2001 | Navia |
| 6,332,893 B1 | 12/2001 | Mortier et al. |
| 6,358,277 B1 | 3/2002 | Duran |
| 6,383,147 B1 | 5/2002 | Stobie |
| 6,391,053 B1 | 5/2002 | Brendzel et al. |
| 6,391,054 B2 | 5/2002 | Carpentier et al. |
| 6,402,679 B1 | 6/2002 | Mortier et al. |
| 6,402,780 B2 | 6/2002 | Williamson, IV et al. |
| 6,409,758 B2 | 6/2002 | Stobie et al. |
| 6,419,695 B1 | 7/2002 | Gabbay |
| 6,439,237 B1 | 8/2002 | Buckberg et al. |
| 6,450,171 B1 | 9/2002 | Buckberg et al. |
| 6,451,024 B1 * | 9/2002 | Thompson .......... A61B 17/0401 606/104 |
| 6,454,799 B1 | 9/2002 | Schreck |
| 6,458,153 B1 | 10/2002 | Bailey et al. |
| 6,482,228 B1 | 11/2002 | Norred |
| 6,540,782 B1 | 4/2003 | Snyders |
| 6,544,167 B2 | 4/2003 | Buckberg et al. |
| 6,565,603 B2 | 5/2003 | Cox |
| 6,569,198 B1 | 5/2003 | Wilson |
| 6,602,288 B1 | 8/2003 | Cosgrove et al. |
| 6,602,289 B1 | 8/2003 | Colvin et al. |
| 6,626,930 B1 | 9/2003 | Allen et al. |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,682,559 B2 | 1/2004 | Myers et al. |
| 6,702,852 B2 | 3/2004 | Stobie et al. |
| 6,719,790 B2 | 4/2004 | Brendzel et al. |
| 6,752,813 B2 | 6/2004 | Goldfarb et al. |
| 6,764,510 B2 | 7/2004 | Vidlund et al. |
| 6,780,200 B2 | 8/2004 | Jansen |
| 6,790,237 B2 | 9/2004 | Stinson |
| 6,797,002 B2 | 9/2004 | Spence et al. |
| 6,800,090 B2 | 10/2004 | Alferness et al. |
| 6,805,710 B2 | 10/2004 | Bolling et al. |
| 6,821,297 B2 | 11/2004 | Snyders |
| 6,837,247 B2 | 1/2005 | Buckberg et al. |
| 6,840,246 B2 | 1/2005 | Downing |
| 6,846,324 B2 | 1/2005 | Stobie |
| 6,869,444 B2 | 3/2005 | Gabbay |
| 6,908,478 B2 | 6/2005 | Alferness et al. |
| 6,911,043 B2 | 6/2005 | Myers et al. |
| 6,926,730 B1 | 8/2005 | Nguyen et al. |
| 6,966,925 B2 | 11/2005 | Stobie |
| 6,991,649 B2 | 1/2006 | Sievers |
| 6,997,950 B2 | 2/2006 | Chawla |
| 7,018,408 B2 | 3/2006 | Bailey et al. |
| 7,037,333 B2 | 5/2006 | Myers et al. |
| 7,048,754 B2 | 5/2006 | Martin et al. |
| 7,056,280 B2 | 6/2006 | Buckberg et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,087,064 B1 | 8/2006 | Hyde |
| 7,112,207 B2 | 9/2006 | Allen et al. |
| 7,122,043 B2 | 10/2006 | Greenhalgh et al. |
| 7,160,322 B2 | 1/2007 | Gabbay |

(56) References Cited

U.S. PATENT DOCUMENTS

| | | |
|---|---|---|
| 7,166,126 B2 | 1/2007 | Spence et al. |
| 7,175,656 B2 | 2/2007 | Khairkhahan |
| 7,195,641 B2 | 3/2007 | Palmaz et al. |
| 7,217,284 B2 | 5/2007 | Houser et al. |
| 7,226,467 B2 | 6/2007 | Lucatero et al. |
| 7,275,546 B2 | 10/2007 | Buckberg et al. |
| 7,291,168 B2 | 11/2007 | Macoviak et al. |
| 7,294,148 B2 | 11/2007 | McCarthy |
| 7,296,577 B2 | 11/2007 | Taylor et al. |
| 7,316,706 B2 | 1/2008 | Bloom et al. |
| 7,320,704 B2 | 1/2008 | Lashinski et al. |
| 7,335,213 B1 | 2/2008 | Hyde et al. |
| 7,338,520 B2 | 3/2008 | Bailey et al. |
| 7,341,584 B1 | 3/2008 | Starkey |
| 7,357,814 B2 | 4/2008 | Gabbay |
| 7,374,572 B2 | 5/2008 | Gabbay |
| RE40,377 E | 6/2008 | Williamson, IV et al. |
| 7,381,220 B2 | 6/2008 | Macoviak et al. |
| 7,396,364 B2 | 7/2008 | Moaddeb et al. |
| 7,404,824 B1 | 7/2008 | Webler et al. |
| 7,435,257 B2 | 10/2008 | Lashinski et al. |
| 7,445,630 B2 | 11/2008 | Lashinski et al. |
| 7,455,689 B2 | 11/2008 | Johnson |
| 7,485,143 B2 | 2/2009 | Webler et al. |
| 7,510,573 B2 | 3/2009 | Gabbay |
| 7,510,576 B2 | 3/2009 | Langberg et al. |
| 7,527,646 B2 | 5/2009 | Rahdert et al. |
| 7,527,647 B2 | 5/2009 | Spence |
| 7,530,998 B1 | 5/2009 | Starkey |
| 7,534,259 B2 | 5/2009 | Lashinski et al. |
| 7,556,645 B2 | 7/2009 | Lashinski et al. |
| 7,559,936 B2 | 7/2009 | Levine |
| 7,563,267 B2 | 7/2009 | Goldfarb et al. |
| 7,563,273 B2 | 7/2009 | Goldfarb et al. |
| 7,591,847 B2 | 9/2009 | Navia et al. |
| 7,608,091 B2 | 10/2009 | Goldfarb et al. |
| 7,611,534 B2 | 11/2009 | Kapadia et al. |
| 7,621,948 B2 | 11/2009 | Herrmann et al. |
| 7,648,532 B2 | 1/2010 | Greenhalgh et al. |
| 7,655,015 B2 | 2/2010 | Goldfarb et al. |
| 7,658,762 B2 | 2/2010 | Lashinski et al. |
| 7,658,763 B2 | 2/2010 | Stobie |
| 7,666,224 B2 | 2/2010 | Vidlund et al. |
| 7,674,286 B2 | 3/2010 | Alfieri et al. |
| 7,678,145 B2 | 3/2010 | Vidlund et al. |
| 7,682,391 B2 | 3/2010 | Johnson |
| 7,691,144 B2 | 4/2010 | Chang et al. |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,736,388 B2 | 6/2010 | Goldfarb et al. |
| 7,740,638 B2 | 6/2010 | Hyde |
| 7,744,609 B2 | 6/2010 | Allen et al. |
| 7,753,923 B2 | 7/2010 | St. Goar et al. |
| 7,758,491 B2 | 7/2010 | Buckner et al. |
| 7,758,595 B2 | 7/2010 | Allen et al. |
| 7,776,084 B2 | 8/2010 | Johnson |
| 7,785,366 B2 | 8/2010 | Maurer et al. |
| 7,799,038 B2 | 9/2010 | Sogard et al. |
| 7,803,187 B2 | 9/2010 | Hauser |
| 7,819,915 B2 | 10/2010 | Stobie et al. |
| 7,846,203 B2 | 12/2010 | Cribier |
| 7,887,552 B2 | 2/2011 | Bachman |
| 7,901,454 B2 | 3/2011 | Kapadia et al. |
| 7,909,866 B2 | 3/2011 | Stobie |
| 7,914,576 B2 | 3/2011 | Navia et al. |
| 7,927,370 B2 | 4/2011 | Webler et al. |
| 7,935,144 B2 | 5/2011 | Robin et al. |
| 7,935,145 B2 | 5/2011 | Alfieri et al. |
| 7,938,827 B2 | 5/2011 | Hauck et al. |
| 7,942,928 B2 | 5/2011 | Webler et al. |
| 7,951,195 B2 | 5/2011 | Antonsson et al. |
| 7,951,196 B2 | 5/2011 | McCarthy |
| 7,955,385 B2 | 6/2011 | Crittenden |
| 7,959,673 B2 | 6/2011 | Carpentier et al. |
| 7,981,139 B2 | 7/2011 | Martin et al. |
| 7,988,725 B2 | 8/2011 | Gross et al. |
| 7,993,396 B2 | 8/2011 | McCarthy |
| 7,998,151 B2 | 8/2011 | St. Goar et al. |
| 8,012,201 B2 | 9/2011 | Lashinski et al. |
| 8,012,202 B2 | 9/2011 | Alameddine |
| 8,016,882 B2 | 9/2011 | Macoviak et al. |
| 8,029,518 B2 | 10/2011 | Goldfarb et al. |
| 8,052,751 B2 | 11/2011 | Aklog et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,092,525 B2 | 1/2012 | Eliasen et al. |
| 8,118,866 B2 | 2/2012 | Herrmann et al. |
| 8,128,691 B2 | 3/2012 | Keranen |
| 8,133,272 B2 | 3/2012 | Hyde |
| 8,142,494 B2 | 3/2012 | Rahdert et al. |
| 8,142,495 B2 | 3/2012 | Hasenkam et al. |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,207 B2 | 5/2012 | Machold et al. |
| 8,187,299 B2 | 5/2012 | Goldfarb et al. |
| 8,187,323 B2 | 5/2012 | Mortier et al. |
| 8,204,605 B2 | 6/2012 | Hastings et al. |
| 8,206,439 B2 | 6/2012 | Gomez Duran |
| 8,216,230 B2 | 7/2012 | Hauck et al. |
| 8,216,256 B2 | 7/2012 | Raschdorf, Jr. et al. |
| 8,216,302 B2 | 7/2012 | Wilson et al. |
| 8,216,303 B2 | 7/2012 | Navia |
| 8,221,493 B2 | 7/2012 | Boyle et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano et al. |
| 8,252,051 B2 | 8/2012 | Chau et al. |
| 8,262,725 B2 | 9/2012 | Subramanian |
| 8,277,502 B2 | 10/2012 | Miller et al. |
| 8,287,591 B2 | 10/2012 | Keidar et al. |
| 8,292,884 B2 | 10/2012 | Levine et al. |
| 8,308,796 B2 | 11/2012 | Lashinski et al. |
| 8,323,336 B2 | 12/2012 | Hill et al. |
| 8,337,390 B2 | 12/2012 | Ferrazzi |
| 8,353,956 B2 | 1/2013 | Miller et al. |
| 8,361,086 B2 | 1/2013 | Allen et al. |
| 8,377,118 B2 | 2/2013 | Lashinski et al. |
| 8,382,796 B2 | 2/2013 | Blaeser et al. |
| 8,382,828 B2 | 2/2013 | Roberts |
| 8,382,829 B1 | 2/2013 | Call et al. |
| RE44,075 E | 3/2013 | Williamson, IV et al. |
| 8,398,708 B2 | 3/2013 | Meiri et al. |
| 8,408,214 B2 | 4/2013 | Spenser |
| 8,413,573 B2 | 4/2013 | Rebecchi |
| 8,414,644 B2 | 4/2013 | Quadri et al. |
| 8,449,606 B2 | 5/2013 | Eliasen et al. |
| 8,454,683 B2 | 6/2013 | Rafiee et al. |
| 8,470,028 B2 | 6/2013 | Thornton et al. |
| 8,500,800 B2 | 8/2013 | Maisano et al. |
| 8,506,624 B2 | 8/2013 | Vidlund et al. |
| 8,523,881 B2 | 9/2013 | Cabiri et al. |
| 8,545,553 B2 | 10/2013 | Zipory et al. |
| 8,608,797 B2 | 12/2013 | Gross et al. |
| 8,657,872 B2 | 2/2014 | Seguin |
| 8,690,939 B2 | 4/2014 | Miller et al. |
| 8,715,342 B2 | 5/2014 | Zipory et al. |
| 8,734,467 B2 | 5/2014 | Miller et al. |
| 8,784,483 B2 | 7/2014 | Navia |
| 8,790,394 B2 | 7/2014 | Miller et al. |
| 8,795,352 B2 | 8/2014 | O'beirne et al. |
| 8,808,368 B2 | 8/2014 | Maisano et al. |
| 8,845,717 B2 | 9/2014 | Khairkhahan et al. |
| 8,858,623 B2 | 10/2014 | Miller et al. |
| 8,888,843 B2 | 11/2014 | Khairkhahan et al. |
| 8,888,844 B2 | 11/2014 | Eliasen et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |

(56) References Cited

U.S. PATENT DOCUMENTS

| | | | |
|---|---|---|---|
| 8,940,042 B2 | 1/2015 | Miller et al. | |
| 8,940,044 B2 | 1/2015 | Hammer et al. | |
| 9,005,279 B2 | 4/2015 | Gabbay | |
| 9,011,520 B2 | 4/2015 | Miller et al. | |
| 9,011,530 B2 | 4/2015 | Reich et al. | |
| 9,056,006 B2 | 6/2015 | Edelman et al. | |
| 9,119,719 B2 | 9/2015 | Zipory et al. | |
| 9,180,007 B2 | 11/2015 | Reich et al. | |
| 9,192,472 B2 | 11/2015 | Gross et al. | |
| 9,204,964 B2 | 12/2015 | Dahlgren et al. | |
| 9,232,999 B2 | 1/2016 | Maurer et al. | |
| 9,265,608 B2 | 2/2016 | Miller et al. | |
| 9,277,994 B2 | 3/2016 | Miller et al. | |
| 9,351,830 B2 | 5/2016 | Gross et al. | |
| 9,414,921 B2 | 8/2016 | Miller et al. | |
| 9,452,048 B2 | 9/2016 | O'beirne et al. | |
| 9,474,606 B2 | 10/2016 | Zipory et al. | |
| 9,526,613 B2 | 12/2016 | Gross et al. | |
| 9,549,817 B2 | 1/2017 | Rafiee | |
| 9,554,906 B2 | 1/2017 | Aklog et al. | |
| 9,561,104 B2 | 2/2017 | Miller et al. | |
| 9,592,118 B2 | 3/2017 | Khairkhahan et al. | |
| 9,592,121 B1 | 3/2017 | Khairkhahan | |
| 9,592,122 B2 | 3/2017 | Zipory et al. | |
| 9,610,162 B2 | 4/2017 | Zipory et al. | |
| 9,610,163 B2 | 4/2017 | Khairkhahan et al. | |
| 9,622,861 B2 | 4/2017 | Miller et al. | |
| 9,636,224 B2 | 5/2017 | Zipory et al. | |
| 9,662,209 B2 | 5/2017 | Gross et al. | |
| 9,713,530 B2 | 7/2017 | Cabiri et al. | |
| 9,724,192 B2 | 8/2017 | Sheps et al. | |
| 9,730,793 B2 | 8/2017 | Reich et al. | |
| 9,775,709 B2 | 10/2017 | Miller et al. | |
| 9,814,572 B2 | 11/2017 | Edelman et al. | |
| 9,872,769 B2 | 1/2018 | Gross et al. | |
| 9,883,943 B2 | 2/2018 | Gross et al. | |
| 9,918,840 B2 | 3/2018 | Reich et al. | |
| 9,937,042 B2 | 4/2018 | Cabiri et al. | |
| 9,949,828 B2 | 4/2018 | Sheps et al. | |
| 9,968,452 B2 | 5/2018 | Sheps et al. | |
| 9,968,454 B2 | 5/2018 | Reich et al. | |
| 9,974,653 B2 | 5/2018 | Gross et al. | |
| 10,028,832 B2 | 7/2018 | Quill et al. | |
| 10,098,737 B2 | 10/2018 | Miller et al. | |
| 10,123,874 B2 | 11/2018 | Khairkhahan et al. | |
| 10,130,472 B2 | 11/2018 | O'beirne et al. | |
| 10,166,098 B2 | 1/2019 | Khairkhahan et al. | |
| 10,195,030 B2 | 2/2019 | Gross et al. | |
| 10,226,342 B2 | 3/2019 | Kutzik et al. | |
| 10,251,635 B2 | 4/2019 | Khairkhahan et al. | |
| 10,265,170 B2 | 4/2019 | Zipory et al. | |
| 10,299,793 B2 | 5/2019 | Zipory et al. | |
| 10,350,068 B2 | 7/2019 | Miller et al. | |
| 10,357,366 B2 | 7/2019 | Gross et al. | |
| 10,363,136 B2 | 7/2019 | Miller et al. | |
| 10,363,137 B2 | 7/2019 | Gross et al. | |
| 10,368,982 B2 | 8/2019 | Weber et al. | |
| 10,376,266 B2 | 8/2019 | Herman et al. | |
| 10,376,365 B2 | 8/2019 | Khairkhahan et al. | |
| 10,383,726 B2 | 8/2019 | Kramer | |
| 10,433,955 B2 | 10/2019 | Edelman et al. | |
| 10,449,046 B2 | 10/2019 | Rafiee | |
| 10,449,333 B2 | 10/2019 | Hammer et al. | |
| 10,470,882 B2 | 11/2019 | Gross et al. | |
| 10,470,883 B2 | 11/2019 | Khairkhahan et al. | |
| 10,478,303 B2 | 11/2019 | Khairkhahan et al. | |
| 10,492,909 B2 | 12/2019 | Miller et al. | |
| 10,500,048 B2 | 12/2019 | Khairkhahan et al. | |
| 10,512,542 B2 | 12/2019 | Khairkhahan et al. | |
| 10,517,719 B2 | 12/2019 | Miller et al. | |
| 10,543,088 B2 | 1/2020 | Lashinski | |
| 10,548,729 B2 | 2/2020 | Zipory et al. | |
| 10,548,731 B2 | 2/2020 | Lashinski et al. | |
| 10,561,498 B2 | 2/2020 | Gross et al. | |
| 10,568,738 B2 | 2/2020 | Sheps et al. | |
| 10,610,360 B2 | 4/2020 | Reich et al. | |
| 10,653,524 B2 | 5/2020 | Khairkhahan et al. | |
| 10,702,386 B2 | 7/2020 | Khairkhahan et al. | |
| 10,751,180 B2 | 8/2020 | Schewel | |
| 11,000,372 B2 | 5/2021 | Khairkhahan et al. | |
| 11,160,656 B2 | 11/2021 | Khairkhahan | |
| 2001/0007956 A1 | 7/2001 | Letac et al. | |
| 2001/0021872 A1 | 9/2001 | Bailey et al. | |
| 2002/0029080 A1 | 3/2002 | Mortier et al. | |
| 2002/0058995 A1 | 5/2002 | Stevens | |
| 2002/0116024 A1 | 8/2002 | Goldberg et al. | |
| 2002/0138135 A1 | 9/2002 | Duerig | |
| 2002/0188301 A1 | 12/2002 | Dallara et al. | |
| 2003/0023248 A1 | 1/2003 | Parodi | |
| 2003/0100943 A1 | 5/2003 | Bolduc | |
| 2003/0105474 A1 | 6/2003 | Bonutti | |
| 2003/0135263 A1 | 7/2003 | Rourke et al. | |
| 2003/0191497 A1 | 10/2003 | Cope | |
| 2003/0199975 A1 | 10/2003 | Gabbay | |
| 2004/0082956 A1* | 4/2004 | Baldwin | A61B 17/0401 606/232 |
| 2004/0088047 A1 | 5/2004 | Spence et al. | |
| 2004/0143323 A1 | 7/2004 | Chawla | |
| 2004/0172046 A1 | 9/2004 | Hlavka et al. | |
| 2004/0193217 A1* | 9/2004 | Lubbers | A61B 17/0401 606/232 |
| 2004/0210307 A1 | 10/2004 | Khairkhahan | |
| 2005/0004665 A1 | 1/2005 | Aklog | |
| 2005/0004668 A1 | 1/2005 | Aklog et al. | |
| 2005/0010287 A1 | 1/2005 | Macoviak et al. | |
| 2005/0075727 A1 | 4/2005 | Wheatley et al. | |
| 2005/0096740 A1 | 5/2005 | Langberg et al. | |
| 2005/0107871 A1 | 5/2005 | Realyvasquez | |
| 2005/0159810 A1 | 7/2005 | Filsoufi | |
| 2005/0177180 A1* | 8/2005 | Kaganov | A61B 17/068 606/151 |
| 2005/0228495 A1 | 10/2005 | Macoviak | |
| 2005/0261708 A1 | 11/2005 | Pasricha et al. | |
| 2005/0283232 A1 | 12/2005 | Gabbay | |
| 2006/0058871 A1 | 3/2006 | Zakay et al. | |
| 2006/0122608 A1* | 6/2006 | Fallin | A61F 2/0811 606/232 |
| 2006/0149368 A1 | 7/2006 | Spence | |
| 2006/0190030 A1 | 8/2006 | To et al. | |
| 2006/0252984 A1 | 11/2006 | Rahdert et al. | |
| 2007/0005069 A1* | 1/2007 | Contiliano | A61B 17/0401 606/304 |
| 2007/0049970 A1 | 3/2007 | Belef et al. | |
| 2007/0093890 A1 | 4/2007 | Eliasen et al. | |
| 2007/0112352 A1* | 5/2007 | Sorensen | A61B 17/1739 606/326 |
| 2007/0112425 A1 | 5/2007 | Schaller et al. | |
| 2007/0118151 A1 | 5/2007 | Davidson | |
| 2007/0129758 A1 | 6/2007 | Saadat | |
| 2007/0185571 A1 | 8/2007 | Kapadia et al. | |
| 2007/0233239 A1 | 10/2007 | Navia et al. | |
| 2007/0239272 A1 | 10/2007 | Navia et al. | |
| 2007/0244554 A1 | 10/2007 | Rafiee et al. | |
| 2007/0244555 A1 | 10/2007 | Rafiee et al. | |
| 2007/0244556 A1 | 10/2007 | Rafiee et al. | |
| 2007/0250160 A1 | 10/2007 | Rafiee | |
| 2007/0255399 A1 | 11/2007 | Eliasen et al. | |
| 2007/0265658 A1 | 11/2007 | Nelson et al. | |
| 2007/0265700 A1 | 11/2007 | Eliasen et al. | |
| 2007/0265702 A1 | 11/2007 | Lattouf | |
| 2007/0293943 A1 | 12/2007 | Quinn | |
| 2008/0065204 A1 | 3/2008 | Macoviak et al. | |
| 2008/0109075 A1 | 5/2008 | Keramen | |
| 2008/0125860 A1 | 5/2008 | Webler et al. | |
| 2008/0125861 A1 | 5/2008 | Webler et al. | |
| 2008/0195205 A1 | 8/2008 | Schwartz | |
| 2008/0262609 A1 | 10/2008 | Gross et al. | |
| 2008/0319541 A1 | 12/2008 | Filsoufi | |
| 2009/0012354 A1 | 1/2009 | Wood | |
| 2009/0088836 A1 | 4/2009 | Bishop et al. | |
| 2009/0177277 A1 | 7/2009 | Milo | |
| 2009/0234404 A1 | 9/2009 | Fitzgerald et al. | |
| 2009/0259304 A1 | 10/2009 | O'Beirne et al. | |
| 2009/0259307 A1 | 10/2009 | Gross et al. | |

(56) References Cited

U.S. PATENT DOCUMENTS

| | | |
|---|---|---|
| 2009/0287304 A1 | 11/2009 | Dahlgren et al. |
| 2009/0326648 A1 | 12/2009 | Machold et al. |
| 2010/0069954 A1 | 3/2010 | Blaeser et al. |
| 2010/0121435 A1 | 5/2010 | Subramanian et al. |
| 2010/0131057 A1 | 5/2010 | Subramanian et al. |
| 2010/0161043 A1 | 6/2010 | Maisano et al. |
| 2010/0161047 A1 | 6/2010 | Cabiri et al. |
| 2010/0249947 A1 | 9/2010 | Lesh et al. |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer |
| 2010/0280606 A1 | 11/2010 | Naor |
| 2010/0286767 A1 | 11/2010 | Zipory et al. |
| 2010/0298929 A1 | 11/2010 | Thornton et al. |
| 2010/0312333 A1 | 12/2010 | Navia et al. |
| 2011/0004299 A1 | 1/2011 | Navia et al. |
| 2011/0082538 A1 | 4/2011 | Dahlgren et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0224785 A1 | 9/2011 | Hacohen |
| 2011/0288635 A1 | 11/2011 | Miller et al. |
| 2011/0301698 A1 | 12/2011 | Miller et al. |
| 2012/0016468 A1 | 1/2012 | Robin et al. |
| 2012/0022557 A1 | 1/2012 | Cabiri et al. |
| 2012/0022644 A1 | 1/2012 | Reich et al. |
| 2012/0078360 A1 | 3/2012 | Rafiee |
| 2012/0136436 A1 | 5/2012 | Cabiri et al. |
| 2012/0165930 A1 | 6/2012 | Gifford et al. |
| 2012/0197388 A1 | 8/2012 | Khairkhahan et al. |
| 2012/0203336 A1 | 8/2012 | Annest |
| 2012/0283757 A1 | 11/2012 | Miller et al. |
| 2012/0323316 A1 | 12/2012 | Chau et al. |
| 2012/0330410 A1 | 12/2012 | Hammer et al. |
| 2012/0330411 A1 | 12/2012 | Gross et al. |
| 2013/0023985 A1 | 1/2013 | Khairkhahan et al. |
| 2013/0096672 A1 | 4/2013 | Reich et al. |
| 2013/0116776 A1 | 5/2013 | Gross et al. |
| 2013/0116780 A1 | 5/2013 | Miller et al. |
| 2013/0131792 A1 | 5/2013 | Miller et al. |
| 2013/0190861 A1 | 7/2013 | Chau et al. |
| 2013/0190866 A1 | 7/2013 | Zipory et al. |
| 2013/0238024 A1 | 9/2013 | Taylor et al. |
| 2013/0282028 A1 | 10/2013 | Conklin et al. |
| 2013/0338763 A1 | 12/2013 | Rowe et al. |
| 2014/0018906 A1 | 1/2014 | Rafiee |
| 2014/0025163 A1 | 1/2014 | Padala et al. |
| 2014/0039615 A1 | 2/2014 | Padala et al. |
| 2014/0067048 A1 | 3/2014 | Chau |
| 2014/0094903 A1 | 4/2014 | Miller et al. |
| 2014/0128965 A1 | 5/2014 | Rafiee |
| 2014/0142695 A1 | 5/2014 | Gross et al. |
| 2014/0148898 A1 | 5/2014 | Gross et al. |
| 2014/0222137 A1 | 8/2014 | Miller et al. |
| 2014/0243963 A1 | 8/2014 | Sheps et al. |
| 2014/0276648 A1 | 9/2014 | Hammer et al. |
| 2014/0277088 A1 | 9/2014 | Friedman |
| 2014/0309661 A1 | 10/2014 | Sheps et al. |
| 2014/0343668 A1 | 11/2014 | Zipory et al. |
| 2014/0358223 A1 | 12/2014 | Rafiee et al. |
| 2014/0379075 A1 | 12/2014 | Maurer et al. |
| 2015/0012087 A1 | 1/2015 | Miller et al. |
| 2015/0039083 A1 | 2/2015 | Rafiee et al. |
| 2015/0057682 A1 | 2/2015 | Kovach |
| 2015/0081014 A1 | 3/2015 | Gross et al. |
| 2015/0100116 A1 | 4/2015 | Mohl et al. |
| 2015/0105855 A1 | 4/2015 | Cabiri et al. |
| 2015/0112429 A1 | 4/2015 | Khairkhahan et al. |
| 2015/0112432 A1 | 4/2015 | Reich et al. |
| 2015/0119981 A1 | 4/2015 | Khairkhahan et al. |
| 2015/0164637 A1 | 6/2015 | Khairkhahan et al. |
| 2015/0182336 A1 | 7/2015 | Zipory et al. |
| 2015/0202043 A1 | 7/2015 | Zakai et al. |
| 2015/0230924 A1 | 8/2015 | Miller et al. |
| 2015/0257877 A1 | 9/2015 | Hernandez |
| 2015/0272586 A1 | 10/2015 | Herman et al. |
| 2015/0272734 A1 | 10/2015 | Sheps et al. |
| 2015/0297212 A1 | 10/2015 | Reich et al. |
| 2015/0366556 A1 | 12/2015 | Khairkhahan et al. |
| 2015/0366666 A1 | 12/2015 | Khairkhahan et al. |
| 2016/0008132 A1 | 1/2016 | Cabiri et al. |
| 2016/0030176 A1 | 2/2016 | Mohl et al. |
| 2016/0058557 A1 | 3/2016 | Reich et al. |
| 2016/0074164 A1 | 3/2016 | Naor |
| 2016/0089233 A1 | 3/2016 | Lee et al. |
| 2016/0106437 A1 | 4/2016 | van der Burg et al. |
| 2016/0113767 A1 | 4/2016 | Miller et al. |
| 2016/0157862 A1 | 6/2016 | Hernandez et al. |
| 2016/0158008 A1 | 6/2016 | Miller et al. |
| 2016/0262755 A1 | 9/2016 | Zipory et al. |
| 2016/0324639 A1 | 11/2016 | Nguyen et al. |
| 2016/0331523 A1 | 11/2016 | Chau et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0100249 A1 | 4/2017 | Miller et al. |
| 2017/0105839 A1 | 4/2017 | Subramanian et al. |
| 2017/0135815 A1 | 5/2017 | Gross et al. |
| 2017/0135816 A1 | 5/2017 | Lashinski et al. |
| 2017/0189186 A1 | 7/2017 | Mohl |
| 2017/0196691 A1 | 7/2017 | Zipory et al. |
| 2017/0209270 A1 | 7/2017 | Miller et al. |
| 2017/0245993 A1 | 8/2017 | Gross et al. |
| 2017/0245994 A1 | 8/2017 | Khairkhahan et al. |
| 2017/0258588 A1 | 9/2017 | Zipory et al. |
| 2017/0258590 A1 | 9/2017 | Khairkhahan et al. |
| 2017/0265995 A1 | 9/2017 | Khairkhahan et al. |
| 2017/0296340 A1 | 10/2017 | Gross et al. |
| 2017/0325958 A1 | 11/2017 | Reich et al. |
| 2017/0325959 A1 | 11/2017 | Sheps et al. |
| 2017/0354500 A1 | 12/2017 | Martinez et al. |
| 2017/0367825 A1 | 12/2017 | Cabiri et al. |
| 2018/0008409 A1 | 1/2018 | Kutzik et al. |
| 2018/0014933 A1 | 1/2018 | Miller et al. |
| 2018/0014934 A1 | 1/2018 | Miller et al. |
| 2018/0049875 A1 | 2/2018 | Iflah et al. |
| 2018/0116797 A9 | 5/2018 | Miller et al. |
| 2018/0125657 A1 | 5/2018 | Dahlgren et al. |
| 2018/0228608 A1 | 8/2018 | Sheps et al. |
| 2018/0250133 A1 | 9/2018 | Reich et al. |
| 2018/0256318 A1 | 9/2018 | Khairkhahan |
| 2018/0256333 A1 | 9/2018 | Cabiri et al. |
| 2018/0256334 A1 | 9/2018 | Sheps et al. |
| 2018/0263776 A1 | 9/2018 | Gross et al. |
| 2018/0263777 A1 | 9/2018 | Gross et al. |
| 2018/0318080 A1 | 11/2018 | Quill et al. |
| 2018/0325670 A1 | 11/2018 | De Canniere |
| 2019/0008641 A1 | 1/2019 | Dahlgren et al. |
| 2019/0046318 A1 | 2/2019 | Miller et al. |
| 2019/0070004 A1 | 3/2019 | Iflah et al. |
| 2019/0076247 A1 | 3/2019 | Zeng |
| 2019/0076249 A1 | 3/2019 | Khairkhahan |
| 2019/0125325 A1 | 5/2019 | Sheps et al. |
| 2019/0133586 A1 | 5/2019 | Zipory et al. |
| 2019/0151090 A1 | 5/2019 | Gross et al. |
| 2019/0151093 A1 | 5/2019 | Keidar et al. |
| 2019/0159898 A1 | 5/2019 | Kutzik et al. |
| 2019/0167425 A1 | 6/2019 | Reich et al. |
| 2019/0175344 A1 | 6/2019 | Khairkhahan |
| 2019/0183644 A1 | 6/2019 | Hacohen |
| 2019/0201191 A1 | 7/2019 | McLean et al. |
| 2019/0216600 A1 | 7/2019 | Zipory et al. |
| 2019/0254821 A1 | 8/2019 | Rafiee et al. |
| 2019/0269512 A9 | 9/2019 | Lashinski |
| 2019/0269513 A9 | 9/2019 | Cabiri et al. |
| 2019/0274830 A1 | 9/2019 | Miller et al. |
| 2019/0282358 A1 | 9/2019 | Khairkhahan et al. |
| 2019/0282364 A1 | 9/2019 | Khairkhahan et al. |
| 2019/0298332 A1 | 10/2019 | Khairkhahan et al. |
| 2019/0298522 A1 | 10/2019 | Subramanian et al. |
| 2019/0321049 A1 | 10/2019 | Herman et al. |
| 2019/0336288 A1 | 11/2019 | Gross et al. |

(56) References Cited

U.S. PATENT DOCUMENTS

| | | |
|---|---|---|
| 2019/0336289 A1 | 11/2019 | Miller et al. |
| 2019/0350703 A1 | 11/2019 | Weber et al. |
| 2019/0350705 A1 | 11/2019 | Schewel et al. |
| 2019/0374343 A1 | 12/2019 | Lashinski et al. |
| 2019/0374750 A1 | 12/2019 | Hammer et al. |
| 2019/0380834 A1 | 12/2019 | Rafiee |
| 2020/0015971 A1 | 1/2020 | Brauon et al. |
| 2020/0030097 A1 | 1/2020 | Khairkhahan et al. |
| 2020/0038186 A1 | 2/2020 | Gross et al. |
| 2020/0100899 A1 | 4/2020 | Miller et al. |
| 2020/0113685 A1 | 4/2020 | Miller et al. |
| 2020/0214841 A1 | 7/2020 | Khairkhahan et al. |
| 2020/0222185 A1 | 7/2020 | Kappetein et al. |
| 2020/0275974 A1 | 9/2020 | Gifford et al. |
| 2020/0289265 A1 | 9/2020 | Gifford et al. |
| 2020/0330229 A1 | 10/2020 | Serraf et al. |
| 2020/0337843 A1 | 10/2020 | Khairkhahan et al. |
| 2020/0383776 A1 | 12/2020 | Schewel |
| 2020/0397567 A1 | 12/2020 | Khairkhahan et al. |
| 2021/0085462 A1 | 3/2021 | Gifford et al. |
| 2021/0196462 A1 | 7/2021 | Khairkhahan |
| 2021/0298901 A1 | 9/2021 | Khairkhahan et al. |
| 2022/0000621 A1 | 1/2022 | Gifford et al. |
| 2022/0039944 A1 | 2/2022 | Khairkhahan |
| 2022/0039951 A1 | 2/2022 | Khairkhahan |
| 2022/0054269 A1 | 2/2022 | Khairkhahan |
| 2022/0079753 A1 | 3/2022 | Zimmerman et al. |
| 2022/0079755 A1 | 3/2022 | Zimmerman et al. |
| 2022/0096236 A1 | 3/2022 | Guidotti et al. |
| 2022/0160499 A1 | 5/2022 | Miyashiro et al. |
| 2022/0160508 A1 | 5/2022 | Miyashiro et al. |
| 2022/0192822 A1 | 6/2022 | McLean et al. |
| 2022/0125579 A1 | 7/2022 | McLean et al. |

FOREIGN PATENT DOCUMENTS

| | | |
|---|---|---|
| CN | 101056596 | 10/2007 |
| CN | 101068508 | 11/2007 |
| CN | 101947146 | 1/2011 |
| CN | 102065777 | 5/2011 |
| CN | 102458309 | 5/2012 |
| CN | 202821715 | 3/2013 |
| CN | 10338726 | 10/2013 |
| CN | 102905648 | 1/2015 |
| CN | 104394803 | 3/2015 |
| CN | 104582637 | 4/2015 |
| CN | 105451688 | 3/2016 |
| EP | 1 294 310 | 3/2003 |
| EP | 1 959 865 | 8/2008 |
| EP | 2 410 948 | 2/2012 |
| EP | 1 796 597 | 1/2013 |
| EP | 2 661 239 | 11/2013 |
| EP | 2 667 824 | 12/2013 |
| EP | 2 995 279 | 3/2016 |
| JP | S54-088693 | 7/1979 |
| JP | 2005-535384 | 11/2005 |
| JP | 2007-518492 | 7/2007 |
| JP | 2008-517672 | 5/2008 |
| JP | 2010-511469 | 4/2010 |
| JP | 2012-511402 | 5/2012 |
| JP | 2012-520716 | 9/2012 |
| JP | 2014-510563 | 5/2014 |
| JP | 2014-231015 | 12/2014 |
| JP | 2015-523898 | 8/2016 |
| JP | 2016-533798 | 11/2016 |
| JP | 2017-18675 | 1/2017 |
| WO | WO 1997/007744 | 3/1997 |
| WO | WO 99/53869 | 10/1998 |
| WO | WO 2004/014258 | 2/2004 |
| WO | WO 2005/069875 | 8/2005 |
| WO | WO 2006/032051 | 3/2006 |
| WO | WO 2006/041877 | 4/2006 |
| WO | WO 2006/086434 | 8/2006 |
| WO | WO 2007/062054 | 5/2007 |
| WO | WO 2007/135101 | 11/2007 |
| WO | WO 2007/140470 | 12/2007 |
| WO | WO 2008/068756 | 6/2008 |
| WO | WO 2008/141322 | 11/2008 |
| WO | WO 2010/106438 | 9/2010 |
| WO | WO 2011/037891 | 3/2011 |
| WO | WO 2011/047168 | 4/2011 |
| WO | WO 2012/061809 | 5/2012 |
| WO | WO 2012/092437 | 7/2012 |
| WO | WO 2012/102928 | 8/2012 |
| WO | WO 2013/131069 | 9/2013 |
| WO | WO 2013/173587 | 11/2013 |
| WO | WO 2013/178335 | 12/2013 |
| WO | WO 2013/192107 | 12/2013 |
| WO | WO 2014/181336 | 11/2014 |
| WO | WO 2014/207575 | 12/2014 |
| WO | WO 2015/020971 | 2/2015 |
| WO | WO 2015/052570 | 4/2015 |
| WO | WO 2015/061533 | 4/2015 |
| WO | WO 2015/195823 | 12/2015 |
| WO | WO 2015/200497 | 12/2015 |
| WO | WO 2016/178136 | 11/2016 |
| WO | WO 2016/183485 | 11/2016 |
| WO | WO 2017/079279 | 5/2017 |
| WO | WO 2017/136596 | 8/2017 |
| WO | WO 2018/169878 | 9/2018 |
| WO | WO 2019/116322 | 6/2019 |
| WO | WO 2019/222694 | 11/2019 |
| WO | WO 2019/241777 | 12/2019 |
| WO | WO 2020/055811 | 3/2020 |

OTHER PUBLICATIONS

U.S. Appl. No. 16/185,419, filed Nov. 9, 2018, Khairkhahan et al.
U.S. Appl. No. 16/220,322, filed Dec. 14, 2018, Khairkhahan et al.
U.S. Appl. No. 16/275,665, filed Feb. 14, 2019, Khairkhahan.
U.S. Appl. No. 16/376,500, filed Apr. 5, 2019, Khairkhahan et al.
Biocina et al., *Mitral Valve Repair With The New Mitrofast® Repair System*, Dubrava University Hospital, Zagreb, Crotia, Mitrofast Abstract European Soc CVS 55$^{th}$ Congress—May 11-14, 2006 Suppl 1 to vol. 5.
Biocina, *The arteficial coaptation surface concept in mitral valve repair*, University of Zagreb School of Medicine, Department of Cardiac Surgery, Savudrija Mitrofast 2010.
Chiam et al., *Percutaneous Transcatheter Mitral Valve Repair*, The American College of Cardiology Foundation, JACC: Cardiovascular Interventions, vol. 4 No. 1, Jan. 2011:1-13.
Jassar et al., *Posterior Leaflet Augmentation in Ischemic Mitral Regurgitation Increases Leaflet Coaptation and Mobility*, The Society of Thoracic Surgeons, Ann Thorac Surg 2012; 94:1438-45.
Langer et al., *Posterior mitral leaflet extension: An adjunctive repair option for ischemic mitral regurgitation?*, Surgery for Acquired Cardiovascular Disease, The Journal of Thoracic and Cardiovascular Surgery, Apr. 2006, downloaded Jun. 18, 2011.
Mohl et al., *An Innovative Concept For Transcatheter Treatment of Annular Dilatation and Restrictive Leaflet Motion in Mitral Insufficiency*, Medical University of Vienna, 1 page.
Mohl et al., *The Angel Valve Concept*, Vienna University of Technology, Medical University of Vienna, Technology Offer, 1 page.
Piemonte et al., *Cardiovascular™: The Mitral Valve Spacer*, Presented at Transcatheter Cardiovascular Therapeutics Conference—TCT Conference, Oct. 2008.
Rumel et al, *The Correction of Mitral Insufficiency with a Trans-Valvular Polyvinyl Formalinized Plastic (Ivalon) Sponge Prosthesis: A Preliminary Report*, American College of Chest Physicians, 1958;33;401-413, Dec. 2, 2010.
Extended European Search Report, EP 12738989.8, dated May 24, 2016.
Extended European Search Report, EP 13806272.4, dated Nov. 11, 2015.
Extended European Search Report, EP 15809346.8, dated Feb. 13, 2018.
Extended European Search Report, EP 14856738.1, dated Jun. 7, 2017.
Extended European Search Report, EP 15812032.9, dated Oct. 18, 2017.

(56) References Cited

OTHER PUBLICATIONS

International Preliminary Report on Patentability for PCT/US2012/021744 dated Aug. 8, 2013 in 15 pages.
International Search Report for Application No. PCT/US2013/046173 dated Oct. 4, 2013 in 15 pages.
International Search Report for Application No. PCT/US2014/061901 dated Jan. 26, 2015 in 14 pages.
International Search Report for Application No. PCT/US2015/036260 dated Oct. 1, 2015 in 20 pages.
International Search Report for Application No. PCT/US2015/037451 dated Oct. 6, 2015 in 12 pages.
International Search Report for Application No. PCT/US2016/060094 dated Nov. 2, 2016 in 8 pages.
Office Action for CA 2,825,520 dated Aug. 21, 2018.
Office Action for CA 2,877,344 dated Mar. 12, 2019.
Office Action for CN 201280006673.7 dated Dec. 10, 2014.
Office Action for CN 201280006673.7 dated Sep. 22, 2015.
Office Action for CN 201280006673.7 dated Feb. 1, 2016.
Office Action for CN 201380044122.4 dated Nov. 4, 2015.
Office Action for CN 201380044122.4 dated Aug. 24, 2016.
Office Action for JP 2013-552015 dated Dec. 7, 2015.
Office Action for JP 2013-552015 dated Oct. 7, 2016.
Office Action for JP 2013-552015 dated Jun. 5, 2017.
Office Action for JP 2015-518499 dated Feb. 27, 2017.
Office Action for JP 2015-518499 dated Aug. 31, 2017.
Office Action for JP 2015-518499 dated Aug. 20, 2018.
Office Action for EP 12738989.8 dated Mar. 3, 2017.
Office Action for EP 12738989.8 dated Sep. 19, 2017.
Office Action for CA 2,825,520 dated Nov. 27, 2017.
Office Action for CN 201480070933.6 dated May 10, 2017.
Office Action for CN 201480070933.6 dated Aug. 10, 2018.
Office Action for CN 201480070933.6 dated Dec. 25, 2017.
Office Action for JP 2016-525999 dated Jul. 9, 2018.
Office Action for CN 201580044329.0 dated Jan. 17, 2018.
Office Action for CN 201580045375.2 dated Mar. 29, 2018.
Office Action for CN 201580045375.2 dated Nov. 12, 2018.
International Search Report for Application No. PCT/US2018/022043 dated Jun. 25, 2018 in 13 pages.
Extended European Search Report, EP 16862864.2, dated May 10, 2019.
Office Action for JP 2016-574967 dated May 7, 2019.
U.S. Appl. No. 16/675,565, filed Nov. 6, 2019, Khairkhahan et al.
U.S. Appl. No. 16/685,338, filed Nov. 15, 2019, Khairkhahan.
U.S. Appl. No. 16/705,605, filed Dec. 6, 2019, Khairkhahan et al.
International Search Report for Application No. PCT/US2016/060094 dated Feb. 9, 2017 in 8 pages.
Office Action for CA 2,877,344 dated Oct. 9, 2019.
Office Action for CN 201480070933.6 dated Apr. 17, 2019.
Office Action for CN 201580044329.0 dated Jul. 29, 2019.
Office Action for CN 201680077877.8 dated Aug. 15, 2019.
Office Action for EP 15812032.9, dated Oct. 10, 2019.
Office Action for JP 2016-525999 dated Jun. 27, 2019.
Office Action for JP 2016-525999 dated Mar. 16, 2020.
Office Action for 2016-573983 dated Apr. 1, 2019.
Office Action for 2016-573983 dated Nov. 11, 2019.
Office Action for JP 2016-574967 dated Dec. 26, 2019.
International Search Report for Application No. PCT/US2019/050331 dated Jan. 23, 2020 in 9 pages.
Office Action for CA 2,877,344 dated Jul. 21, 2020.
Office Action for CN 201580044329.0 dated Mar. 3, 2020.
Office Action for 2016-573983 dated May 11, 2020.
Office Action for CN 201580044329.0 dated Aug. 26, 2020.
Office Action for EP 15812032.9, dated Jul. 6, 2020.
Office Action for JP 2016-574967 dated Jun. 29, 2020.
Office Action for JP 2018-543021 dated Oct. 27, 2020.
Office Action for CA 2,877,344 dated Dec. 23, 2020.
Office Action for CA 2,934,182 dated Dec. 9, 2020.
Office Action for JP 2020-082001 dated Mar. 29, 2021.
Extended European Search Report, EP 18768736.3, dated Oct. 9, 2020.
International Search Report for Application No. PCT/US2020/065261 dated Apr. 13, 2021 in 13 pages.
Office Action for CN 201880031519.2 dated May 19, 2021.
Office Action for EP 13806272.4, dated Mar. 23, 2021.
Office Action for EP 14856738.1, dated Apr. 23, 2021.
Office Action for JP 2020-085273 dated May 31, 2021.
Office Action for CA 2,934,182 dated Jun. 30, 2021.
Office Action for CA 2,958,065 dated Jul. 9, 2021.
Office Action for JP 2018-543021 dated Oct. 4, 2021.
Office Action for JP 2020-085273 dated Aug. 23, 2021.
Office Action for JP 2020-082001 dated Nov. 29, 2021.
Office Action for CA 2,934,182 dated Mar. 2, 2022.
Office Action for CA 2,958,065 dated Mar. 2, 2022.
Office Action for 2020-041944 dated Feb. 21, 2022.
Office Action for 2019-572351 dated Feb. 28, 2022.
International Search Report for Application No. PCT/US2021/016248 dated Mar. 29, 2022 in 15 pages.
Extended European Search Report, EP 19860754.1 dated Jun. 1, 2022.
International Search Report for Application No. PCT/US2022/071235 dated Jun. 27, 2022 in 13 pages.
Office Action for 2020-041944 dated Jul. 22, 2022.

* cited by examiner

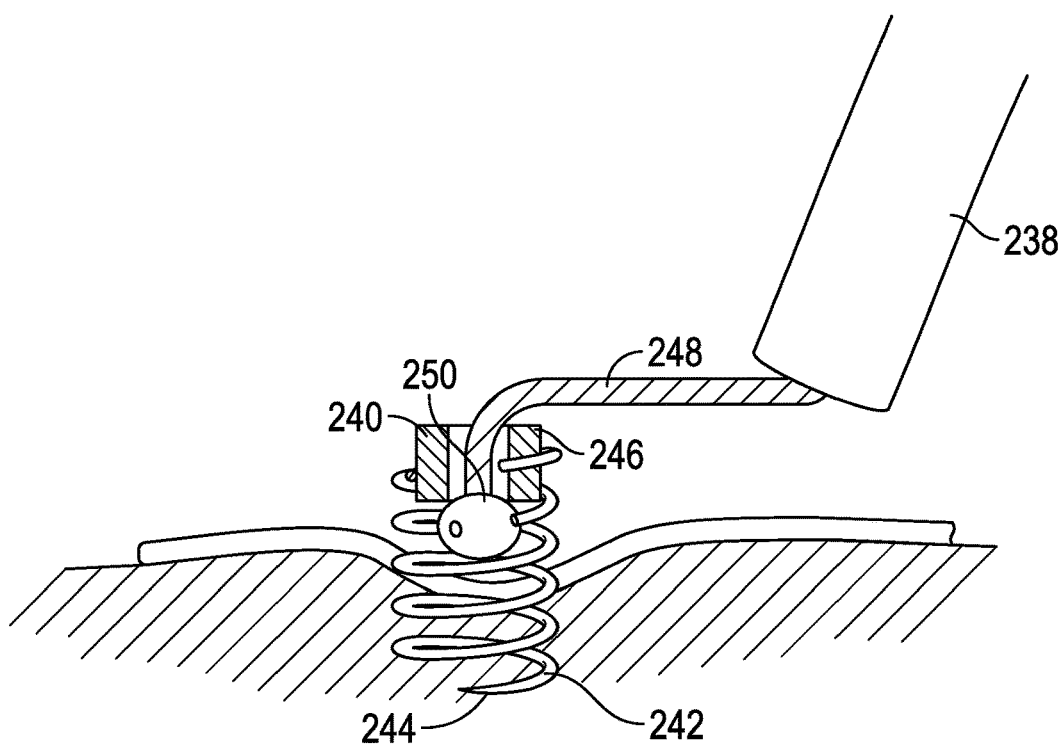
FIG. 7
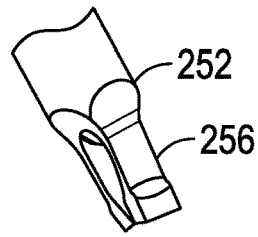
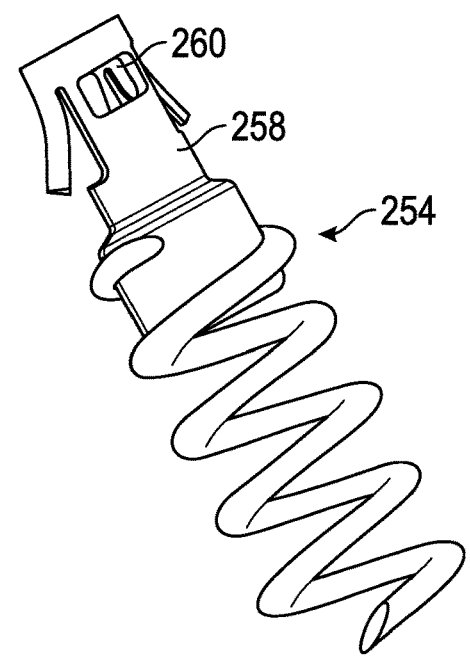
FIG. 8

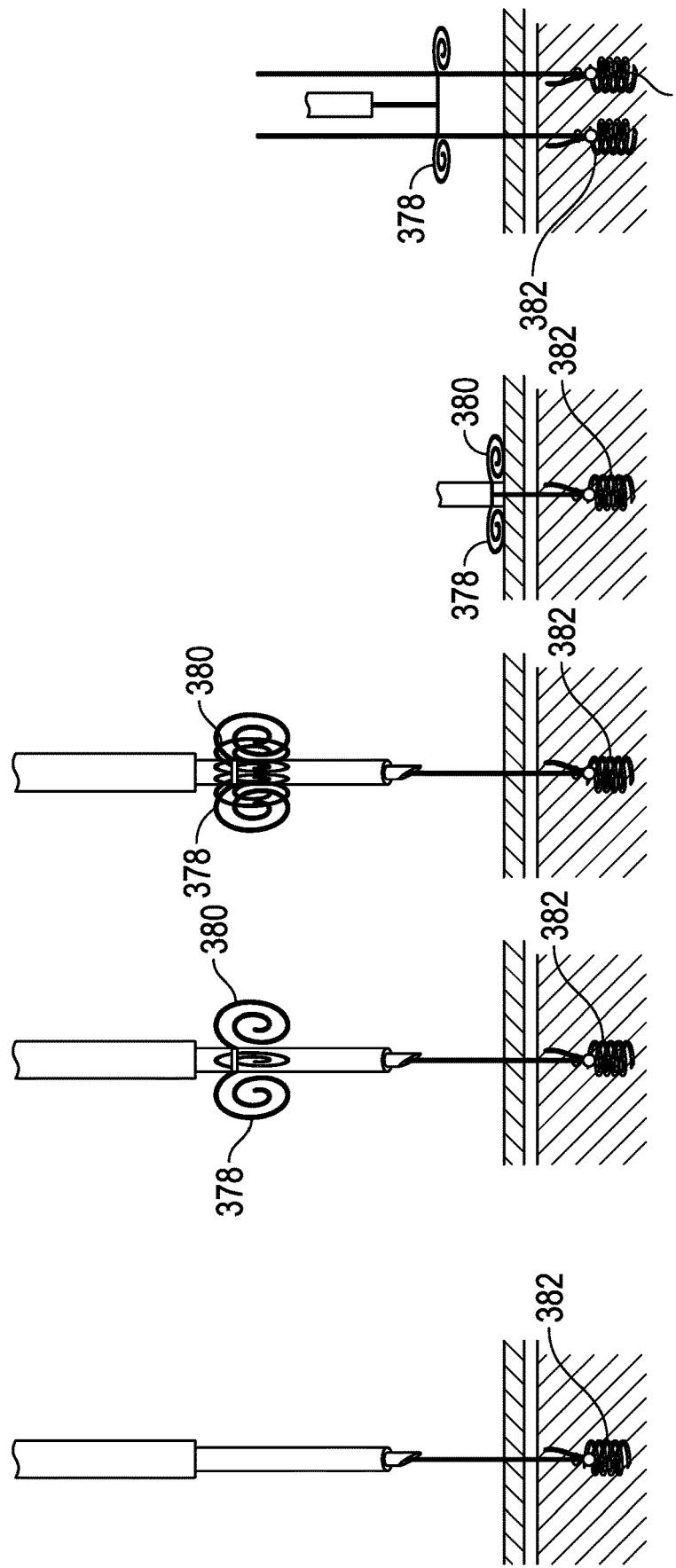

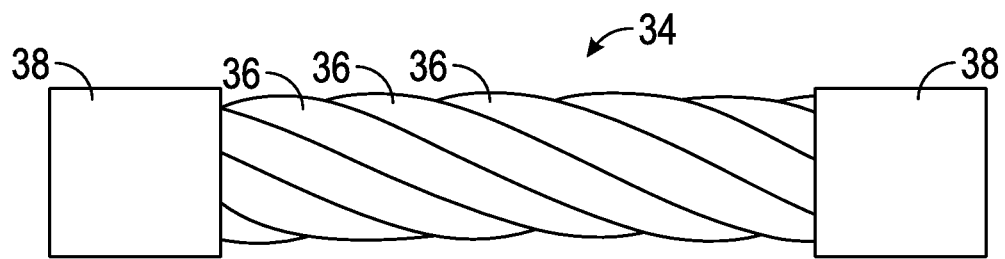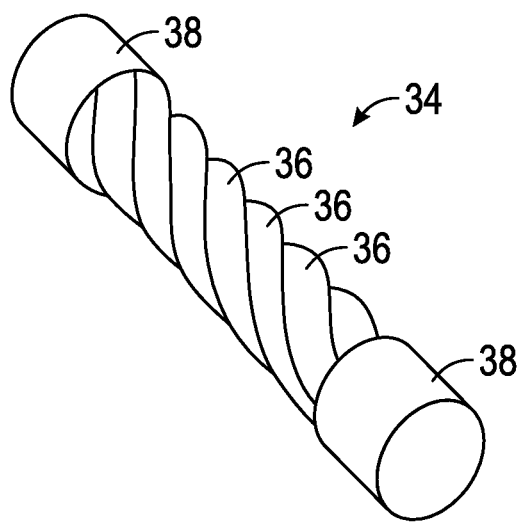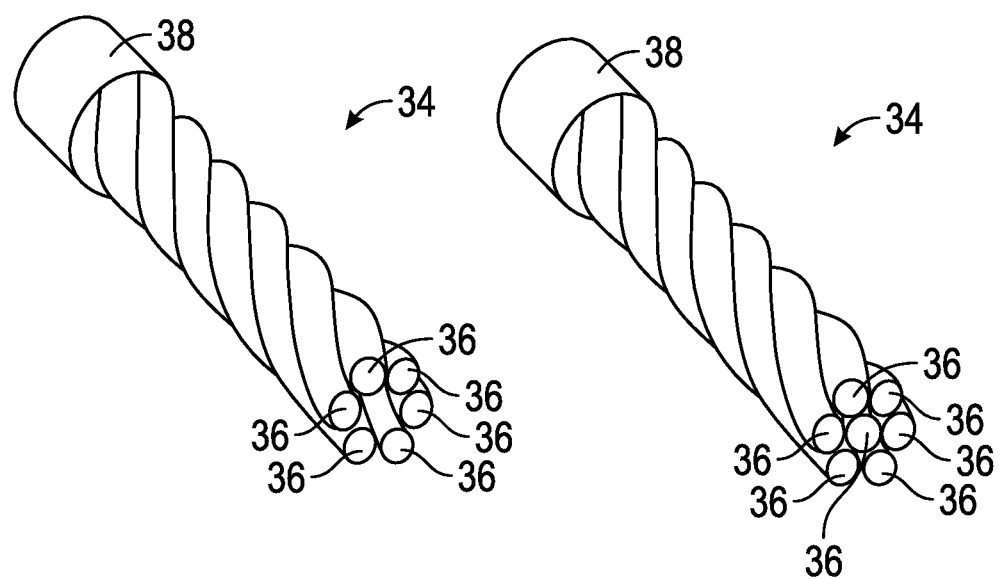
FIG. 32

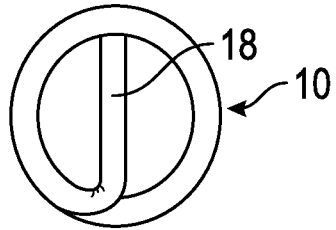
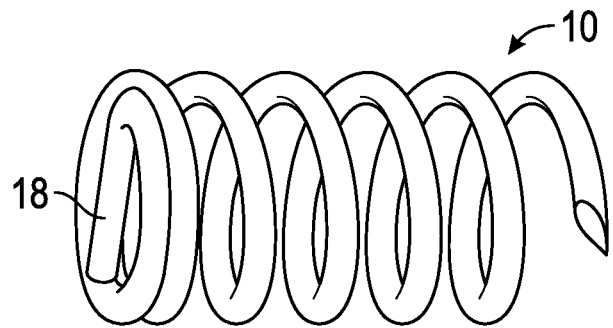
FIG. 43A  FIG. 43B
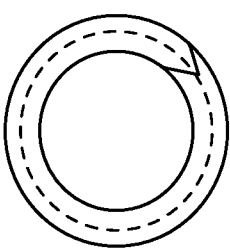 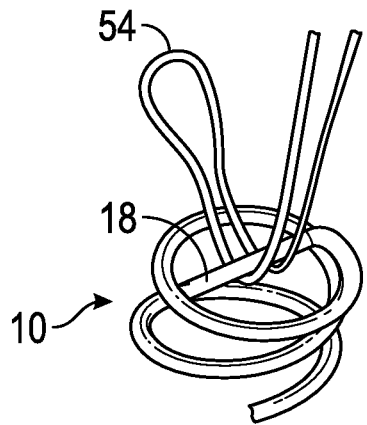 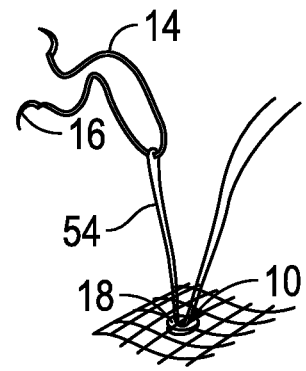
FIG. 43C  FIG. 43D  FIG. 43E
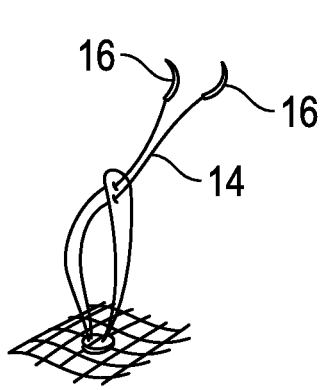 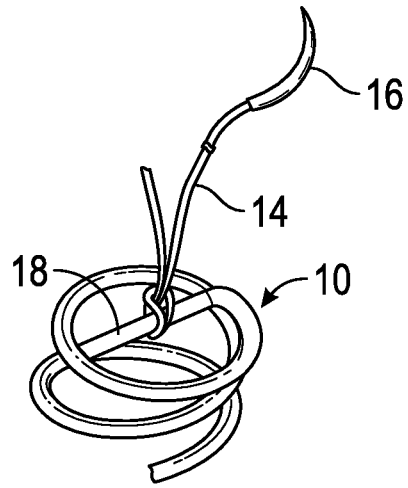
FIG. 43F  FIG. 43G

SYSTEMS AND METHODS FOR ANCHORING AN IMPLANT

This application is a continuation of U.S. application Ser. No. 14/749,344, filed Jun. 24, 2015, which claims priority under 35 U.S.C. § 119(e) as a nonprovisional of U.S. Prov. Patent Application No. 62/016,582, titled "Systems and Methods for Anchoring a Cardiac Implant" and filed Jun. 24, 2014. The entire disclosure of the foregoing priority applications are hereby incorporated by reference herein for all purposes.

This application is related to U.S. patent application Ser. No. 14/742,199, titled "Mitral Valve Implants for the Treatment of Valvular Regurgitation" and filed Jun. 17, 2015. The entire disclosure of the foregoing application is hereby incorporated by reference herein for all purposes.

BACKGROUND

Field

The present invention generally provides, in some embodiments, improved medical devices, systems, and methods, typically for treatment of heart valve disease and/or for altering characteristics of one or more valves of the body. Embodiments of the invention include implants for treatment of mitral valve regurgitation.

The human heart receives blood from the organs and tissues via the veins, pumps that blood through the lungs where the blood becomes enriched with oxygen, and propels the oxygenated blood out of the heart to the arteries so that the organ systems of the body can extract the oxygen for proper function. Deoxygenated blood flows back to the heart where it is once again pumped to the lungs.

The heart includes four chambers: the right atrium (RA), the right ventricle (RV), the left atrium (LA) and the left ventricle (LV). The pumping action of the left and right sides of the heart occurs generally in synchrony during the overall cardiac cycle.

The heart has four valves generally configured to selectively transmit blood flow in the correct direction during the cardiac cycle. The valves that separate the atria from the ventricles are referred to as the atrioventricular (or AV) valves. The AV valve between the left atrium and the left ventricle is the mitral valve. The AV valve between the right atrium and the right ventricle is the tricuspid valve. The pulmonary valve directs blood flow to the pulmonary artery and thence to the lungs; blood returns to the left atrium via the pulmonary veins. The aortic valve directs flow through the aorta and thence to the periphery. There are normally no direct connections between the ventricles or between the atria.

The mechanical heartbeat is triggered by an electrical impulse which spreads throughout the cardiac tissue. Opening and closing of heart valves may occur primarily as a result of pressure differences between chambers, those pressures resulting from either passive filling or chamber contraction. For example, the opening and closing of the mitral valve may occur as a result of the pressure differences between the left atrium and the left ventricle.

At the beginning of ventricular filling (diastole) the aortic and pulmonary valves are closed to prevent back flow from the arteries into the ventricles. Shortly thereafter, the AV valves open to allow unimpeded flow from the atria into the corresponding ventricles. Shortly after ventricular systole (i.e., ventricular emptying) begins, the tricuspid and mitral valves normally shut, forming a seal which prevents flow from the ventricles back into the corresponding atria.

Unfortunately, the AV valves may become damaged or may otherwise fail to function properly, resulting in improper closing. The AV valves are complex structures that generally include an annulus, leaflets, chordae and a support structure. Each atrium interfaces with its valve via an atrial vestibule. The mitral valve has two leaflets; the analogous structure of the tricuspid valve has three leaflets, and opposition or engagement of corresponding surfaces of leaflets against each other helps provide closure or sealing of the valve to prevent blood flowing in the wrong direction. Failure of the leaflets to seal during ventricular systole is known as malcoaptation, and may allow blood to flow backward through the valve (regurgitation). Heart valve regurgitation can have serious consequences to a patient, often resulting in cardiac failure, decreased blood flow, lower blood pressure, and/or a diminished flow of oxygen to the tissues of the body. Mitral regurgitation can also cause blood to flow back from the left atrium to the pulmonary veins, causing congestion. Severe valvular regurgitation, if untreated, can result in permanent disability or death.

Description of the Related Art

A variety of therapies have been applied for treatment of mitral valve regurgitation, and still other therapies may have been proposed but not yet actually used to treat patients. While several of the known therapies have been found to provide benefits for at least some patients, still further options would be desirable. For example, pharmacologic agents (such as diuretics and vasodilators) can be used with patients having mild mitral valve regurgitation to help reduce the amount of blood flowing back into the left atrium. However, medications can suffer from lack of patient compliance. A significant number of patients may occasionally (or even regularly) fail to take medications, despite the potential seriousness of chronic and/or progressively deteriorating mitral valve regurgitation. Pharmacological therapies of mitral valve regurgitation may also be inconvenient, are often ineffective (especially as the condition worsens), and can be associated with significant side effects (such as low blood pressure).

A variety of surgical options have also been proposed and/or employed for treatment of mitral valve regurgitation. For example, open-heart surgery can replace or repair a dysfunctional mitral valve. In annuloplasty ring repair, the posterior mitral annulus can be reduced in size along its circumference, optionally using sutures passed through a mechanical surgical annuloplasty sewing ring to provide coaptation. Open surgery might also seek to reshape the leaflets and/or otherwise modify the support structure. Regardless, open mitral valve surgery is generally a very invasive treatment carried out with the patient under general anesthesia while on a heart-lung machine and with the chest cut open. Complications can be common, and in light of the morbidity (and potentially mortality) of open-heart surgery, the timing becomes a challenge—sicker patients may be in greater need of the surgery, but less able to withstand the surgery. Successful open mitral valve surgical outcomes can also be quite dependent on surgical skill and experience.

Given the morbidity and mortality of open-heart surgery, innovators have sought less invasive surgical therapies. Procedures that are done with robots or through endoscopes are often still quite invasive, and can also be time consuming, expensive, and in at least some cases, quite dependent on the surgeon's skill. Imposing even less trauma on these sometimes frail patients would be desirable, as would be providing therapies that could be successfully implemented by a significant number of physicians using widely distributed skills. Toward that end, a number of purportedly less invasive technologies and approaches have been proposed. These include devices which seek to re-shape the mitral annulus from within the coronary sinus; devices that attempt to reshape the annulus by cinching either above to below the native annulus; devices to fuse the leaflets (imitating the Alfieri stitch); devices to re-shape the left ventricle, and the like.

Perhaps most widely known, a variety of mitral valve replacement implants have been developed, with these implants generally replacing (or displacing) the native leaflets and relying on surgically implanted structures to control the blood flow paths between the chambers of the heart. While these various approaches and tools have met with differing levels of acceptance, none has yet gained widespread recognition as an ideal therapy for most or all patients suffering from mitral valve regurgitation.

Because of the challenges and disadvantages of known minimally invasive mitral valve regurgitation therapies and implants, still further alternative treatments have been proposed. Some of the alternative proposals have called for an implanted structure to remain within the valve annulus throughout the heart beat cycle. One group of these proposals includes a cylindrical balloon or the like to remain implanted on a tether or rigid rod extending between the atrium and the ventricle through the valve opening. Another group relies on an arcuate ring structure or the like, often in combination with a buttress or structural cross-member extending across the valve so as to anchor the implant. Unfortunately, sealing between the native leaflets and the full perimeter of a balloon or other coaxial body may prove challenging, while the significant contraction around the native valve annulus during each heart beat may result in significant fatigue failure issues during long-term implantation if a buttress or anchor interconnecting cross member is allowed to flex. Moreover, the significant movement of the tissues of the valve may make accurate positioning of the implant challenging regardless of whether the implant is rigid or flexible.

In light of the above, it would be desirable to provide improved medical devices, systems, and methods. It would be particularly desirable to provide new techniques for treatment of mitral valve regurgitation and other heart valve diseases, and/or for altering characteristics of one or more of the other valves of the body. The need remains for a device which can directly enhance leaflet coaptation (rather than indirectly via annular or ventricular re-shaping) and which does not disrupt leaflet anatomy via fusion or otherwise, but which can be deployed simply and reliably, and without excessive cost or surgical time. It would be particularly beneficial if these new techniques could be implemented using a less-invasive approach, without stopping the heart or relying on a heart-lung machine for deployment, and without relying on exceptional skills of the surgeon to provide improved valve and/or heart function.

SUMMARY

In some embodiments, a system is provided. The system can include an anchor comprising a proximal end and a distal end, the distal end configured to engage tissue. The system can include a suture coupled to the proximal end of the anchor. The system can include an implantable medical device, wherein the suture is configured to pass through at least a portion of the implantable medical device. The system can include a clip comprising at least two strands twisted together. In some embodiments, the suture is configured to pass through at least a portion of the clip after passing through the implantable medical device. In some embodiments, the suture is configured to pass through at least a portion of the clip as the clip slides toward the implantable medical device and the anchor.

The system can include a needle on an end of the suture. In some embodiments, the at least two strands are nitinol. In some embodiments, the at least two strands comprise a shape memory material. In some embodiments, the clip is linear. In some embodiments, the clip is non-linear. In some embodiments, the anchor comprises a helical portion. In some embodiments, the anchor comprises a needle radially surrounded by the anchor. In some embodiments, the implantable medical device is a coaptation assistance device configured to improve leaflet coaptation of a cardiac valve. In some embodiments, the suture passes from one surface of the implantable medical device to a second, opposed surface of the implantable medical device. In some embodiments, the suture forms a loop on one side of the clip.

In some embodiments, a system is provided. The system can include a delivery tool comprising an outer sleeve and an inner shaft. In some embodiments, the inner shaft is operably coupled to a control handle configured to move the inner shaft relative to the outer sleeve. The system can include a lasso extending through the inner shaft, the lasso configured to engage a suture. The system can include a clip disposed on the inner shaft. In some embodiments, the control handle is configured to pull the lasso and the suture inside the inner shaft. In some embodiments, after the lasso and the suture are pulled inside the inner shaft, the outer sleeve is configured to push the clip off the inner shaft.

In some embodiments, the clip comprises at least two strands twisted together. In some embodiments, the at least two strands are nitinol. In some embodiments, the at least two strands comprise a shape memory material. In some embodiments, the clip is linear. In some embodiments, the clip is non-linear. The system can include the suture and an anchor, wherein the suture extends from the anchor. In some embodiments, the anchor comprises a helical portion. In some embodiments, the anchor comprises a central needle. The system can include the suture and the implantable medical device, wherein the suture extends through the implantable medical device. In some embodiments, the implantable medical device is a coaptation assistance device configured to improve leaflet coaptation of a cardiac valve. In some embodiments, the suture passes from one surface of the implantable medical device to a second, opposed surface of the implantable medical device. In some embodiments, the suture forms a loop on one side of the clip after the lasso and the suture is pulled inside the inner shaft. In some embodiments, the suture forms a loop on one side of the clip after the clip is pushed off the inner shaft.

In some embodiments, a method of anchoring is provided. The method can include the step of extending a suture from an anchor and through an implantable medical device. The method can include the step of extending the suture through a clip after extending the suture through the implantable medical device, wherein the suture passes through at least a portion of the clip as the clip slides toward the implantable medical device and the anchor.

In some embodiments, the extending a suture from an anchor and through an implantable medical device comprises extending a needle on an end of the suture through the implantable medical device. In some embodiments, extending the suture through a clip comprises extending the suture between two strands of wire twisted together. In some embodiments, the clip comprises at least two strands twisted together. In some embodiments, the clip comprises two or more nitinol wires. In some embodiments, the clip is linear. In some embodiments, the clip is non-linear. In some embodiments, the anchor comprises a helical portion. The method can include the step of driving a helical portion of the anchor into tissue. The method can include the step of engaging the anchor with tissue. The method can include the step of engaging the anchor with cardiac tissue. In some embodiments, the anchor comprises a central needle. The method can include the step of driving a central needle into tissue, the anchor surrounding the central needle. In some embodiments, the implantable medical device is a coaptation assistance device. The method can include the step of passing the suture from one surface of the implantable medical device to another, opposed surface of the implantable medical device. The method can include the step of forming a loop of the suture on one side of the clip. The method can include the step of sliding the clip toward the implantable medical device. In some embodiments, the clip is initially disposed on the inner shaft of a tool, further comprising pushing the clip from the inner shaft of the tool. In some embodiments, the clip is initially disposed on the inner shaft of a tool, the inner shaft having a lasso extending therethrough, further comprising threading the suture through the lasso. The method can include the step of pulling the lasso and the suture into the inner shaft. The method can include the step of pulling a loop of the suture through the clip. The method can include the step of lowering the inner shaft and the clip toward the implantable medical device and the anchor. The method can include the step of pushing the clip off the inner shaft. The method can include the step of pushing the clip off the inner shaft with an outer sleeve of the tool. The method can include the step of placing the clip adjacent to the implantable medical device. The method can include the step of placing the implantable medical device adjacent to the tissue. The method can include the step of placing the implantable medical device adjacent to the anchor.

BRIEF DESCRIPTION OF THE DRAWINGS

FIG. 7 illustrates an embodiment of an anchor with a linked suture mechanism.

FIG. 8 illustrates an embodiment of an anchor with a releasable L-lock feature.

FIGS. 23A-23E illustrates an embodiment of an arrangement of clips according to some methods of use.

FIG. 32 illustrates an embodiment of a clip.

FIGS. 43A-43G illustrates embodiments of an anchor.

DETAILED DESCRIPTION

Figure 1A:
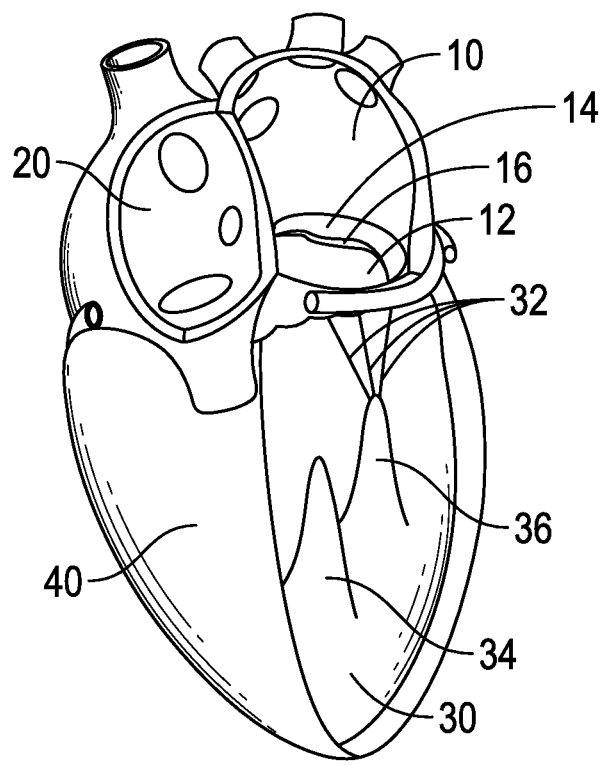
FIGS. 1A-1F schematically illustrate some of the tissues of the heart and mitral valve, as described in the Background section and below, and which may interact with the implants and systems described herein
Figure 1B:
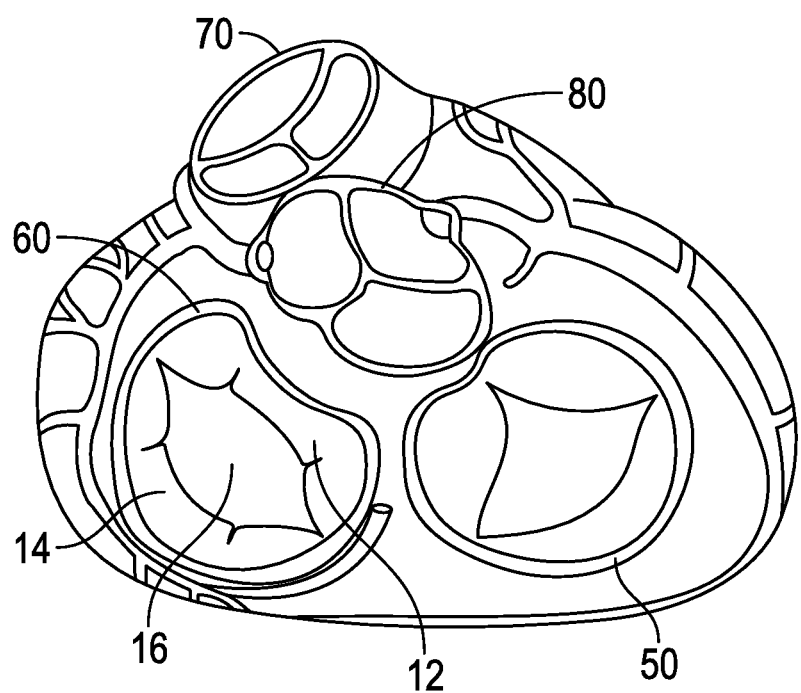
Figure 1C:
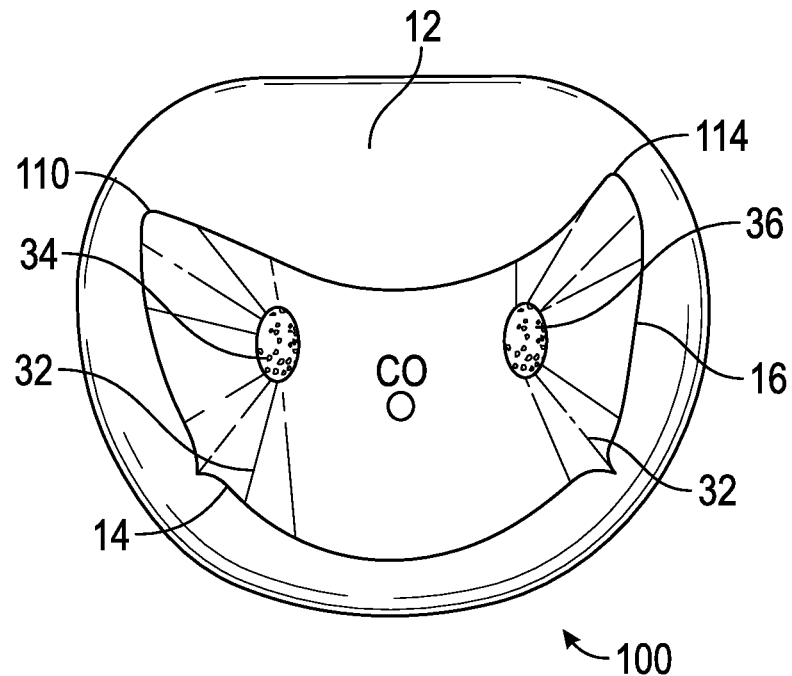
Figure 1D:
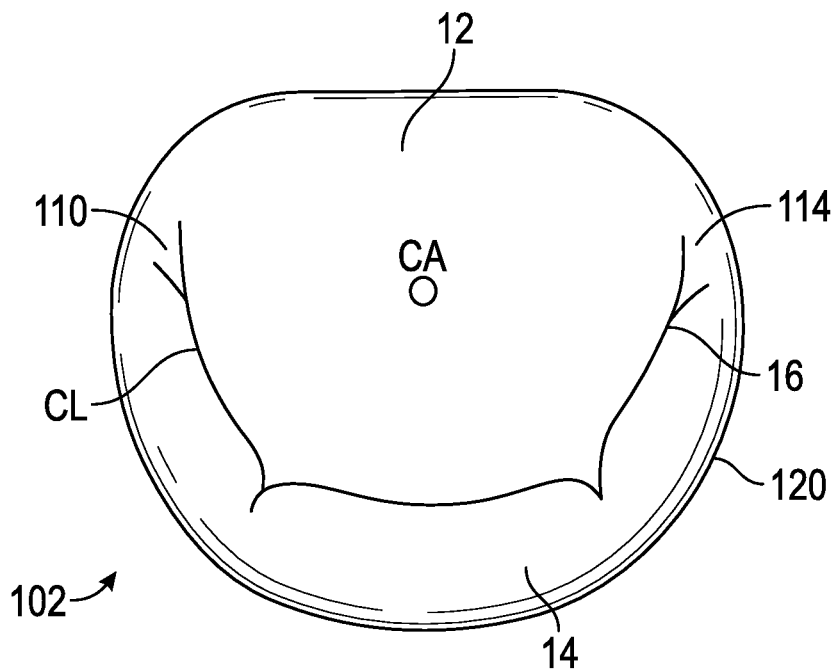

The devices, systems and methods described within this disclosure, in some embodiments, are generally for the treatment of mitral valve regurgitation (MR). However, devices, systems, and methods as disclosed herein can also be utilized for other cardiac as well as non-cardiac indications, including those involving the mitral, aortic, tricuspid, and/or pulmonic valves. Mitral valve regurgitation occurs when the mitral valve does not prevent the backflow of blood from the left ventricle to the left atrium during the systolic phase. The mitral valve is composed of two leaflets, the anterior leaflet and the posterior leaflet, which coapt or come together during the systolic phase to prevent backflow. There are generally two types of mitral valve regurgitations, functional and degenerative regurgitations. Functional MR is caused by multiple mechanisms including abnormal or impaired left ventricular (LV) wall motion, left ventricular dilation and papillary muscle disorders. Degenerative MR is caused by structural abnormalities of the valve leaflets and the sub-valvular tissue including stretching or rupture of the chordae. Damaged chordae may lead to prolapsing of the leaflets which means that the leaflets bulge out (generally into the atrium), or become flail if the chordae become torn, leading to backflows of blood. As will be described below, the devices, system and methods in this disclosure provide a new coaptation surface over the native posterior valve such that the backward flow of blood is minimized or eliminated.

Referring to FIGS. 1A-1D, the four chambers of the heart are shown, the left atrium 10, right atrium 20, left ventricle 30, and right ventricle 40. The mitral valve 60 is disposed between the left atrium 10 and left ventricle 30. Also shown are the tricuspid valve 50 which separates the right atrium 20 and right ventricle 40, the aortic valve 80, and the pulmonary valve 70. The mitral valve 60 is composed of two leaflets, the anterior leaflet 12 and posterior leaflet 14. In a healthy heart, the edges of the two leaflets oppose during systole at the coaptation zone 16.

Figure 1E:
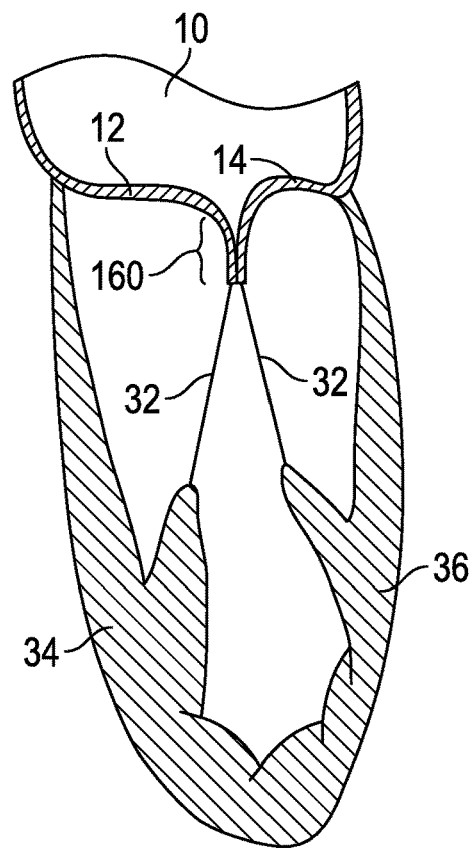

The fibrous annulus 120, part of the cardiac skeleton, provides attachment for the two leaflets of the mitral valve, referred to as the anterior leaflet 12 and the posterior leaflet 14. The leaflets are axially supported by attachment to the chordae tendinae 32. The chordae, in turn, attach to one or both of the papillary muscles 34, 36 of the left ventricle. In a healthy heart, the chordae support structures tether the mitral valve leaflets, allowing the leaflets to open easily during diastole but to resist the high pressure developed during ventricular systole. In addition to the tethering effect of the support structure, the shape and tissue consistency of the leaflets helps promote an effective seal or coaptation. The leading edges of the anterior and posterior leaflet come together along the zone of coaptation 16, with a lateral cross-section 160 of the three-dimensional coaptation zone (CZ) being shown schematically in FIG. 1E.

Figure 1F:
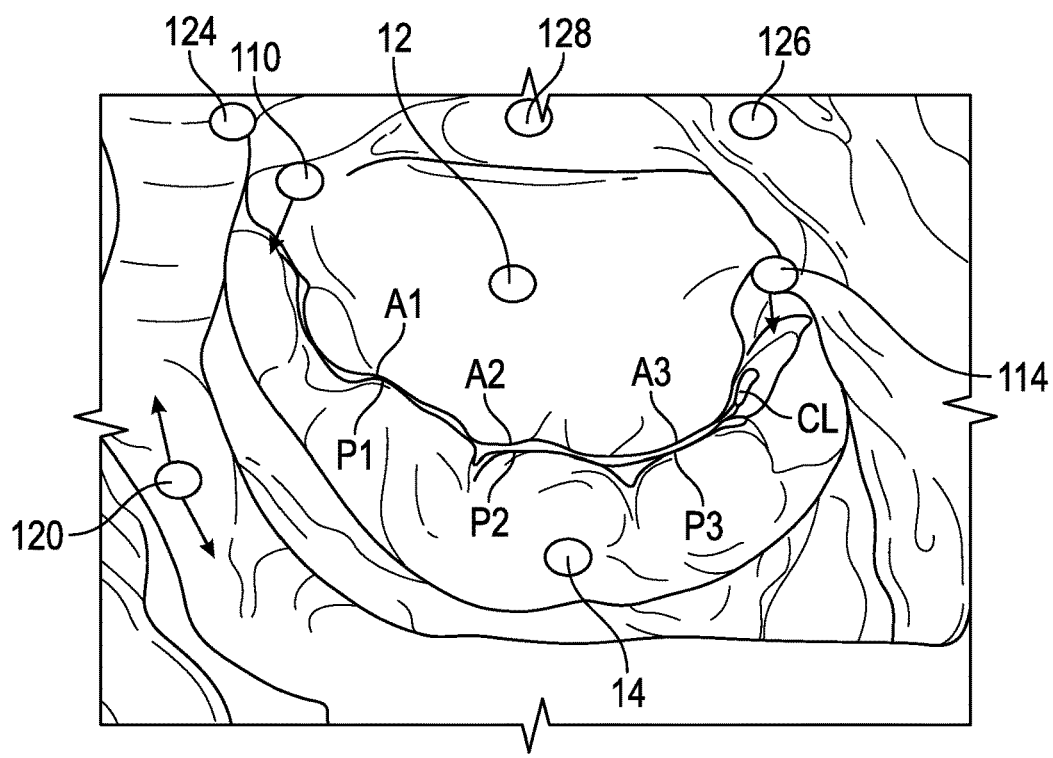

The anterior and posterior mitral leaflets are dissimilarly shaped. The anterior leaflet is more firmly attached to the annulus overlying the central fibrous body (cardiac skeleton), and is somewhat stiffer than the posterior leaflet, which is attached to the more mobile posterior mitral annulus. Approximately 80 percent of the closing area is the anterior leaflet. Adjacent to the commissures 110, 114, on or anterior to the annulus 120, lie the left (lateral) 124 and right (septal) 126 fibrous trigones which are formed where the mitral annulus is fused with the base of the non-coronary cusp of the aorta (FIG. 1F). The fibrous trigones 124, 126 form the septal and lateral extents of the central fibrous body 128. The fibrous trigones 124, 126 may have an advantage, in some embodiments, as providing a firm zone for stable engagement with one or more annular or atrial anchors. The coaptation zone CL between the leaflets 12, 14 is not a simple line, but rather a curved funnel-shaped surface interface. The first 110 (lateral or left) and second 114 (septal or right) commissures are where the anterior leaflet 12 meets the posterior leaflet 14 at the annulus 120. As seen most clearly in the axial views from the atrium of FIGS. 1C, 1D, and 1F, an axial cross-section of the coaptation zone generally shows the curved line CL that is separated from a centroid of the annulus CA as well as from the opening through the valve during diastole CO. In addition, the leaflet edges are scalloped, more so for the posterior versus the anterior leaflet. Mal-coaptation can occur between one or more of these A-P (anterior-posterior) segment pairs A1/P1, A2/P2, and A3/P3, so that mal-coaptation characteristics may vary along the curve of the coaptation zone CL.

Figure 2A:
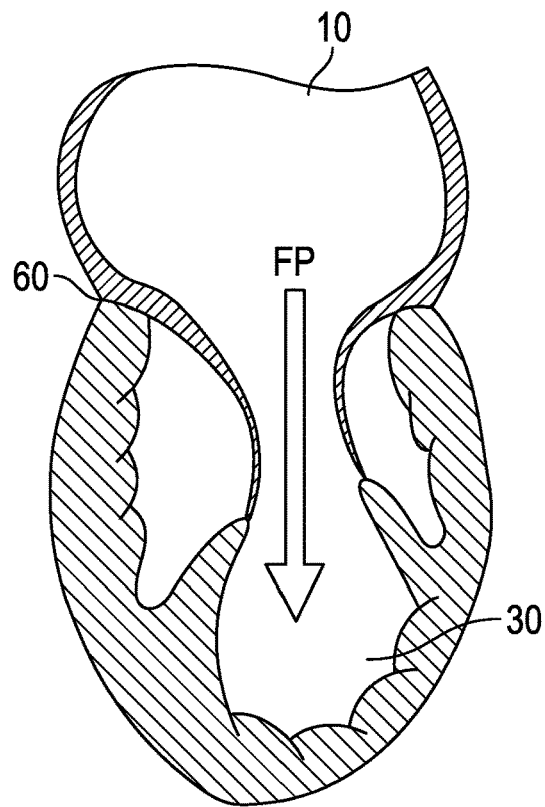
FIG. 2A illustrates a simplified cross-section of a heart, schematically showing mitral valve function during diastole.
Figure 2B:
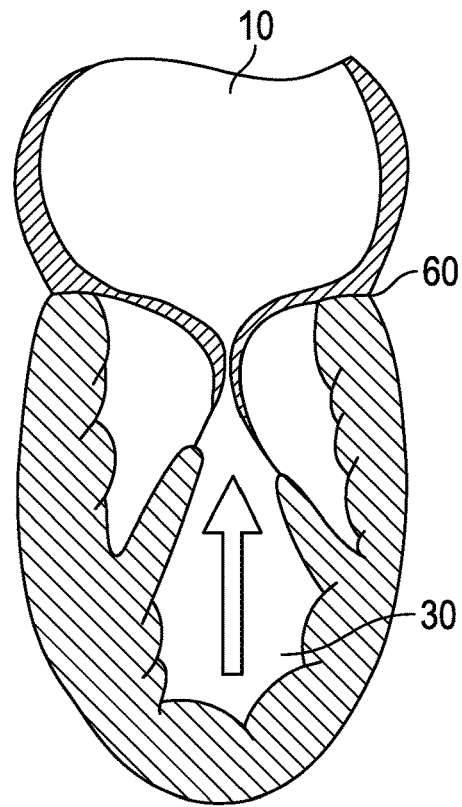
FIG. 2B illustrates a simplified cross-section of a heart, schematically showing mitral valve function during systole

Referring now to FIG. 2A, a properly functioning mitral valve 60 of a heart is open during diastole to allow blood to flow along a flow path FP from the left atrium toward the left ventricle 30 and thereby fill the left ventricle. As shown in FIG. 2B, the functioning mitral valve 60 closes and effectively seals the left ventricle 30 from the left atrium 10 during systole, first passively then actively by increase in ventricular pressure, thereby allowing contraction of the heart tissue surrounding the left ventricle to advance blood throughout the vasculature.

Referring to FIGS. 3A-3B and 4A-4B, there are several conditions or disease states in which the leaflet edges of the mitral valve fail to oppose sufficiently and thereby allow blood to regurgitate in systole from the ventricle into the atrium. Regardless of the specific etiology of a particular patient, failure of the leaflets to seal during ventricular systole is known as mal-coaptation and gives rise to mitral regurgitation.

Figure 3A:
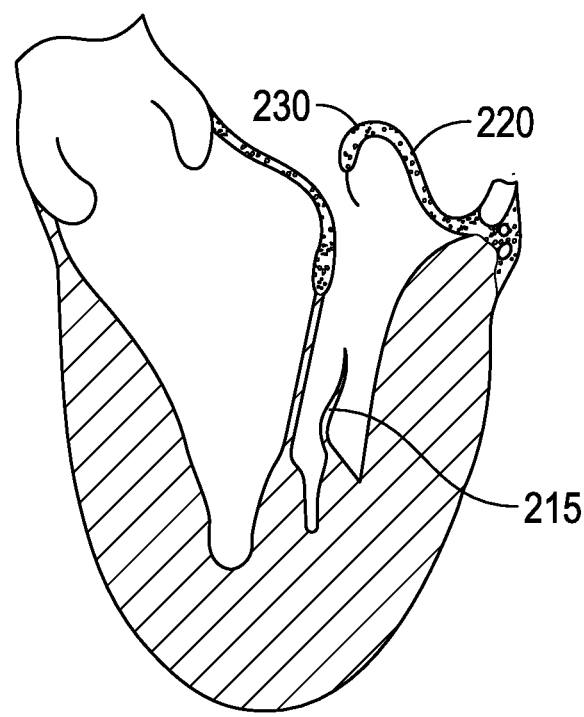
FIGS. 3A-3B illustrate a simplified cross-section of a heart, schematically showing mitral valve regurgitation during systole in the setting of mal-coaptation of the mitral valve leaflets.

Generally, mal-coaptation can result from either excessive tethering by the support structures of one or both leaflets, or from excessive stretching or tearing of the support structures. Other, less common causes include infection of the heart valve, congenital abnormalities, and trauma. Valve malfunction can result from the chordae tendinae becoming stretched, known as mitral valve prolapse, and in some cases tearing of the chordae 215 or papillary muscle, known as a flail leaflet 220, as shown in FIG. 3A. Or if the leaflet tissue itself is redundant, the valves may prolapse so that the level of coaptation occurs higher into the atrium, opening the valve higher in the atrium during ventricular systole 230. Either one of the leaflets can undergo prolapse or become flail. This condition is sometimes known as degenerative mitral valve regurgitation.

Figure 3B:
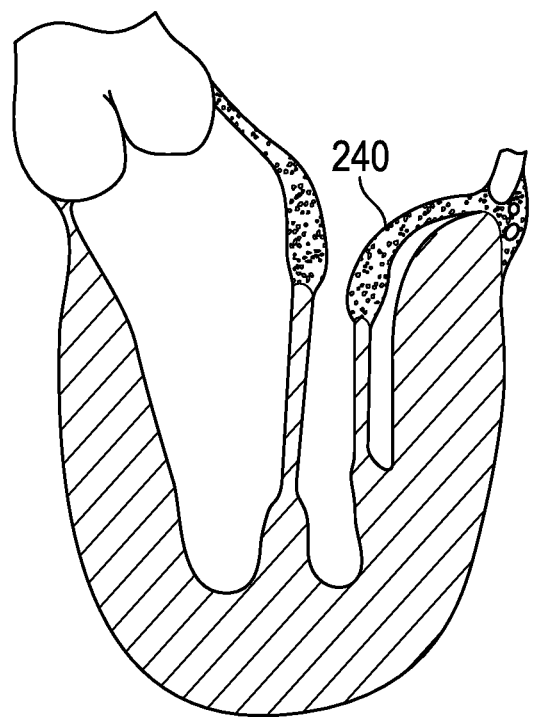

In excessive tethering, as shown in FIG. 3B, the leaflets of a normally structured valve may not function properly because of enlargement of or shape change in the valve annulus: so-called annular dilation 240. Such functional mitral regurgitation generally results from heart muscle failure and concomitant ventricular dilation. And the excessive volume load resulting from functional mitral regurgitation can itself exacerbate heart failure, ventricular and annular dilation, thus worsening mitral regurgitation.

Figure 4A:
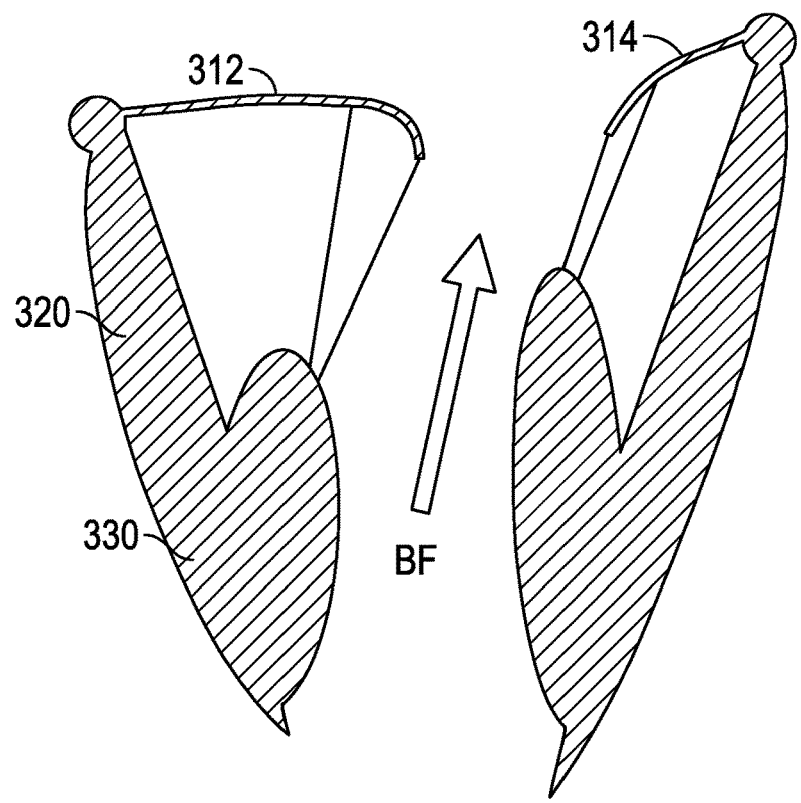
FIG. 4A illustrates a stylized cross section of a heart, showing mitral valve mal-coaptation in the settings of functional mitral valve regurgitation.
Figure 4B:
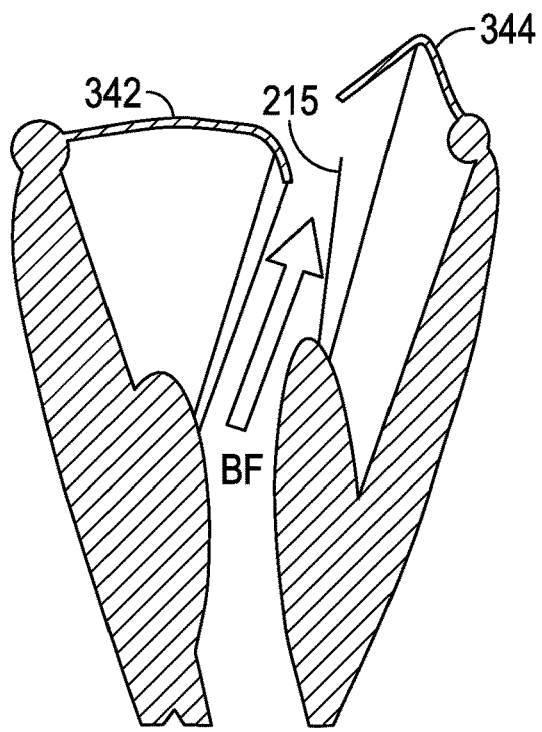
FIG. 4B illustrates a stylized cross section of a heart, showing mitral valve mal-coaptation in the settings of degenerative mitral valve regurgitation.

FIGS. 4A-4B illustrate the backflow BF of blood during systole in functional mitral valve regurgitation (FIG. 4A) and degenerative mitral valve regurgitation (FIG. 4B). The increased size of the annulus in FIG. 4A, coupled with increased tethering due to hypertrophy of the ventricle 320 and papillary muscle 330, prevents the anterior leaflet 312 and posterior leaflet 314 from opposing, thereby preventing coaptation. In FIG. 4B, the tearing of the chordae 215 causes prolapse of the posterior leaflet 344 upward into the left atrium, which prevents opposition against the anterior leaflet 342. In either situation, the result is backflow of blood into the atrium, which decreases the effectiveness of left ventricle compression.

Disclosed herein are systems and methods to secure intracardiac implants, such as replacement heart valves, annuloplasty rings, cardiac patches, left atrial appendage devices, patent foramen ovale, ASD, or VSD closure devices, sensors, pacemakers, AICDs, ventricular assist devices, drug delivery devices, and coaptation assist devices, for example, in place within the heart. The implant can be any device known in the art, including those disclosed in U.S. patent application Ser. No. 14/742,199. In some embodiments, disclosed herein are tissue anchoring mechanisms for such implants. In some embodiments, disclosed herein are clip mechanisms to secure implants to the anchors that can be already embedded in tissue. In some embodiments, systems and methods as disclosed herein can be utilized with those disclosed in U.S. Pat. Nos. 8,845,717, 8,888,843, or U.S. patent application Ser. No. 14/742,199, which are all hereby incorporated by reference in their entireties. These anchors, which can be described in some embodiments as annular, atrial, and/or ventricular anchors, or generically as "anchors". The anchors, in some embodiments, may take various forms or combinations of forms and include, for example, screws, treble hooks, grappling hooks, barbs, staples, umbrella-like elements, T-bars, and the like, as described herein. A suture clip can be used as described herein. The suture clip can advantageously allow rapid attachment of an implant to an anchor, as described herein. A suture clip can include a clip structured out of a shape memory material, such as nitinol. The suture clip can include ends capped by a crimped hypotube as described herein.

Figure 5A:
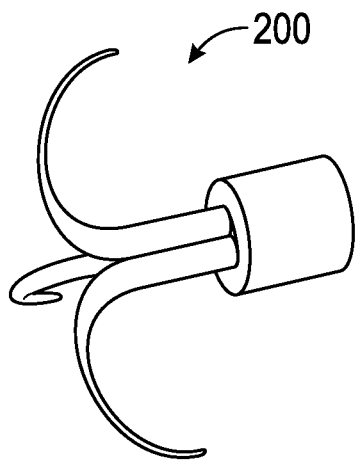
FIGS. 5A-5E illustrates embodiments of annular anchoring.
Figure 5B:
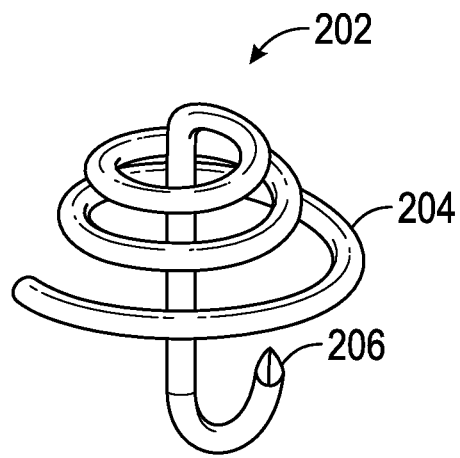

FIGS. 5A-5E illustrates various embodiments of annular anchors. In some methods of use, the anchors can be part of the initial implant deployment process. The anchors can hold the implant while secondary anchors are placed. In some embodiments, the secondary anchors pierce the implant and underlying tissue, securing the implant to the tissue. In some embodiments, the primary and/or secondary anchors could include grappling hooks (as illustrated in FIG. 5A), stacked helical coils (as illustrated in FIG. 5B), spiral umbrella coils, and the like. FIG. 5A shows an anchor 200 with grappling hooks. FIG. 5B shows an anchor 202 that resembles an umbrella. The anchor 202 can include a spiral 204 that increases in diameter distally or proximally. The anchor 202 can include a sharpened point 206. In both embodiments, the anchors 200, 202 may be made of a shape memory material, stainless steel, or other biocompatible materials.

Figure 5C:
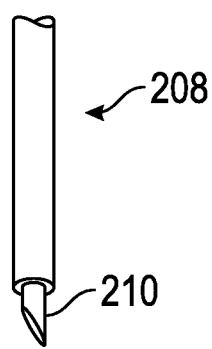

In both embodiments, the anchors may be loaded into a delivery catheter such as the delivery catheter 208 illustrated in FIG. 5C. Locking mechanisms such as those described herein may be used to reversibly lock the anchors to the delivery catheter. The delivery catheter 208 may have a pointed end 210 so that the delivery catheter 208 may be guided to an appropriate location and initially pierce the tissue. After the delivery catheter 208 is placed at an appropriate location and the initial piercing is accomplished, one or more of the anchors may be advanced and set in place. This step is followed by unlocking and retracting the delivery catheter 208. In some embodiments, the initial delivery of the anchors could be, for example, from a straight tube having a sidewall with sufficient column strength to keep the anchors in a first constrained configuration (as illustrated in FIG. 5C), the anchors transformable to a second deployed configuration (as illustrated in FIG. 5D).

Figure 5D:
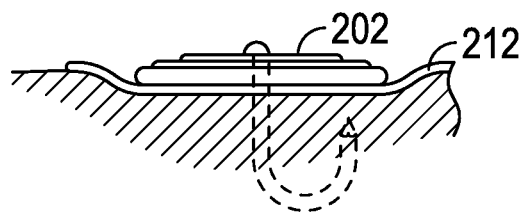

FIG. 5D is an illustration of how the umbrella anchor 202 of FIG. 5B may look after it has been set into the tissue to anchor the coaptation assistance device 212 or other implant. Due to the natural unstressed shape of the anchor 202, when deployed in the tissue over the coaptation assistance device 212, the deformed shape would have an effective spring-force on the face of the coaptation assistance device 212, ensuring a good foothold and surface area to interface with the tissue to be anchored.

Figure 5E:
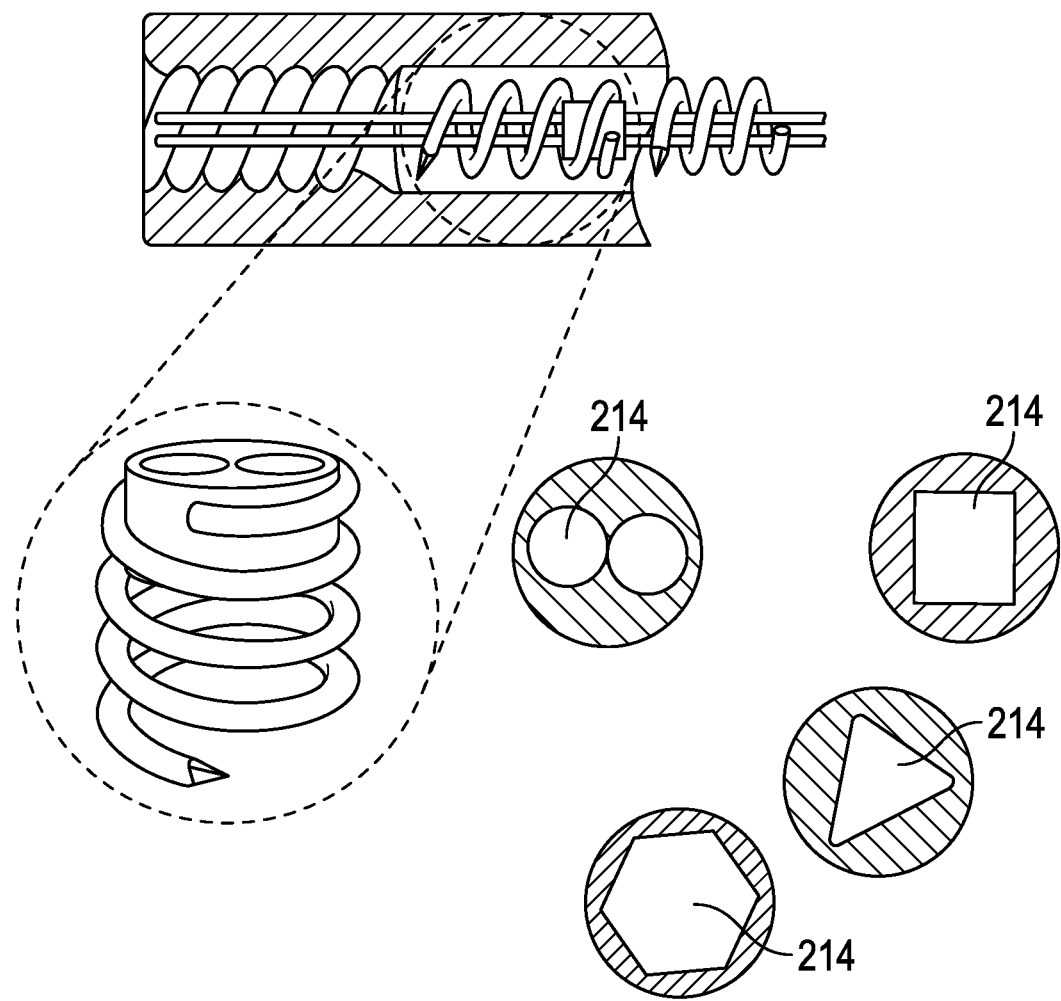

Also shown herein in FIG. 5E are different drive shaft apertures to accommodate various geometries of drive shafts. The drive shaft apertures 214 could have a circular, square, triangular, or hexagonal cross-section as shown, although other geometries, including rectangular, pentagonal, and others are also possible.

Figure 6A:
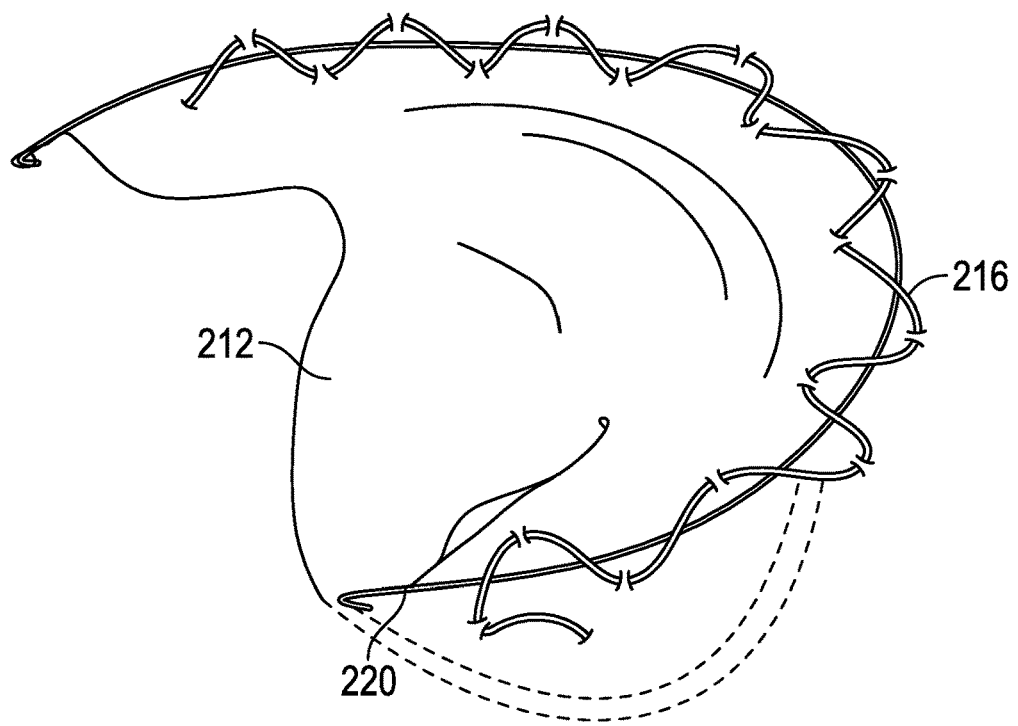
FIGS. 6A-6G illustrates embodiments of secondary anchoring.

FIGS. 6A-6F illustrate embodiments of secondary anchoring. FIG. 6A shows an embodiment for anchoring the coaptation assistance device 212. In FIG. 6A, a suture or tape 216 is used to "sew" the coaptation assistance device 212 to the tissue. The suture or tape 216 may be made of one of several materials including, but not limited to, polypropylene or nylon. FIG. 6A illustrates a coaptation assist device 212 having the tap 218 interwoven along its superior edge 220. In some embodiments, the MR is assessed while securing the coaptation assistance device 212 and the pitch and/or the location of the sewing action is determined according to the presence or absence of the MR.

Figure 6B:
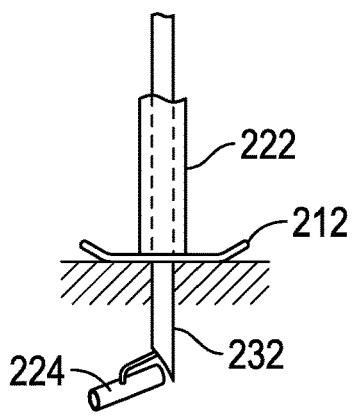
Figure 6C:
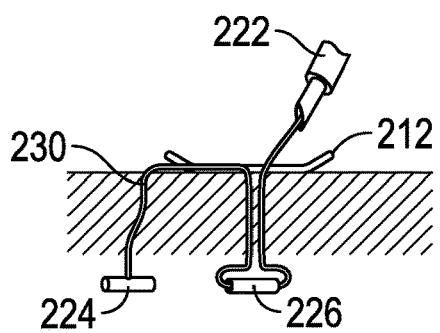
Figure 6D:
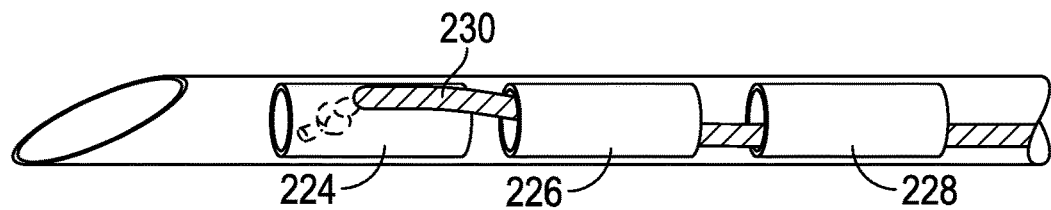

FIG. 6B-6D shows another embodiment of an anchor catheter 222 that delivers multiple anchors. The anchor catheter 222 can have a hollow shaft. The hollow shaft can be pointed at the distal end which may be used to pierce the coaptation assistance device 212 and tissue. Multiple anchors 224, 226, 228 may be arranged within the hollow shaft of the anchor catheter 222. The anchors 224, 226, 228 can be hollow barrels or other configurations.

A suture 230 may be threaded through the anchors 224, 226, 228 as shown. The suture 230 may be secured to the first anchor 224 by arranging the suture 230 to exit the second anchor 226 and enter the first anchor 224 through a side aperture. The suture 230 may then be secured by means of a knot as depicted in dotted lines within the first anchor 224. The suture 230 in the other anchors 226, 228, except the first anchor 224, may appear as illustrated for the anchor 226. The anchors 226, 228, except the first anchor 224 have a portion of their walls cut out. The cut outs can aid in better trapping the anchors within the tissue, similar to a togglebolt. At the proximal end of the anchor catheter 222, a feature such as a pusher tube 232 may be present to cause the anchors 224, 226, 228 to exit the anchor catheter 222 at the distal end. The pusher 232 may be attached to a handle (not shown) so as to enable an operator to deposit one or more anchors 224, 226, 228 when appropriate.

FIG. 6B-C illustrates how the anchor catheter 222 of FIG. 6D may operate. In FIG. 6B, the anchor catheter 222 can be advanced through the coaptation assistance device 212 through a slot. The anchor catheter 222 then pierces the tissue. The operator pushes the first anchor 224 out of the anchor catheter 222, depositing the anchor 224 within the tissue. Once the first anchor 224 is deposited, the rest of the anchors 226, 228 are deposited as illustrated in FIG. 6C. In FIG. 6C, the anchor catheter 222 is pulled out of the tissue after depositing the first anchor 224 in order to enter a second location. At the second location, the anchor catheter 222 can deposit the second anchor 226. This process is continued until desired to secure the coaptation assistance device 212 to the tissue. After the last anchor 228 is delivered, a cutter (not shown) can be advanced inside the anchor catheter 222 to cut the suture 230, leaving behind the anchors 224, 226, 228.

In some embodiments, the anchors 224, 226, 228 may be radio opaque or they may be covered by a radio graphic marker. During the process of delivery of the anchors 224, 226, 228, the radio opaque markers may be visualized if a fluoroscope is used. This may help in spacing the anchors 224, 226, 228 around the annulus of the coaptation assistance device 1200.

Figure 6E:
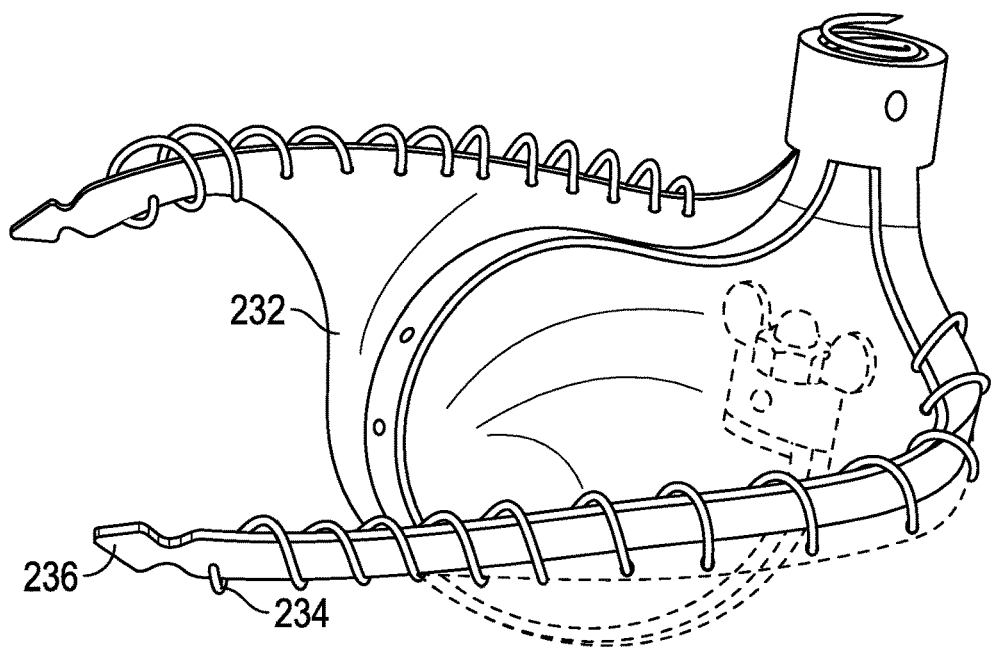
Figure 6F:
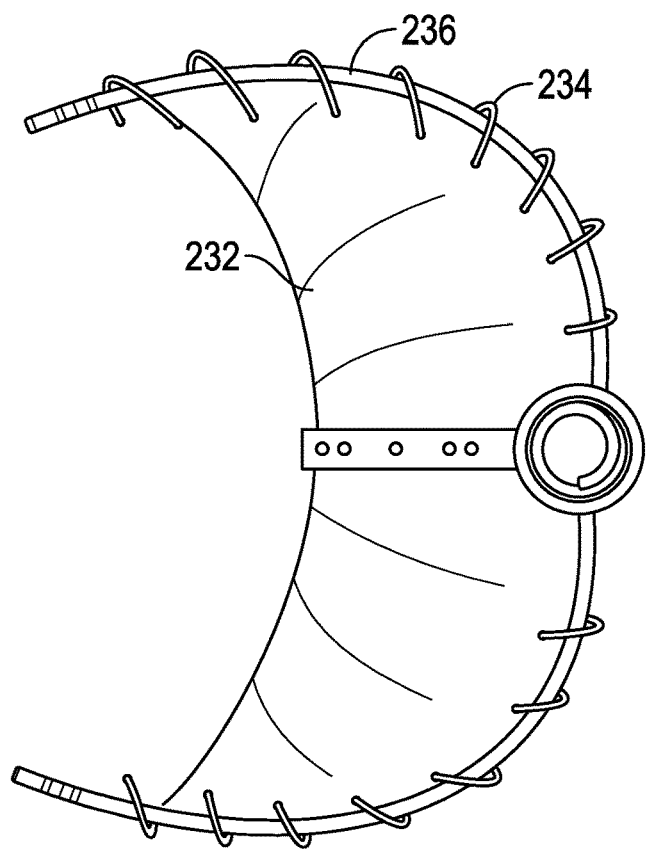

As illustrated in FIG. 6B-6D, the anchors 224, 226, 228 could include suture-linked 230 toggle bolts. The anchors could include a spiral continuous anchor as shown in FIGS. 6A, 6E, and 6F. Other anchor designs are shown and described in U.S. application Ser. No. 14/742,199, incorporated by reference herein.

FIG. 6E-6F shows an embodiment for anchoring the coaptation assistance device 232 or other implant. In FIGS. 6E and 6F, a suture or tape 234 is used to "sew" the coaptation assistance device 232 to the tissue. The suture or tape 234 may be made of one of several materials including, but not limited to, polypropylene or nylon. FIG. 6E illustrates a coaptation assist device 232 having the tape 234 interwoven along its superior edge 236.

Figure 6G:
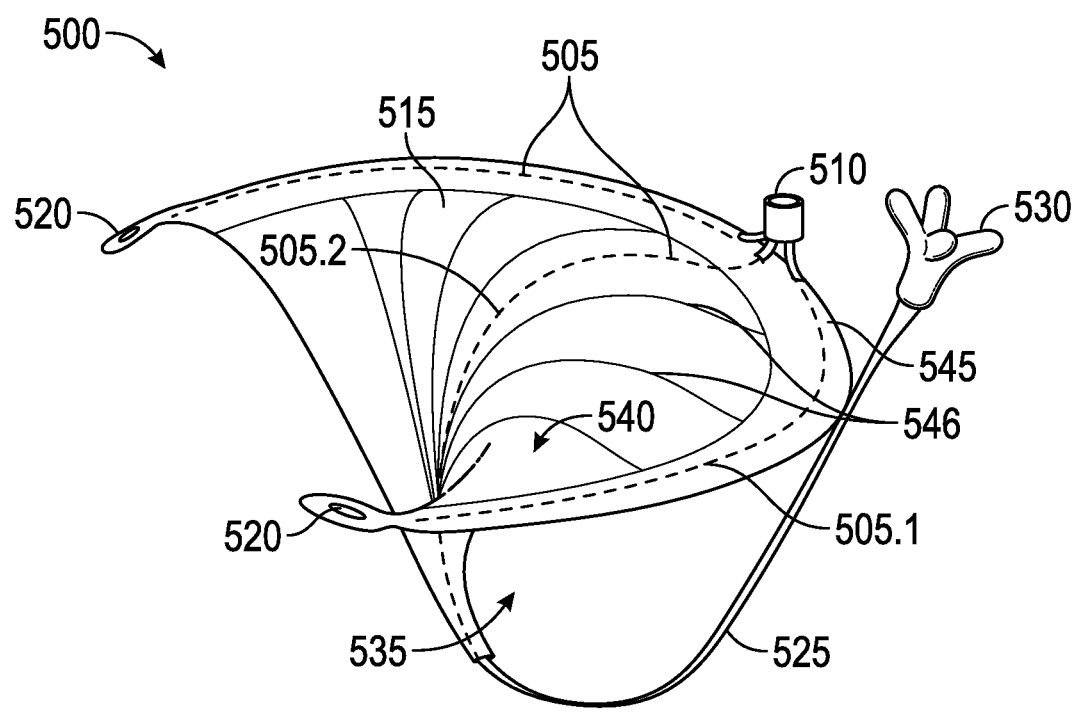

FIG. 6G illustrates an embodiment of a coaptation assistance device 500. The coaptation assistance device 500 can include a coaptation assistance body 515. The coaptation assist body 515 can include a first coaptation surface 535. The first coaptation surface 535 can be disposed toward a mal-coapting native leaflet, in the instance of a mitral valve, the posterior leaflet when implanted. The coaptation assist body 515 can include a second coaptation surface 540. The second coaptation surface 540 can be opposed to the first coaptation surface 535 as shown in FIG. 6G. The second coaptation surface 540 can be disposed toward a mal-coapting native leaflet, in the instance of a mitral valve, the anterior leaflet when implanted. The first coaptation surface 535 and the second coaptation surface 540 can be bounded by a first lateral edge and a second lateral edge. The first coaptation surface 535 and the second coaptation surface 540 can be bounded by an inferior edge and a superior edge 545.

The first coaptation surface 535 and the second coaptation surface 540 are two sides of the same implant structure forming the coaptation assistance body 515. The shape of the coaptation assistance body 515 may be characterized generally, in some embodiments, by the shape of the superior edge 545, the shape of the first coaptation surface 535, and the second coaptation surface 540.

The coaptation assistance device 500 can include a ventricular projection 525 as shown in FIG. 6G. The ventricular projection 525 can extend from the inferior edge of the coaptation assistance body 515. The ventricular projection 525 can be placed within the left ventricle when implanted. The ventricular projection 525 can provide an anchoring mechanism. The distal end 530 of the ventricular projection 525 generally provides the anchoring mechanism. The distal end 530 of the ventricular projection 525 may have different shapes.

The coaptation assistance device 500 can include a support structure 505. The support structure 505 can be referred to as a spine. The support structure 505 can define, at least in part, the shape of the coaptation assistance device 500.

In FIG. 6G, the support structure 505 is shown by dotted lines. In some embodiments, the support structure 505 is made of a shape memory material such as but not limited to nitinol (NiTi), polyether ether ketone (PEEK) or other stiff polymer or fatigue resistant metal. The use of shape memory materials enables advantages described herein. For example, one advantage of a shape memory material is that its superelastic properties helps the coaptation assistance device 500 maintain its shape and functionality as a coaptation assistance device as the heart contracts and dilates and exerts pressure on the coaptation assistance device 500. Another example of an advantage is that a shape memory material lends itself to percutaneous delivery methods which will be described herein.

The support structure 505 can include one or more section. In some embodiments, the support structure 505 includes one section. In some embodiments, the support structure 505 includes two sections. In some embodiments, the support structure 505 includes three or more sections. In some embodiments, one or more sections of the support structure 505 can include one or more subsection. In the embodiment shown in FIG. 5A, the support structure 505 includes two sections: a first section 505.2 and a second section 505.1.

The first section 505.2 can extend through at least a portion of the coaptation assistance device 500 between the superior edge 545 and the ventricular projection 525. In some embodiments, the first section 505.2 can extend through the entire length between of the coaptation assistance device 500 between the superior edge 545 and the ventricular projection 525. In some embodiments, the first section 505.2 extends from a location between the superior edge 545 and the inferior edge of the coaptation assistance body 515. In some embodiments, the first section 505.2 extends from a location between the inferior edge of the coaptation assistance body 515 and the ventricular projection 525. In some embodiment, the first section 505.2 extends along the coaptation assistance body 515 and continues on to support the ventricular projection 525.

The second section 505.1 can extend through at least a portion of the coaptation assist body 515 between the first lateral edge and the second lateral edge. In some embodiments, the second section 505.1 can extend through the entire length between of the first lateral edge and the second lateral edge. In some embodiments, the second section 505.1 extends from a location between the superior edge 545 and the inferior edge of the coaptation assistance body 515. In some embodiments, the second section 505.1 extends from a location closer to the superior edge 545 than the inferior edge of the coaptation assistance body 515. In some embodiments, the second section 505.1 extends from the first lateral edge toward the second lateral edge. In some embodiments, the second section 505.1 extends from the second lateral edge toward the first lateral edge. In some embodiments, the second section 505.1 extends along a section between the first lateral edge and the second lateral edge. In some embodiments, the second section 505.1 extends along the edge of the coaptation assistance device 500.

In some embodiments, the first section 505.2 and the second section 505.1 of the support structure 505 may be one integral piece or unitary structure. In some embodiments, the first section 505.2 and the second section 505.1 of the support structure 505 are separate components. In some embodiments, the first section 505.2 and the second section 505.1 may be two separate sections joined together by methods such as but not limited to crimping and laser welding.

In some embodiments, the first section 505.2 is integrated within the coaptation assistance body 515 as described herein. In some embodiments, the first section 505.2 in integrated within the ventricular projection 525 as described herein. In some embodiments, the first section 505.2 is removable from the coaptation assistance body 515 as described herein. In some embodiments, the first section 505.2 is removable from the ventricular projection 525 as described herein. In some embodiments, the second section 505.1 is integrated within the coaptation assistance body 515 as described herein. In some embodiments, the second section 505.1 is removable from the coaptation assistance body 515 as described herein. In some embodiments, the first section 505.2 can have a first zone that is generally oriented substantially parallel to a longitudinal axis of the body 515, and a second zone that is generally oriented substantially perpendicular to the longitudinal axis of the body 515 as illustrated.

When the coaptation assistance device 500 is placed within the heart, the coaptation assistance device 500 is such that, in some embodiments, the ventricular projection 525 will generally be placed within the left ventricle as shown in FIG. 5G. The ventricular projection 525 provides a mechanism to anchor the coaptation assistance device 500 using the structure of the ventricles. An example of positioning of the coaptation assistance device 500 over the posterior leaflet is illustrated in FIG. 5G.

Bearing in mind that other examples of positioning are possible and are discussed elsewhere within this disclosure, in this particular example, the coaptation assistance device 500 is illustrated with a ventricular projection 525 that has a curved shape. The ventricular projection 525 and/or the first support 505.2 may be composed of shape memory materials, in which case the curved shape is retained after implantation. The curved shape may enable the coaptation assistance device 500 to stay in position as engages to the native posterior leaflet 14.

FIG. 7 illustrates an embodiment of an anchor with a linked suture mechanism. FIG. 7 illustrates a screw-type anchor, but other anchor designs are contemplated. The anchor is operably coupled to a linked suture mechanism. The anchor can embed itself in the tissue of a patient, for example, the endocardium and/or myocardium. The linked suture mechanism can couple one anchor to another anchor as described in U.S. Prov. App. No. 62/014,060.

FIG. 7 shows an embodiment of an anchor catheter 238 that delivers multiple anchors. Several anchors 240 can be stacked within the anchor catheter 238. Each anchor 240 may include a coil section 242. The coil section 242 can include a pointed end 244. The anchor 2240 may include an anchor head 246. The anchor head 246 may have one of several cross sections shown by FIG. 5E. Other cross sections are possible.

FIG. 7 illustrates a central suture 248 configured to be housed within the central lumen of a coil. The central suture 248 can include a ball 250 coupled to the end of the central suture 248. FIG. 7 illustrate how the central suture 248 and ball 250 may be used. The ball 250 can sit in a pocket inside the first anchor 240. The central suture 248 can connect the first anchor 240 to another anchor (not shown in the figure). This arrangement may provide the ability to use the central suture 248 as a guide wire to return back to an anchor 240 after the anchor 240 has been screwed into the tissue. The operator may wish to return to the anchor 240 to reposition or adjust the anchor 240. In addition, if one or more anchors 240 came loose, the central suture 248 may provide a tether for the loose anchors 240, therefore preventing embolic events.

FIG. 8 illustrates an embodiment of an anchor with a releasable L-lock feature. Referring to FIG. 8, the delivery catheter 252 and an anchor 254 can have matching or complementary features that enable them to be locked temporarily. In some embodiments, the delivery catheter 252 includes one or more distal locking tabs 256. The anchor 254 can include the hub 258. The distal locking tabs 256 of the delivery catheter 252 may couple with features in the hub 258. Distal locking tabs 256 may be made, for example, of some shape memory material such as nitinol. The natural position of the locking tabs 256 is set such that they bend inwards and towards each other as illustrated in FIG. 8. In some methods, a guidewire or a catheter such as steerable catheter can be inserted between the distal locking tabs 256, and the distal locking tabs 256 can be pushed out against the hub 258. The hub 258 is designed with matching pockets 260 such that the distal locking tabs 256 fit into these pockets 260. As long as the steerable catheter is present to force the distal locking tabs 256 outwards into the pockets 260, the tip of the delivery catheter 252 remains locked to the hub 258. Other locking mechanisms are possible. The anchor 254 can be configured to complement other tools. The tools can include locking tabs 256 as shown. The tool can include one or more locking tabs 256. The anchor 254 can include complementary releasable connector as shown which engages the locking tabs 256. The hub 258 can be proximal to a helical screw-type anchor. The hub 258 may have features such as windows which can lock the locking tabs 256 of the tool.

In some embodiments, the tissue can be welded, heat treated, or otherwise adapted to change the tissue properties. In some methods, the tissue is altered to firm up the tissue. In some methods of use, the tissue is altered to prevent undesired anchor pull-out effects. In some embodiments, tissue fixation mechanisms can include magnets, adhesives (e.g., cyanoacrylates or UV light activated adhesives, for example), or fixation features akin to a gecko/lizard's foot.

Figure 9:
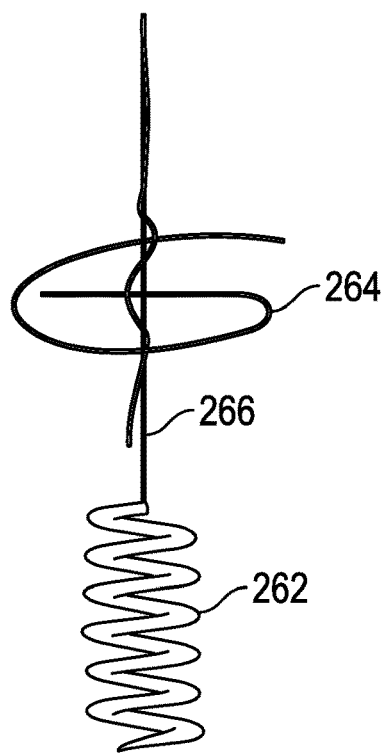
FIG. 9 illustrates an embodiment of an anchor with a clip.

FIG. 9 illustrates an embodiment of an anchor 262 and a clip 264. The anchor 262 can be coupled to a suture 266 as described herein. The clip 264 can be disposed on the suture 266. In some embodiments, the clip 264 can be movable along the suture 266. The clip 264 can be moved from a proximal direction to a distal direction, toward the anchor 262. The clip 264 can comprise a shape memory material. The shape memory material can be nitinol. The clip 264 can have a pre-formed shape similar to a paper clip. The clip 264 can inhibit movement of an implant such as a coaptation assist device 212. The implant (not shown) can be placed between the clip 264 and the anchor 262. The position of the clip 264 can prevent further proximal movement of the implant. The clip 264 can comprise wires formed to hold onto a suture. Shown distally is an anchor 262, which can be a helical-type or other anchor configured to engage tissue.

Figure 10:
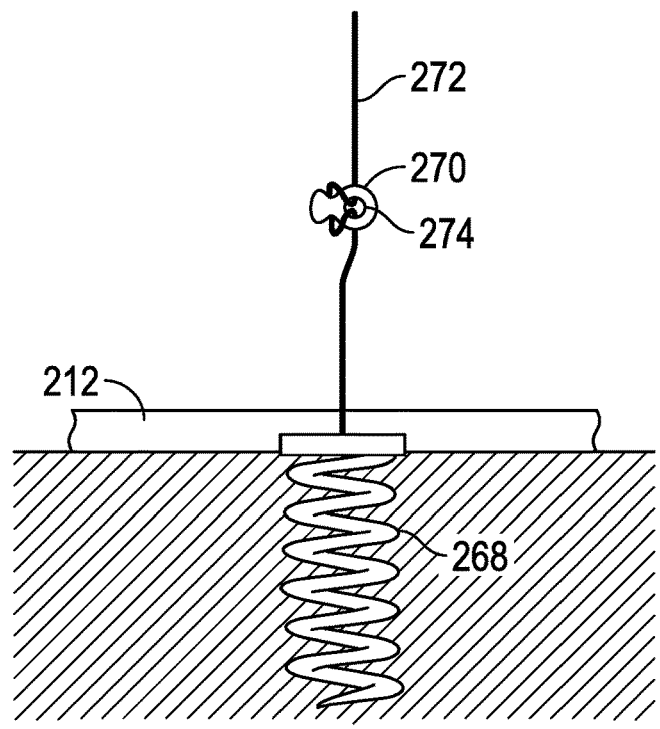
FIG. 10 illustrates an embodiment of an anchor with a clip.

FIG. 10 illustrates an embodiment of an anchor 268 and a clip 270. The anchor 268 can be coupled to a suture 272 as described herein. The clip 270 can be disposed on the suture 272. In some embodiments, the clip 270 can be movable along the suture 272. The clip 270 can be moved from a proximal direction to a distal direction, toward the anchor 268. The clip 270 can inhibit movement of an implant such as a coaptation assist device 212. The implant (not shown) can be placed between the clip 270 and the anchor 268. The position of the clip 270 can prevent further proximal movement of the implant. The clip 264 can comprise an eyelet 274. The suture 272 is threaded through an eyelet 274. In some methods of use, the clip 264 is slid down the suture 272. In some methods of use, the clip 264 is designed to couple an implant with the anchor 268. The clip 264 is slid distally to hold the implant to the anchor 268. The anchor 268 can be a helical-type or other anchor configured to engage tissue, as described herein. The anchor 268 can be operably connected to a tether, such as the suture 272 shown. The clip 270 can be movable, such as slidable, along at least part of the length of the suture 272. The movement of the clip 270 can lock fabric or other feature of the implant to the anchor 268.

Figure 11A:
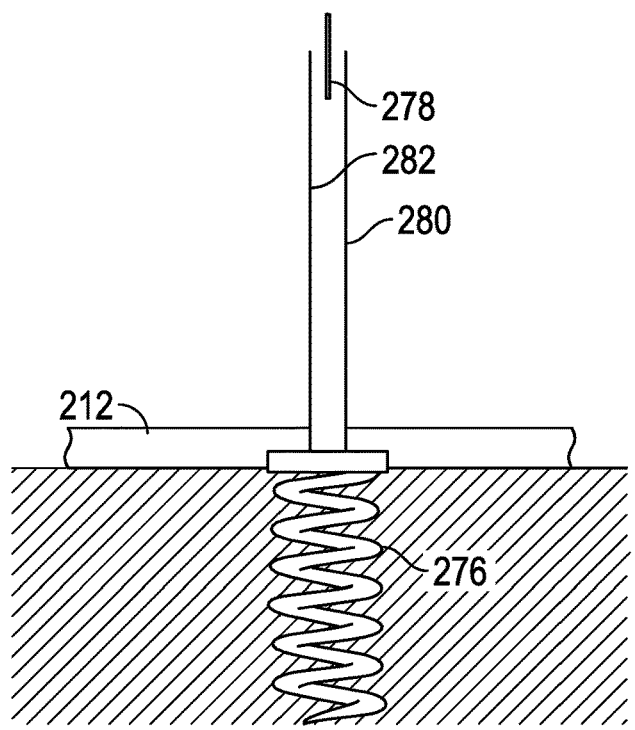
FIGS. 11A-11B illustrate an embodiment of an anchor with a clip.
Figure 11B:
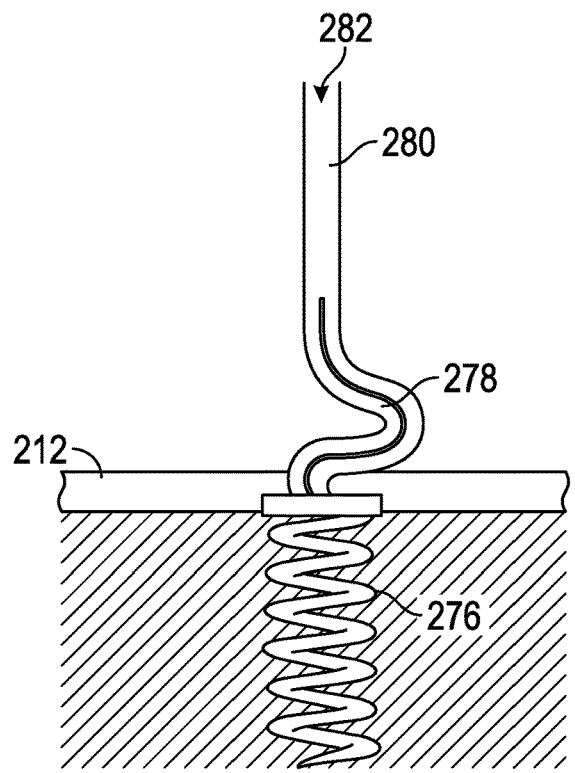

FIGS. 11A-11B illustrate an embodiment of an anchor 276 and a clip 278. The anchor 276 can be coupled to a suture 280 as described herein. The clip 278 can be disposed within the suture 280. In some embodiments, the clip 278 can be movable within the suture 280. The clip 278 can be moved from a proximal direction to a distal direction, toward the anchor 276. The clip 278 can comprise a shape memory material. The shape memory material can be nitinol. The clip 278 can inhibit movement of an implant such as a coaptation assist device 212. The position of the clip 278 can prevent further proximal movement of the implant. The clip 278 can comprise shape memory material, such as nitinol for example. The clip 278 can be configured to slide as shown in FIGS. 11A-11B. FIG. 11A shows the clip 278 is a first configuration. The anchor 276 can be coupled with a tether, such as a hollow braided suture 280, with a lumen 282 therethrough. The lumen 282 can be configured to fit the clip 278 in the first configuration, which is shown to be in the shape of a wire. The clip 278 can be slid into place relative to the anchor 276. In some methods of use, application of energy, such as electrical current, electromagnetic energy, thermal energy, or the like can transform the clip 278 from the first linear configuration to the second non-linear (e.g., curved, or knot-like) configuration. In the second configuration, the clip 278 can secure the implant such as the coaptation assist device 212 to the anchor 276 as illustrated in FIG. 11B.

Figure 12:
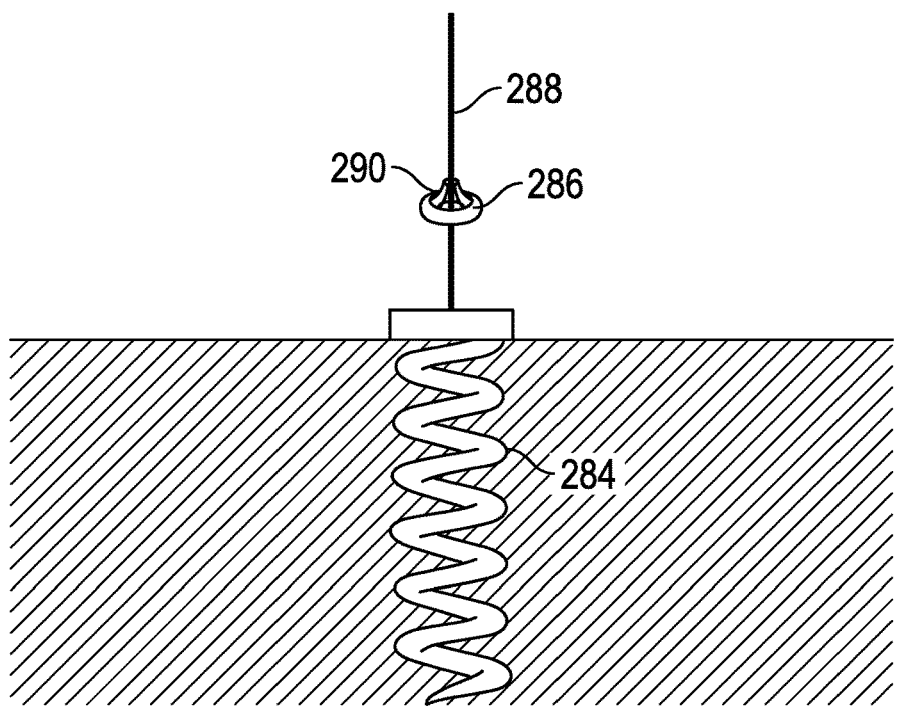
FIG. 12 illustrates an embodiment of an anchor with a clip.

FIG. 12 illustrates another embodiment of an anchor 284 and a clip 286. The anchor 284 can be coupled to a suture 288 as described herein. The clip 286 can be disposed on the suture 288. In some embodiments, the clip 286 can be movable along the suture 288. In some embodiments, the clip 286 is moveable in only one direction. The clip 286 can be moved from a proximal direction to a distal direction, toward the anchor 284. The clip 286 can inhibit movement of an implant such as a coaptation assist device 212. The implant (not shown) can be placed between the clip 286 and the anchor 284. The position of the clip 286 can prevent further proximal movement of the implant. In some embodiments, the suture 288 could be another structure such as a plurality of tie-like arms, a threaded rod, hook-and-loop fastener arms, and the like. The clip 286 can include leaf springs 290 operably connected to the suture 288 and configured to grab onto the suture 288. In some embodiments, the clip 286 can be integrated into the implant, such as the coaptation assist device 212. In other embodiments, the clip 286 is a separate component.

Figure 13:
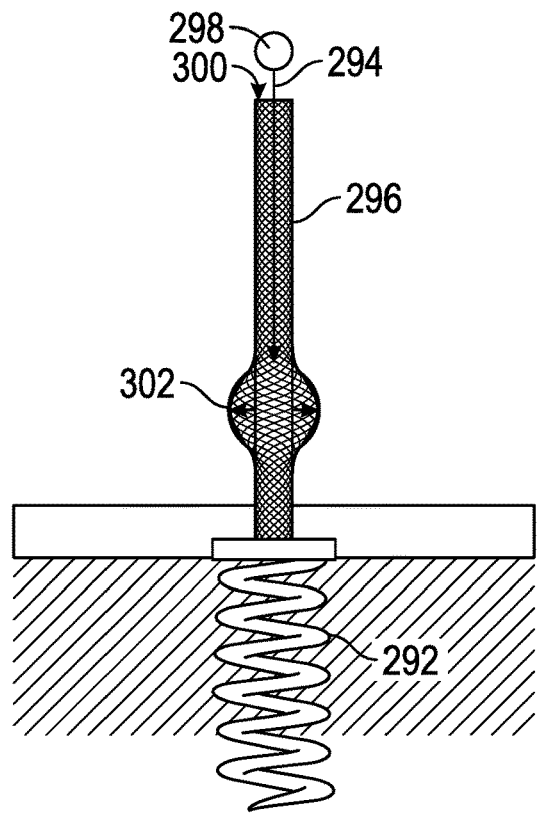
FIG. 13 illustrates an embodiment of an anchor with a clip.

FIG. 13 illustrates yet an embodiment of an anchor 292 and a clip 294. The anchor 292 can be coupled to a suture 296 as described herein. The clip 294 can be disposed within the suture 296. In some embodiments, the clip 294 can be movable within the suture 296. The clip 294 can be moved from a proximal direction to a distal direction, toward the anchor 292. The clip 294 can comprise a ball 298. The clip 294 can inhibit movement of an implant such as a coaptation assist device 212. The position of the clip 294 can prevent further proximal movement of the implant. The clip 294 can be configured to slide as shown by the arrow. The anchor 292 can be coupled with a tether, such as a hollow braided suture 296, with a lumen 300 therethrough. The lumen 300 can be configured to fit the clip 294. The hollow tube 269 can have at least a portion with a flexible sidewall 302 as shown. The lumen 300 can be sized to accept or house the ball 298. The ball 298 can be moved within the lumen 300 to a position in which the sidewall 302 radially expands by virtue of the diameter of the ball 298, such that the ball 298 and suture 296 combination form a lock.

Figure 14:
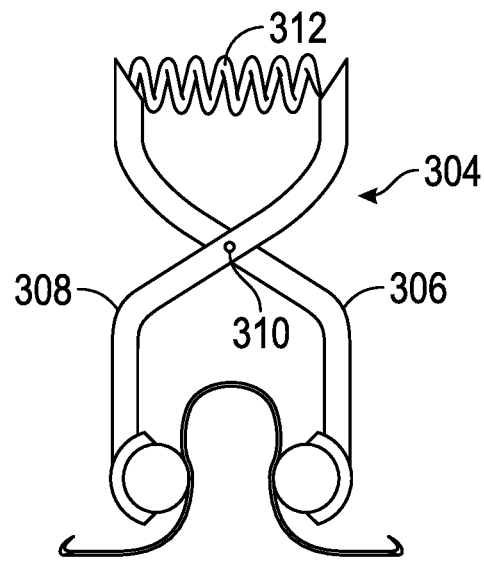
FIG. 14 illustrates an embodiment of an anchor.

FIG. 14 illustrates an embodiment of an anchor 304. The anchor 304 can be an activated biopsy-type clamp. The anchor 304 can include a plurality of lever arms, such as two lever arms 306, 308. The lever arms 306, 308 can intersect at a fulcrum point 310 as shown. The anchor 304 can include a spring element 312. The anchor 304 can grab onto tissue in between the two lever arms 306, 308. The anchor 304 can grab onto an implant such as the coaptation assist device 212 (not shown) in between the two lever arms 306, 308.

Figure 15:
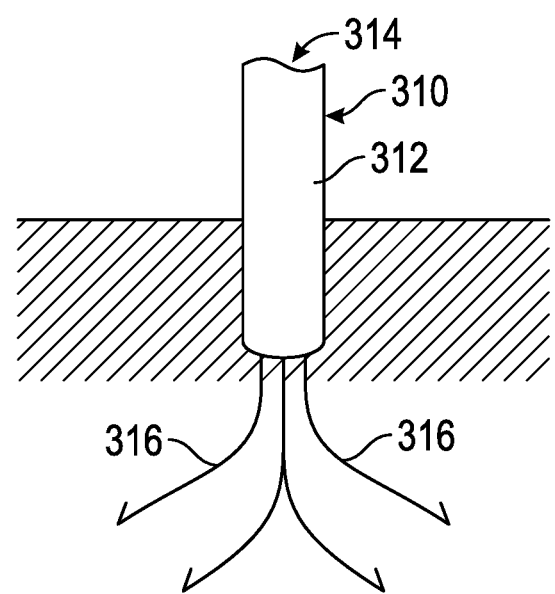
FIG. 15 illustrates an embodiment of an anchor.

FIG. 15 illustrates an embodiment of an anchor 310. The anchor 310 can be a multi-stage grapple or treble hook anchoring device. The device can include a tubular body 312 configured to be inserted into tissue. The tubular body can include a lumen 314. The lumen 314 can include with one, two, three, four, or more secondary arms 316. The secondary arms 316 can be in a first linear configuration within the tubular body 312. The secondary arms 316 can be moved distally outside of the tubular body 312 such that they spread out (e.g., radially outwardly) to grip tissue as illustrated. The secondary arms 316 can include sharpened points. The secondary arms 316 can be coupled to each other.

Figure 16:
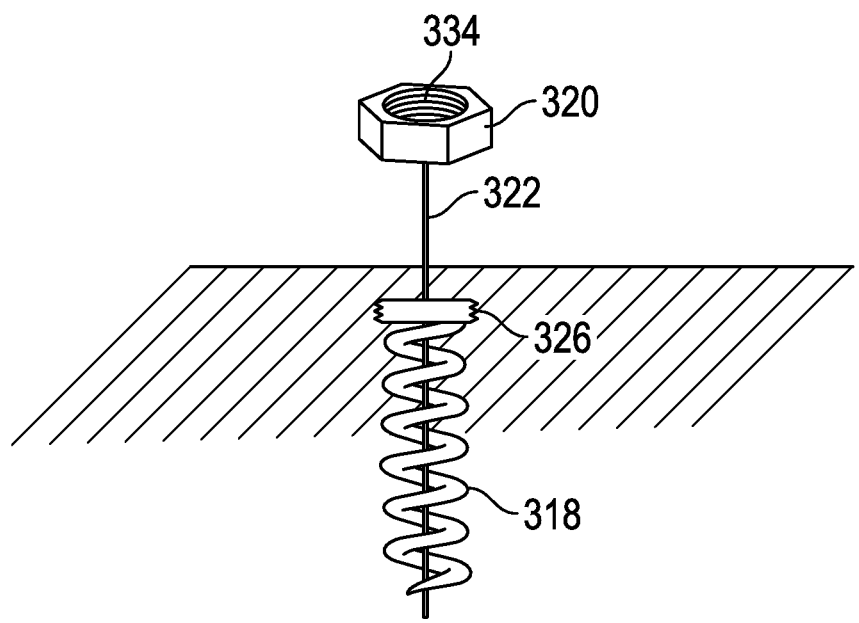
FIG. 16 illustrates an embodiment of an anchor with a clip.

FIG. 16 illustrates an embodiment of an anchor 318 and a clip 320. The anchor 318 can be coupled to a suture 322 as described herein. The clip 320 can be disposed on the suture 322. In some embodiments, the clip 320 can be movable along the suture 322. The clip 320 can be moved from a proximal direction to a distal direction, toward the anchor 318. The clip 320 can inhibit movement of an implant such as a coaptation assist device 212. The implant (not shown) can be placed between the clip 320 and the anchor 318. The position of the clip 320 can prevent further proximal movement of the implant. The clip 320 can comprise a threaded lumen 324. The anchor 318 can include a hub 326. The hub 326 can be threaded to engage the threaded lumen 324. In some methods of use, the clip 320 is rotated to engage the hub 326. The clip 320 is rotated distally to hold the implant to the anchor 318. The anchor 318 can be a helical-type or other anchor configured to engage tissue, as described herein. The suture 322 can be a tether, guidewire, or rail. FIG. 16 illustrates an embodiment of a clip 320 that can be placed over a suture 322. The clip 320 can be operably connected to an implant (not shown).

Figure 17:
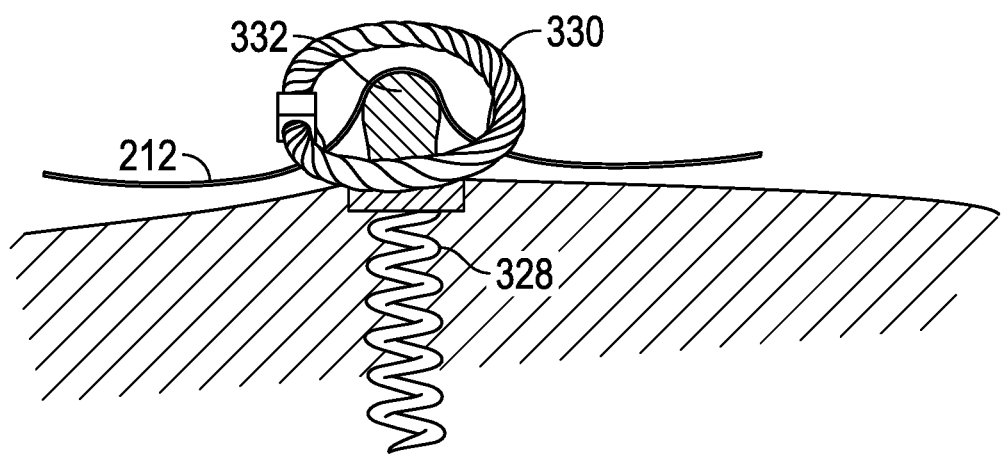
FIG. 17 illustrates an embodiment of an anchor with a clip.

FIG. 17 illustrates an embodiment of an anchor 328 and a clip 330. The anchor 328 can include a knob 332. The clip 330 can be disposed over the knob 332. The clip 330 can be moved from a proximal direction to a distal direction, toward the anchor 328. The clip 330 can inhibit movement of an implant such as a coaptation assist device 212. The coaptation assist device 212 can be placed between the clip 330 and the knob 332. The position of the clip 330 can prevent further proximal movement of the coaptation assist device 212. FIG. 17 illustrates a clip 330 including a grommet, having an outer rim and an inner eyelet as shown. The grommet can snap over the knob 332 or other structure of the anchor 328. The clip 330 can be used in order to secure the implant to the anchor 328 as shown.

Figure 18A:
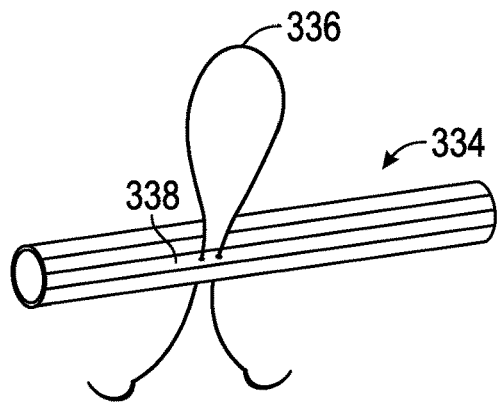
FIGS. 18A-18D illustrates an embodiment of an anchor.
Figure 18B:
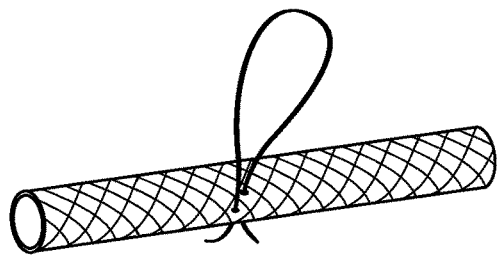
Figure 18C:
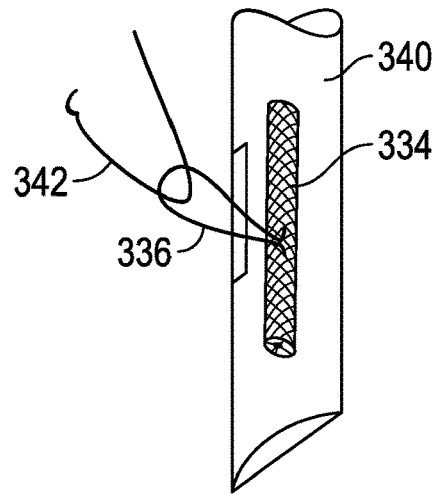
Figure 18D:
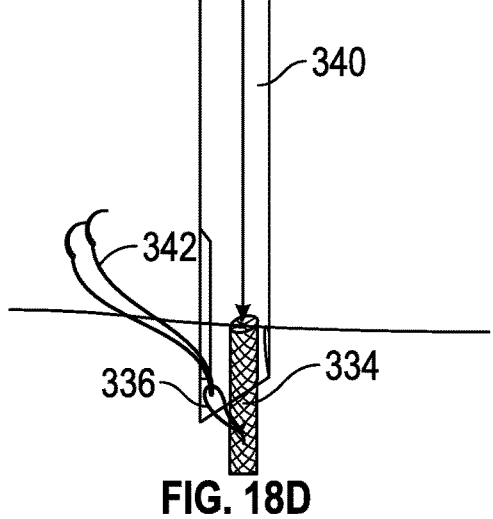

FIGS. 18A-18D illustrates an embodiment of an anchor 334. The anchor 334 is a combination of an anchor and a clip. The combination can be formed of a shape memory material such as nitinol. As illustrated, a suture 336 can be threaded through a slot 338 in the anchor 334 such that a loop is formed as shown in FIG. 18A. In some embodiments, the anchor 334 is twisted as shown in FIG. 18B. In some embodiments, the anchor 334 has a first configuration shown in FIG. 18A. In some embodiments, the anchor 334 has a second configuration shown in FIG. 18B. When the anchor 334 is twisted, the suture 336 can be more tightly held by the anchor 334. The anchor 334 can be loaded into a needle-like introducer 340 as shown in FIG. 18C. The introducer can have features of other tools described herein. In some embodiments, another suture 342 is threaded through a loop. Using a pushing mechanism, for example, the anchor 334 can be released into tissue as shown in FIG. 18D. The anchor combination can further engage in tissue if it is untwisted, rotated, or the like.

Figure 19:
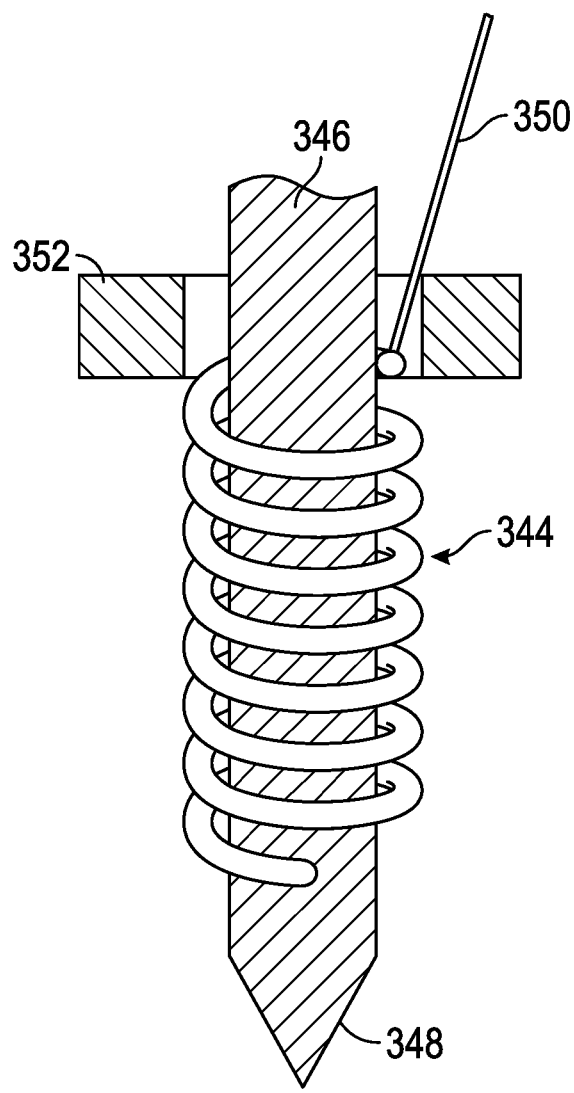
FIGS. 19A-19B illustrates an embodiment of an anchor.
Figure 19B:
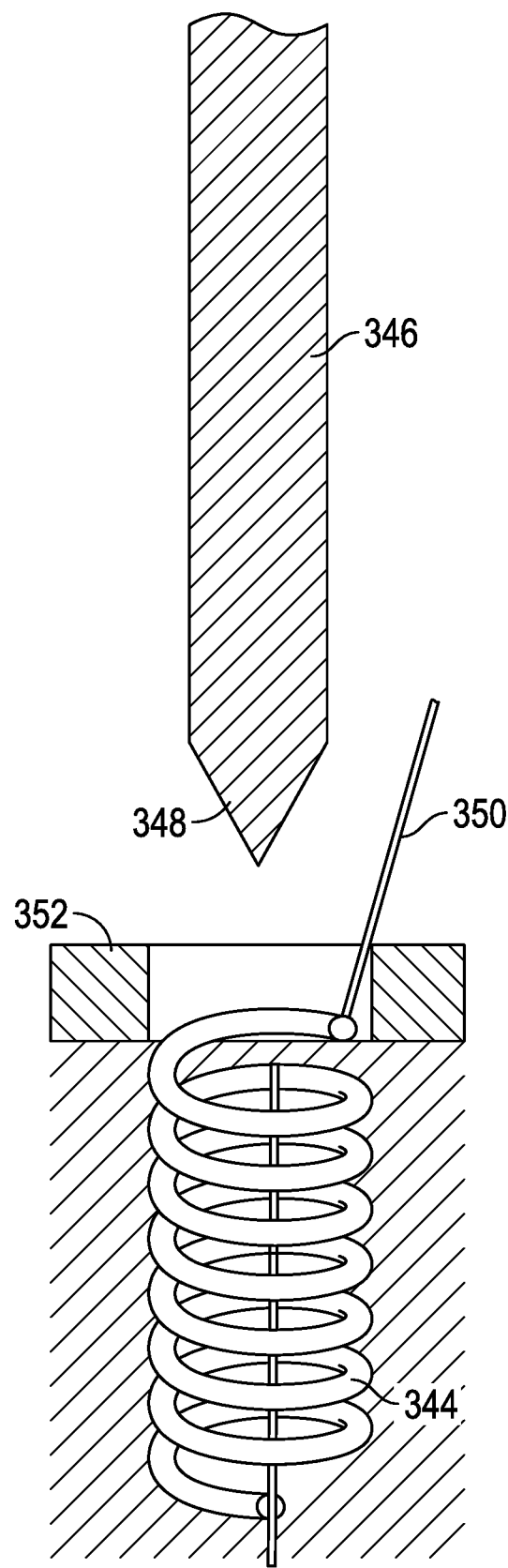

FIGS. 19A-19B illustrate an embodiment of an anchor 344. The anchor 344 can include a helical shape, as shown. A needle 346 with a sharpened distal end 348 can be used to more easily insert the helix portion of the anchor 344 into tissue. The anchor 344 does not necessarily need to be rotated, such as helical screw anchors. Rather, the embodiment shown in FIGS. 19A-19B can be pushed or driven straight into tissue. The anchor 344 can be removably connected to the needle 346. In the illustrated embodiment, the needle 346 passes through the center of, and be radially surrounded by the anchor 344. The anchor 344 can be coupled with a tether, such as a suture 350. The anchor 344 can include a proximal shoulder 352 configured to spread the load over a larger surface area. The anchor 344 need not necessarily helical and can be another interfering geometry sufficient to maintain its position within tissue following needle retraction.

Figure 20A:
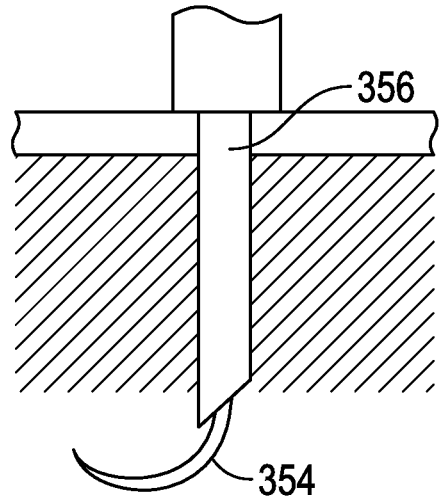
FIGS. 20A-20B illustrates an embodiment of an anchor.
Figure 20B:
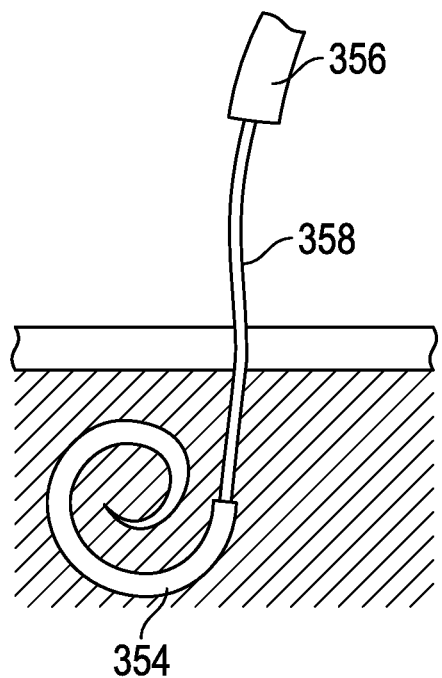

FIGS. 20A-20B illustrate an embodiment of an anchor 354. The anchor 354 can comprise a shape-set shape memory material. The material can be nitinol. In some embodiments, the anchor 354 is deliverable from an inner lumen of a needle or introducer 356 as shown in FIG. 20A. The needle 356 can be advanced distally below the tissue surface, as shown. In some embodiments, a pusher can be used to expose the anchor 354. The anchor 354 can assume the shape-set (e.g., assumes a curved configuration) to be retained within the tissue as shown in FIG. 20B. The proximal end of the anchor 354 can be operably connected to a tether, such as a suture 358. The pusher and needle 356 can then be retracted once the anchor 354 is retained within the tissue.

Figure 21:
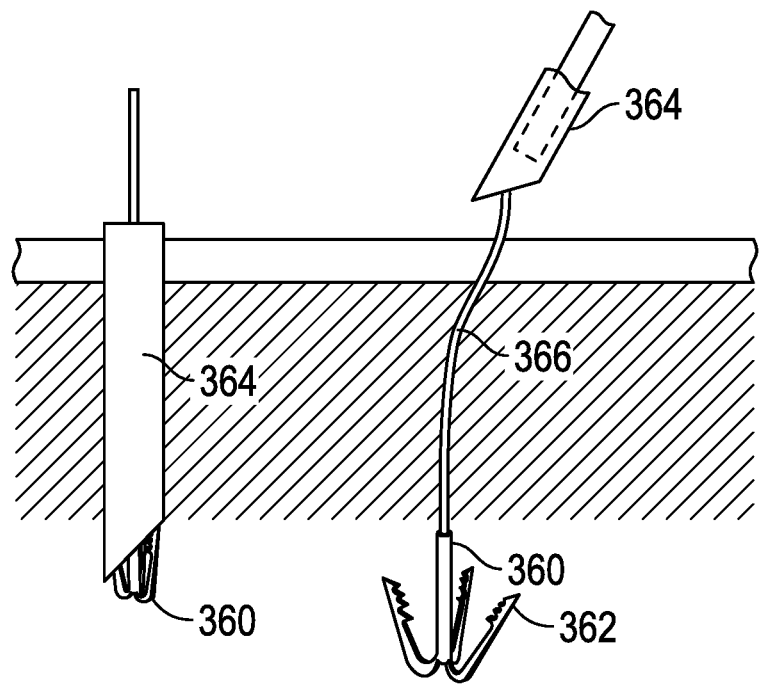
FIG. 21 illustrates an embodiment of an anchor.

FIG. 21 illustrates another embodiment of an anchor 360. The anchor 360 of FIG. 21 can be similar to the anchor of FIG. 5A. The anchor 360 can take the configuration of a barbed structure, such as basket or umbrella when delivered into the tissue. The anchor 360 can include a plurality of distal barbs or hooks 362. The anchor 360 can have a first configuration within an introducer 364. The anchor 360 can have a second configuration when deployed from the introducer 364. The anchor 364 can be coupled to a suture 366. The anchor 360 can comprise a shape memory material or other suitable material. The material can be nitinol.

Figure 22A:
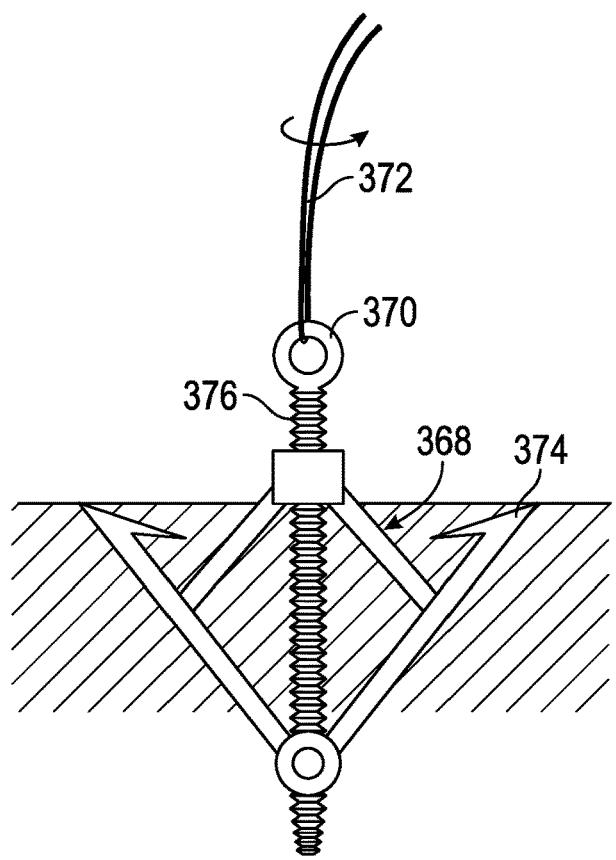
FIGS. 22A-22B illustrates an embodiment of an anchor.
Figure 22B:
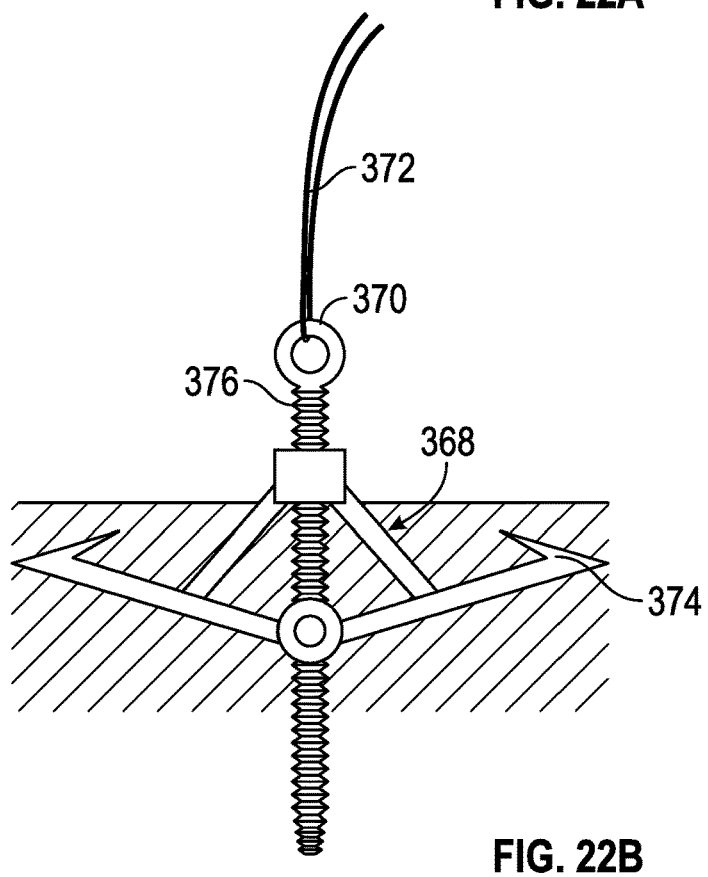

FIGS. 22A-22B illustrate an embodiment of an anchor 368. The anchor 368 can include a toggle bolt. The anchor 368 can include a proximal eyelet 370. The eyelet 370 can be operably connected to a suture 378. The anchor 368 can include barbs 374 that can radially expand when within the tissue. The anchor 368 includes a toggle bolt 376 longitudinal axis. The anchor 368 is inserted within the tissue as shown in FIG. 22A. After the anchor 368 is inserted into tissue, the toggle bolt 376 and/or the eyelet 370 can be rotated. The barbs 374 are pushed outward, further securing the anchor 368 in the tissue as shown in FIG. 22B.

FIGS. 23A-23E illustrate an embodiment of an arrangement of clips 378, 380 according to some methods of use. In some arrangements, two clips 378, 380 are placed next to each other to increase the surface area of the lock. This can reduce the number of clips 378, 380. In some embodiments, increasing the surface area of the clip 378, 380 can potentially reduce the numbers of anchors 382 needed. In some embodiments, 2, 3, 4, 5, or more clips can be placed in close proximity to each other, such as directly adjacent to each other as illustrated. In some embodiments, one clip 378 spans two or more anchors 382, 384 as shown in FIG. 23E.

Figure 24A:
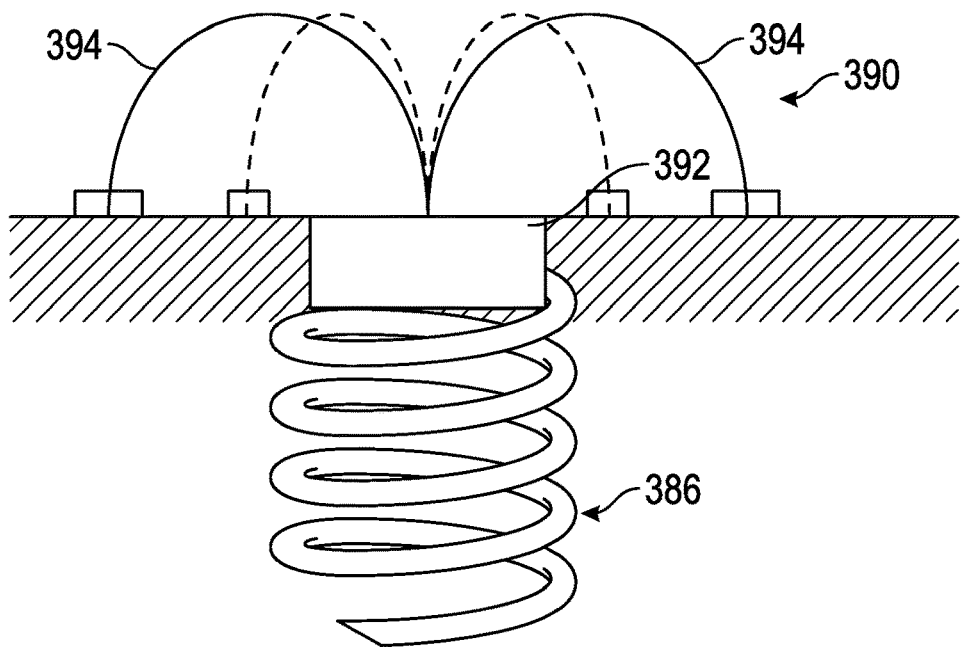
FIGS. 24A-24E illustrates embodiments of anchors.

FIG. 24A illustrates an embodiment of an anchor 386. The anchor 386 can be a helical-type or other anchor configured to engage tissue. The anchor 386 can include a reinforcement portion 390. The reinforcement portion 390 can advantageously reduce the risk of anchor pull-out and embolization. In some embodiments, the anchor 386 includes a helical or other anchor configured to reside within the tissue as described herein. The anchor 386 can include a hub 392. The hub 392 can be in the shape of a disc. The hub 392 can be operably attached to the anchor 386 as shown. In the embodiment shown in FIG. 24A, operably connected to the hub 392 can be one, two, or more shape memory clips 394. The shape memory material can be nitinol. The clips 394 can increase the surface area that the anchor 386 engages.

Figure 24B:
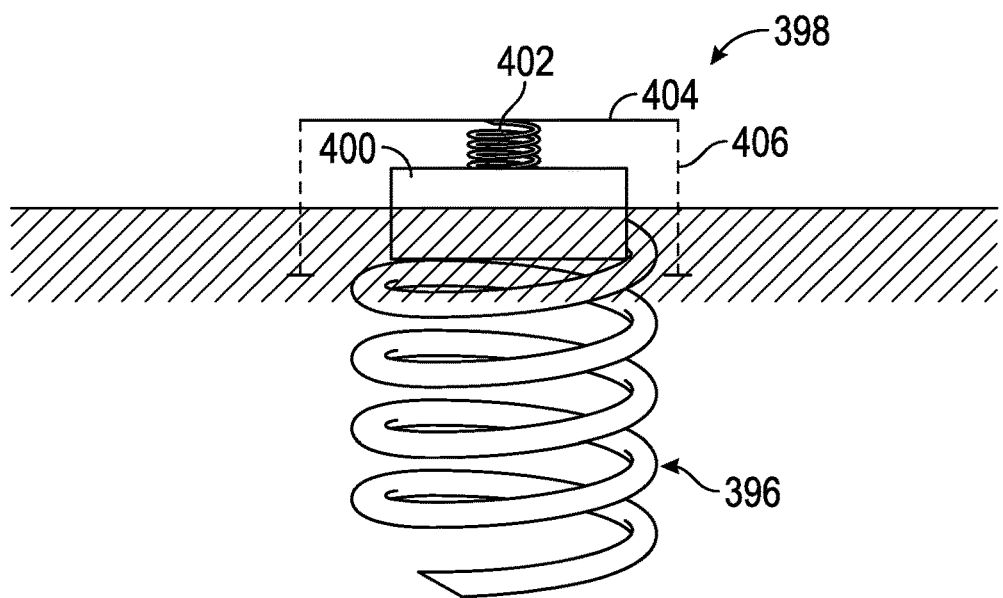

FIG. 24B illustrates an embodiment of an anchor 396. The anchor 396 can be a helical-type or other anchor configured to engage tissue. The anchor 396 can include a reinforcement portion 398. The reinforcement portion 398 can advantageously reduce the risk of anchor pull-out and embolization. In some embodiments, the anchor 396 includes a helical or other anchor configured to reside within the tissue as described herein. The anchor 396 can include a hub 400. The hub 400 can be in the shape of a disc. The hub 400 can be operably attached to the anchor 396 as shown. As illustrated in FIG. 24B, the anchor 396 can include a spring 402. The spring 402 can be located in between a surface of the hub 400 and a proximal cap 404. The proximal cap 404 can include a T or treble hook 406 designed to engage tissue. The hook can include a barb 408 to increase engagement with the tissue.

Figure 24C:
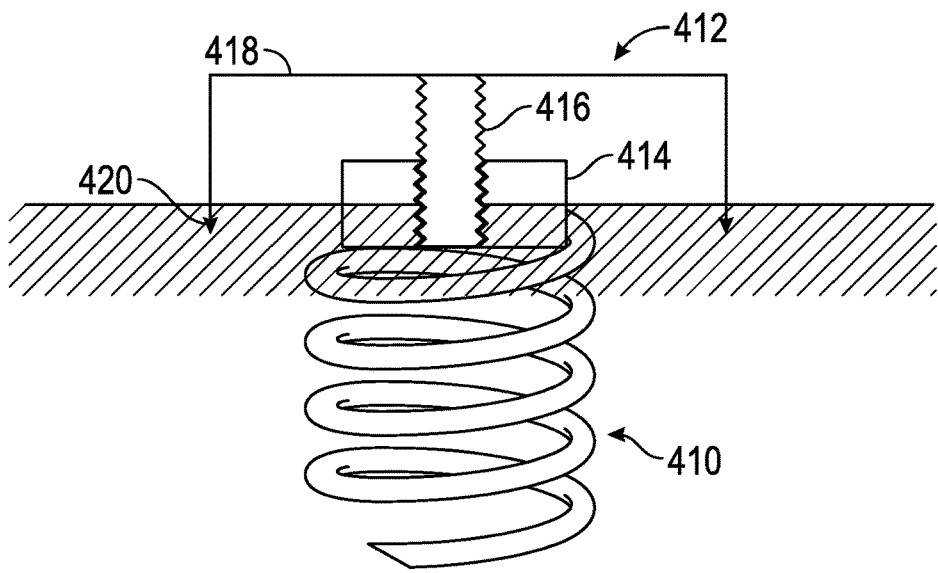

FIG. 24C illustrates an embodiment of an anchor 410. The anchor 410 can be a helical-type or other anchor configured to engage tissue. The anchor 410 can include a reinforcement portion 412. The reinforcement portion 412 can advantageously reduce the risk of anchor pull-out and embolization. In some embodiments, the anchor 410 includes a helical or other anchor configured to reside within the tissue as described herein. The anchor 410 can include a hub 414. The hub 414 can be in the shape of a disc. The hub 414 can be operably attached to the anchor 410 as shown. In FIG. 24C, the hub 414 can have a barbed feature 416. The barbed feature 416 can be located in between the hub 414 and a proximal cap 418. The barbed feature 418 can be located centrally. The anchor 410 can press against tissue with either the T/treble hook feature 420 extending from the cap 418.

Figure 24D:
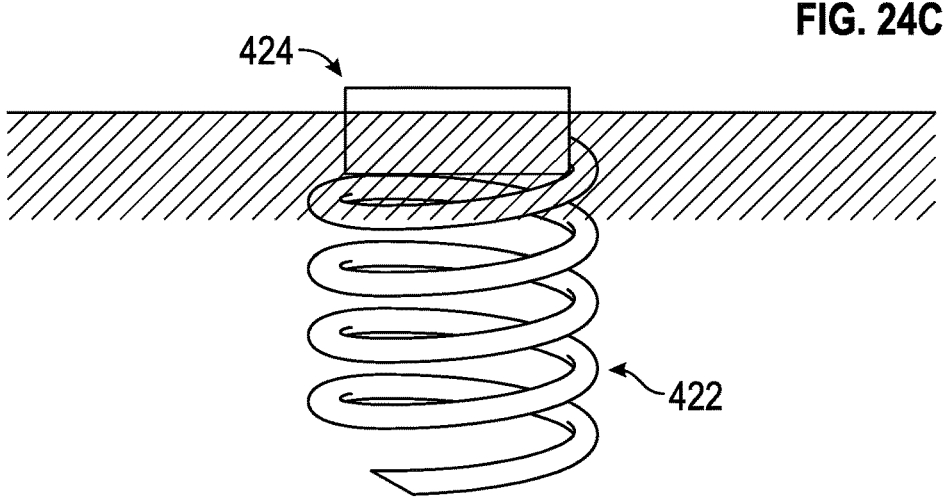

FIG. 24D illustrates an embodiment of an anchor 422. The anchor 422 can be a helical-type or other anchor configured to engage tissue. The anchor 422 can include a reinforcement portion 424. The reinforcement portion 424 can advantageously reduce the risk of anchor pull-out and embolization. In some embodiments, the anchor 422 includes a helical or other anchor configured to reside within the tissue as described herein. The anchor 422 can include a hub 424.

The hub 424 can be in the shape of a disc. The hub 424 can be operably attached to the anchor 422 as shown. the method of use can include the application of energy. Energy, such as RF, microwave, or other energy is utilized to create a bond between the tissue and the hub. In some embodiments, a biocompatible adhesive, such as a cyanoacrylate for example, is utilized to bond the hub and the tissue.

Figure 24E:
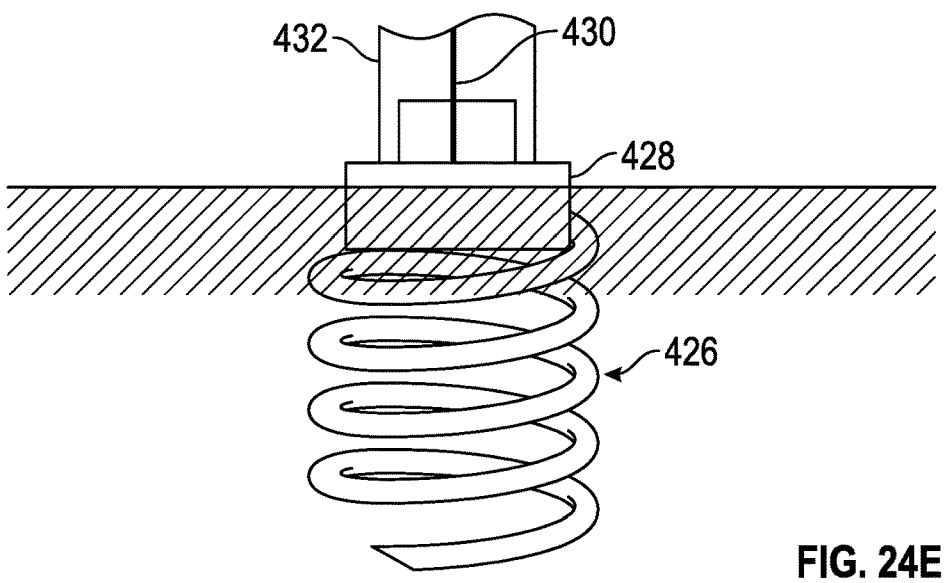

FIG. 24E illustrates an embodiment of an anchor 426. The anchor 426 can be a helical-type or other anchor configured to engage tissue. The anchor 426 can include a reinforcement portion 428. The reinforcement portion 428 can advantageously reduce the risk of anchor pull-out and embolization. In some embodiments, the anchor 426 includes a helical or other anchor configured to reside within the tissue as described herein. The anchor 426 can include a hub 428. The hub 428 can be in the shape of a disc. The hub 428 can be operably attached to the anchor 426 as shown. In FIG. 24E, the hub 428 includes a suture 430 or wire extending proximally. The anchor 426 can include a crimp feature 432 to promote stabilization of the anchor.

Figures 25A, 25B, 25C:
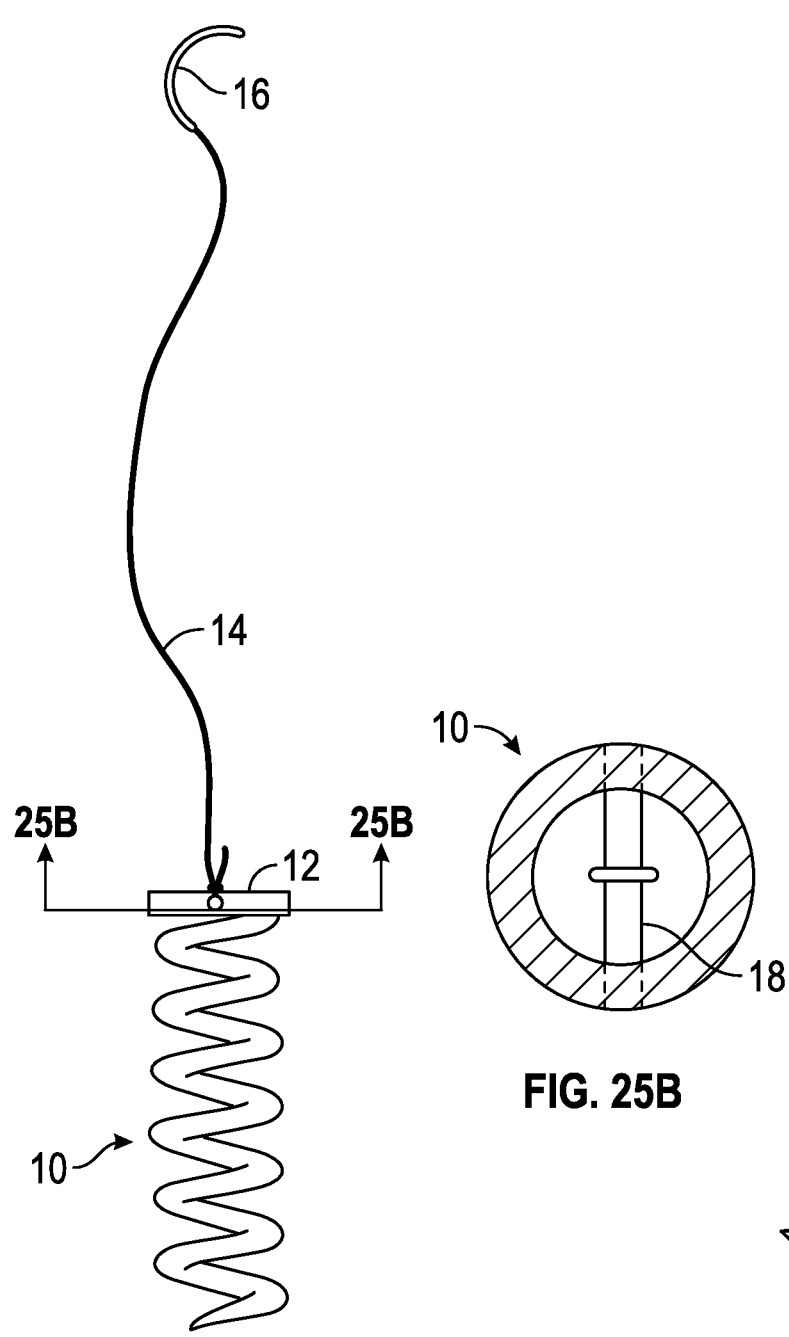
FIGS. 25A-25C illustrates embodiments of an anchor and a suture.

FIGS. 25A-25C illustrate embodiments of an anchor and a suture. In some embodiments, the anchor 10 includes a helical or other anchor configured to reside within the tissue. In other embodiments, the anchor can take the form of any anchor as described herein. The anchor can include a proximal hub 12. The hub 12 can be connected to a tether, such as an end of the tether. The tether can be a suture 14 having a needle 16, as shown. In other embodiment, the tether is a tube, rail, or guidewire. The anchor can include a cross pin 18. The cross-section 25B-25B illustrates a cross pin 18 in the hub 12. The suture 14 can be operably attached to the cross pin 18.

Also illustrated is an alternative embodiment shown in FIG. 25C. In some embodiments, the anchor 434 includes a grappling hook. The grappling hook has a plurality of arms 436. In the illustrated embodiment, three arms 436 are shown but one or more arms are contemplated. The arms 436 can serve as a tissue anchor instead of the helical structure shown in other embodiments herein.

FIGS. 26A-26D illustrate an embodiment of an anchor driver 20. The anchor driver 20 can include a proximal control handle 22. The proximal control handle 22 can include a torque knob 24 and a suture locking knob 26. The torque knob 24 can control a torque shaft 28. The anchor driver 20 can include a distal tubular body 30 sized to accept the torque shaft 28 therein. The torque shaft 28 can be configured to rotate an anchor, as described herein. Rotation of the anchor may be necessary to lodge the anchor within tissue. In other embodiments, a pusher described herein is used to expel the anchor from the anchor driver 20.

Figure 26C:
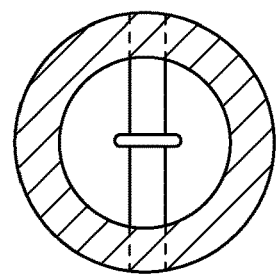
FIGS. 26A-26D illustrates an embodiment a tool for use with the anchor and a suture of FIG. 25A.
Figure 26A:
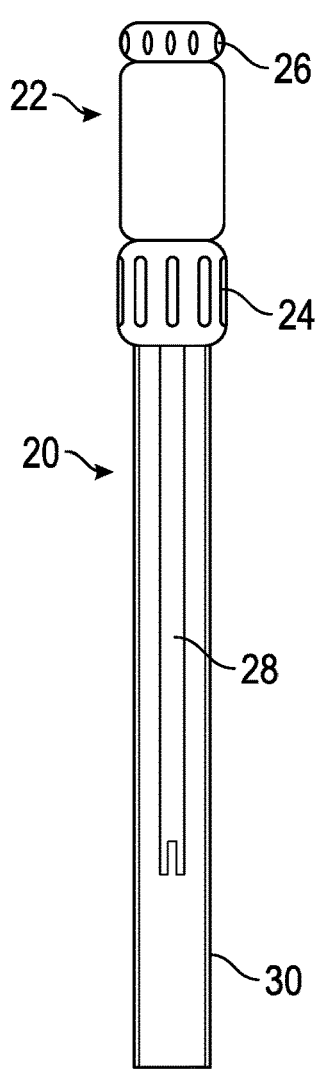
Figure 26B:
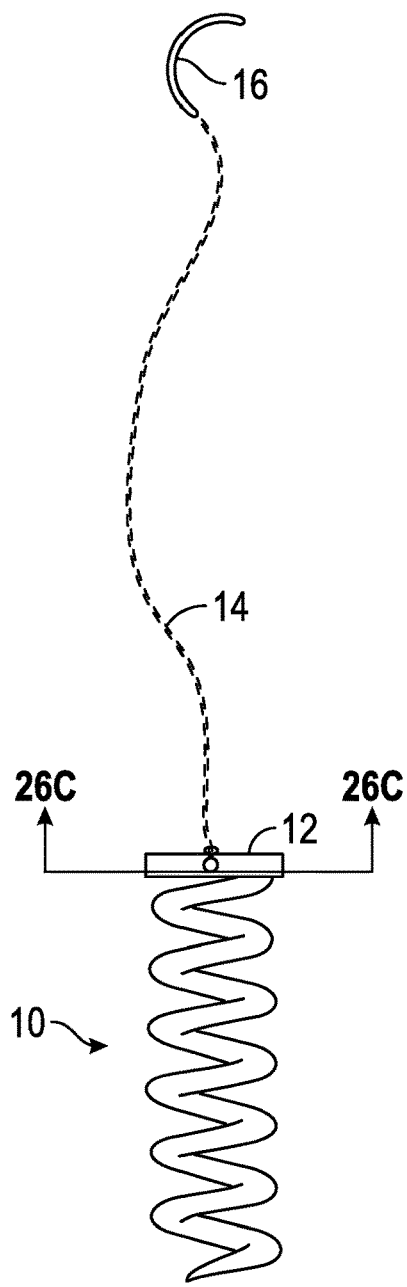
Figure 26D:
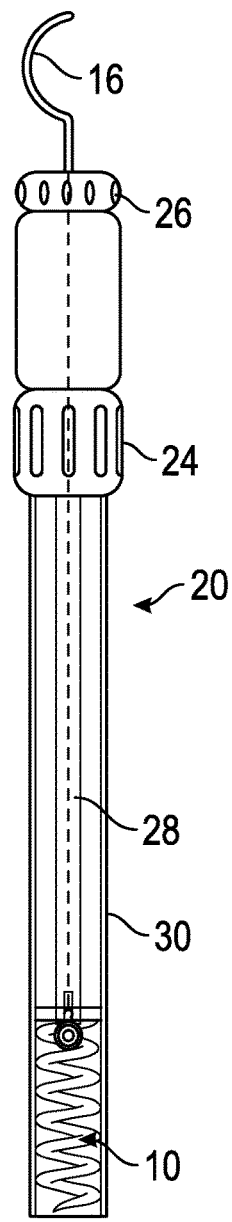

Also illustrated is the anchor 10. In some embodiments, the suture 14 can be attached to the anchor 10 via a knot. In some embodiments, an end of the suture 14 can be heat-formed like a ball. The anchor 10 can be loaded into the anchor driver 20 as illustrated. In some embodiments, the torque driver 20 engages a feature of the anchor 10. As described herein, the torque driver 20 can engage the crossbar 18 of the anchor 10. The anchor 10 can be initially retracted inside the tubular body 30 as shown in FIG. 26C.

Rotating the torque knob 24 in an appropriate direction can rotate the torque driver 28. Rotating the torque driver 28 can rotate the anchor 10 in order to engage or disengage the anchor 10 from the tissue. The suture locking knob 28 can help to maintain the anchor 10 in place during anchor delivery. In some methods, the suture 14 is pulled through the suture locking knob 28. Tension on the suture 14 can hold the anchor 10 against the torque driver 28. Tension on the suture 14 can engage the crossbar 18 with the torque driver 28. Other configurations of coupling the anchor 10 to the torque driver are contemplated.

Figure 27:
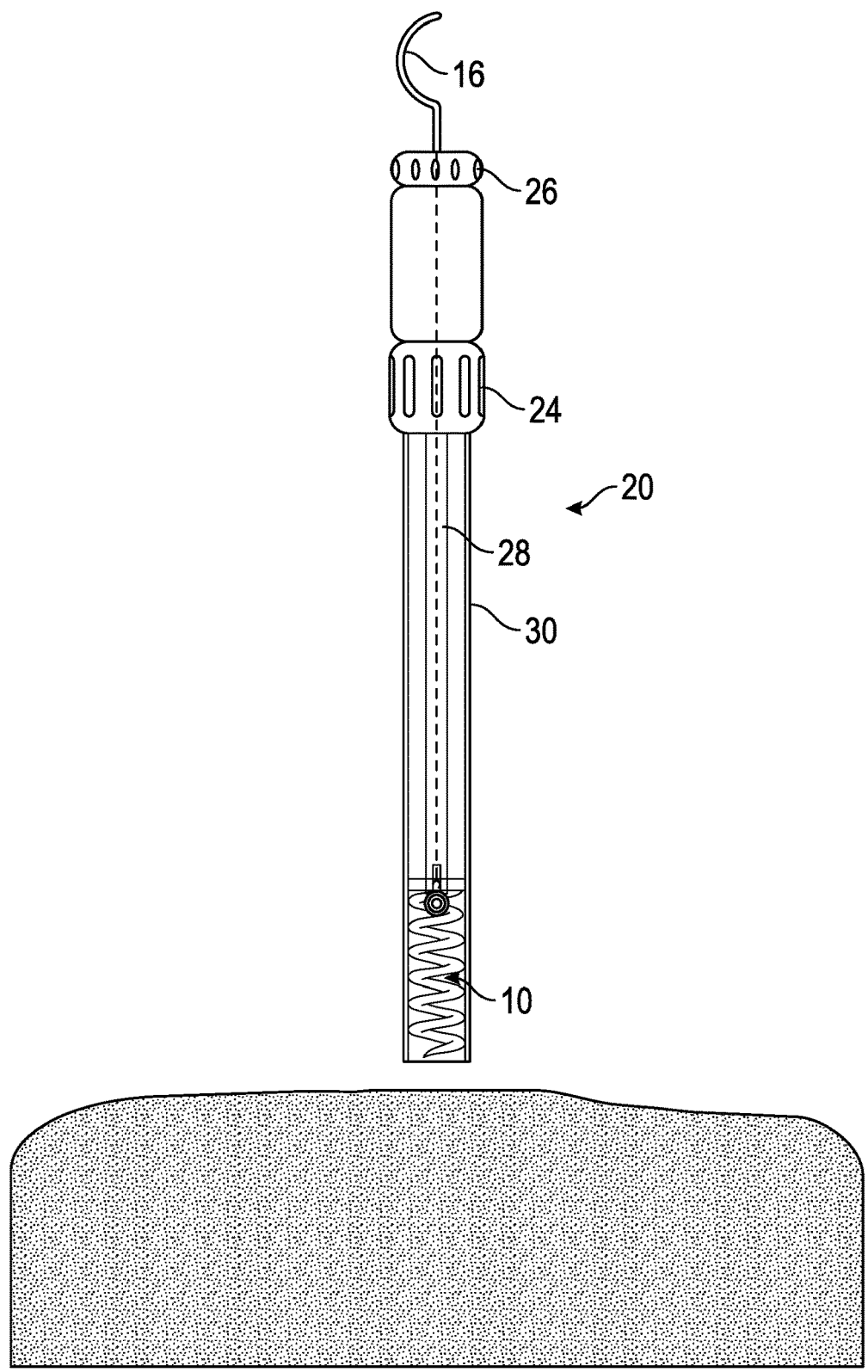
FIG. 27 illustrates a method step in some methods of use of the anchor and a suture of FIG. 25A.

FIGS. 27-31 illustrate method steps for some methods of use of the anchor 10 and the anchor driver 20. FIG. 27 illustrates the anchor driver 20 approaching the tissue. In some embodiments, the tissue is cardiac tissue having endocardial, myocardial, and epicardial layers. In other embodiments, the tissue is associated with other organs or anatomical structures such as the bladder, intestine, lungs, stomach, kidneys, liver, skin, gall bladder, pancreas, brain, spinal cord, bone, muscle, fascia, ligaments, tendons, cartilage, etc. The anchor 10 is initially retracted within the distal tubular body 30 as shown in FIG. 27.

Figure 28:
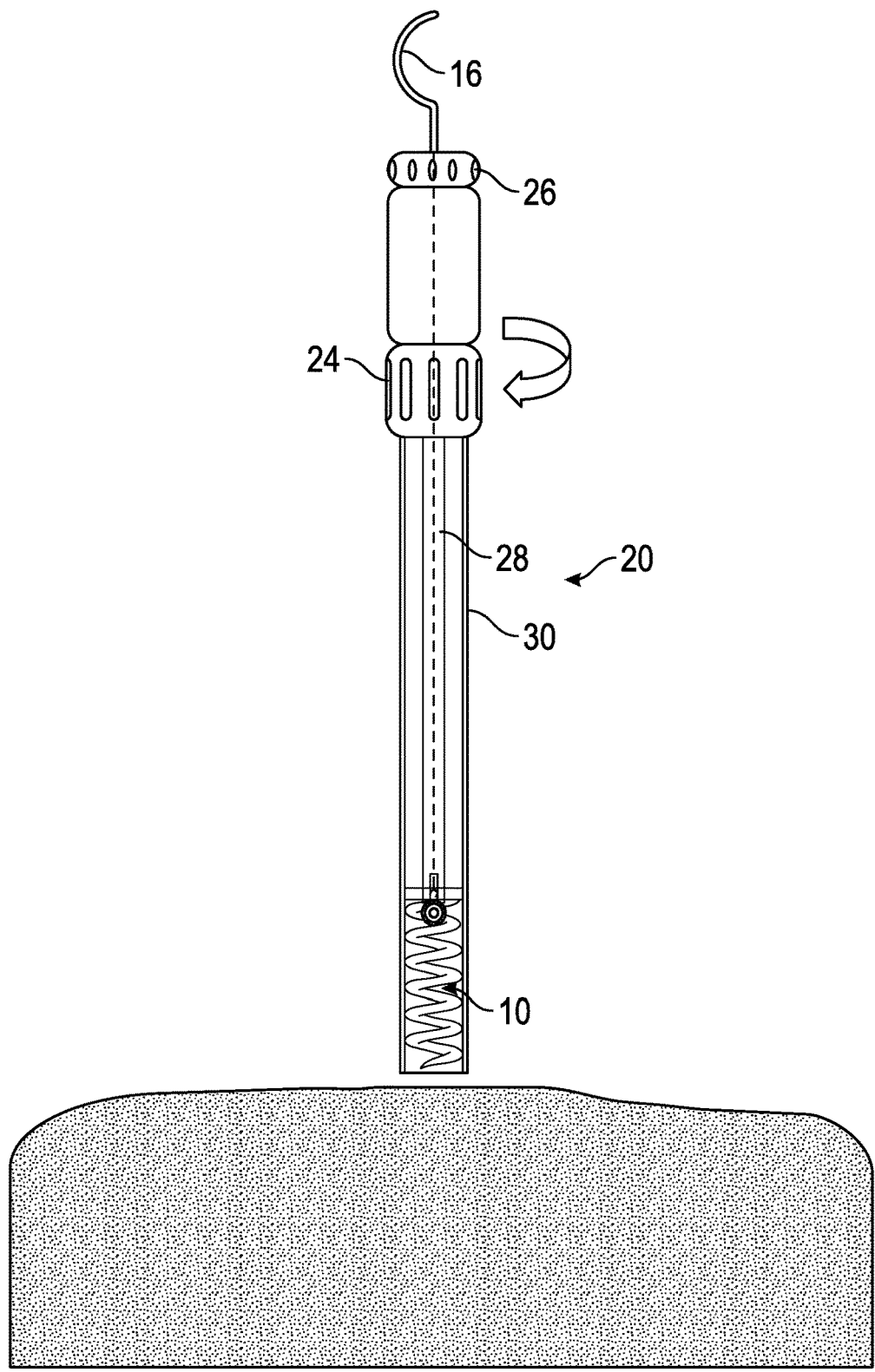
FIG. 28 illustrates a method step in some methods of use of the anchor and a suture of FIG. 25A.

FIG. 28 illustrates the anchor driver 20 at the specific tissue location for anchoring. The distal tip of the anchor driver 20 is placed over the tissue. In some embodiments, the distal tip touches the tissue. The torque knob 24 is rotated in an appropriate direction. The anchor 10 is coupled to the torque shaft 28 such that rotation of the torque knob 24 causes rotation of the anchor 10. The anchor 10 is rotated to engage the anchor 10 with the tissue. Further rotation causes the anchor 10 to travel distally into the tissue. In other embodiments, the anchor 10 is pushed into the tissue. For instance, FIGS. 19A-19B illustrate an embodiment of an anchor that can be pushed into tissue rather than rotated to engage tissue. In some embodiments, the anchor driver 20 includes a pusher (not shown) instead of a torque driver 28. The pusher can cause distal movement of an anchor without rotation.

Figure 29:
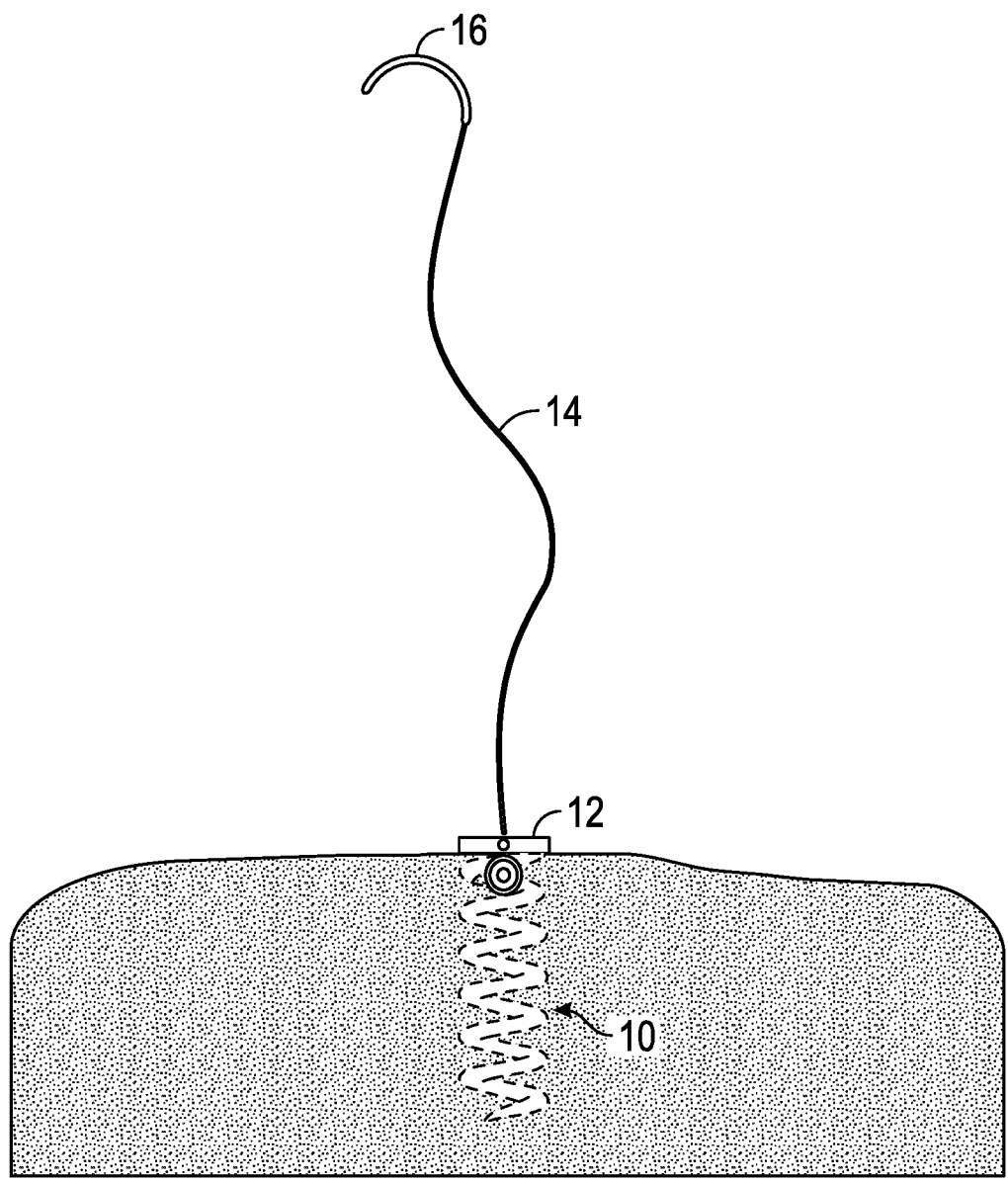
FIG. 29 illustrates a method step in some methods of use of the anchor and a suture of FIG. 25A.

FIG. 29 illustrates the anchor 10 fully deployed within the tissue. The anchor driver 20 is removed. The hub 12 of the anchor 10 can be adjacent to the tissue as shown. The hub 12 of the anchor 10 can be embedded within the tissue. The suture 14 and the needle 16 can extend from the hub 12. The suture 14 can be attached to the anchor 10 by a knot. In some embodiments, the end of the suture 14 is heat formed into the shape of a ball.

Figure 30:
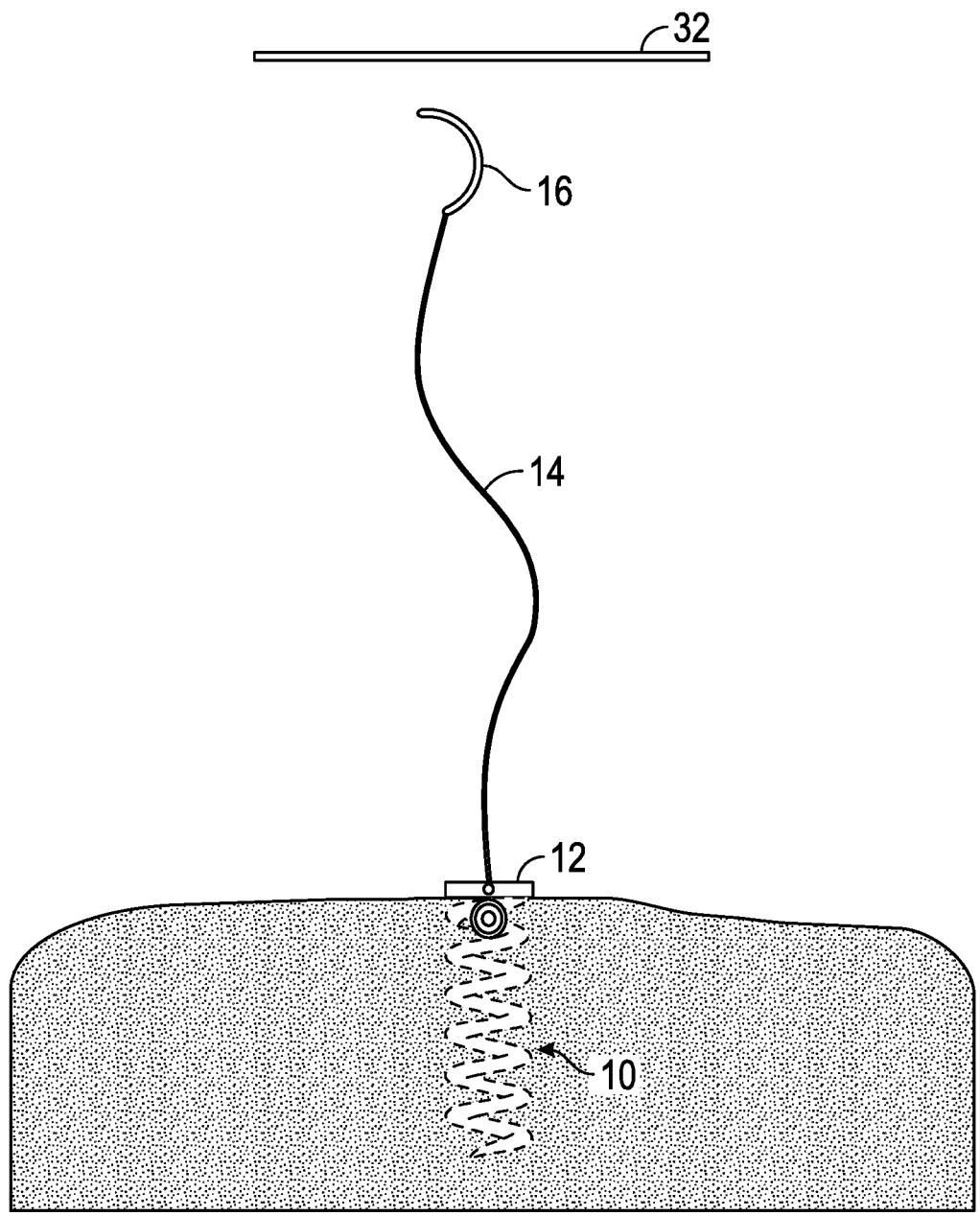
FIG. 30 illustrates a method step in some methods of use of the anchor and a suture of FIG. 25A.
Figure 31:
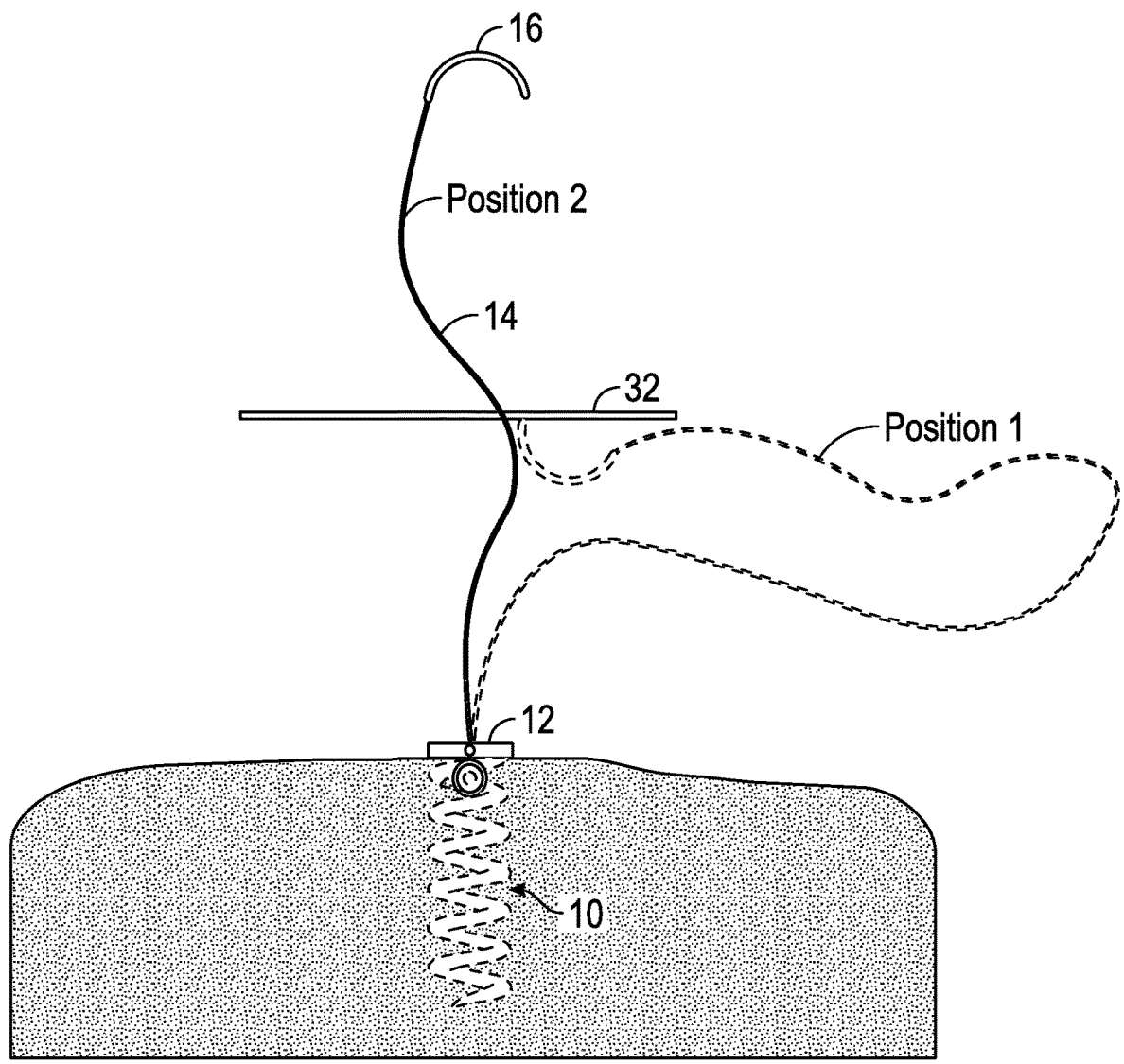
FIG. 31 illustrates a method step in some methods of use of the anchor and a suture of FIG. 25A.

FIG. 30 illustrates that once the anchor 10 is fully deployed into tissue, the needle 16 on the suture 14 can be utilized to attach an implant 32 (illustrated schematically) to the anchor 10. Non-limiting examples of the implant 32 include, for example, a coaptation assistance device, an annuloplasty ring, an artificial valve, cardiac patch, sensor, pacemaker, or other implants. The implant 32 could be a mitral valve ring or artificial mitral or aortic valve in some embodiments. The implant can be any implant described herein. The implant 32 can be lowered toward the needle 16 as shown. The needle 16 can engage the implant 32. In some embodiments, the needle 16 can pass through the implant 32, as shown in FIG. 31. The needle 16 and the suture 14 are initially in position 1. The needle and the suture can pass through the implant to be in position 2. Other suture paths are contemplated. FIG. 31 illustrates the needle 16 being used to engage the suture 14 with the implant 32. The needle 16 and the suture 14 are shown passing through the implant 32.

FIG. 32 illustrates an embodiment of a clip 34. The clip 34 can be considered a knotless suture clip. The clip 34 can include a cable. The cable can be made of nitinol or superelastic nitinol, for example. The cable can include at least two wires or strands 36. In the illustrated embodiment, the cable includes seven strands, but one two or more strands are contemplated. The two strands can be twisted, and heat set to maintain the shape of the cable. In some embodiments, the cable can be hollow to have a central lumen. In some embodiments, the cable can be solid as illustrated. In some embodiments, the cable is comprised of nitinol wires or strands 36 twisted together to form a cable. In some embodiments, the clip 34 can include one, or a pair of end crimps 38 as shown. The end crimp 38 can be in the form of a tube that surrounds the end of the cable.

In some embodiments, the wires or strands 36 may have a rough surface finish to increase the friction between the clip 34 and the suture 14 to improve the locking force, or a smooth surface finish in other embodiments. In some embodiments, the suture 14 can be comprised of materials with a rough surface to increase the friction between the clip 34 and the suture 14 to improve the locking force. In some embodiments, the suture 14 can include barbs to increase the friction between the clip 34 and the suture 14 to improve the locking force.

The clip 34 can serve the same or a similar function as other clips described herein. The clip 34 can allow a user to lock the implant 32 to the tissue without applying knots to the suture 14. The clip 34 therefore, can result in advantageous rapid attachment. In some methods of use, the rapid attachment can be accomplished by inserting the suture 14 through the wires or strands 36 of the cable. The wires or strands 36 of the cable can apply a force on the surface of the suture 14 and lock onto the suture 14, advantageously preventing loosening.

Figure 33:
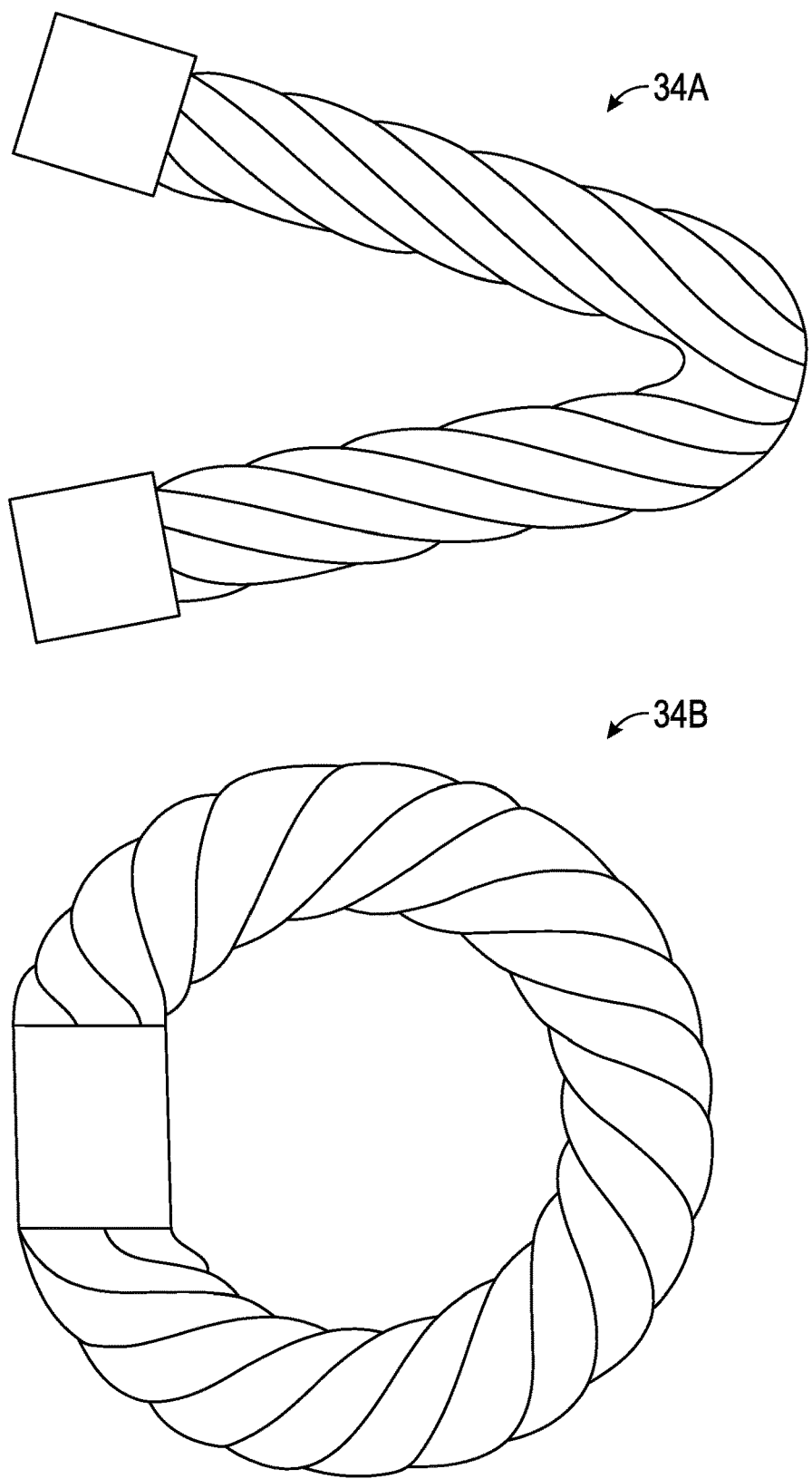
FIG. 33 illustrates embodiments of a clip.

FIG. 33 illustrates embodiments of a clip. The clips 34A, 34B can be considered a knotless suture clip. The clips 34A, 34B can include a cable. The cable can be made of nitinol or superelastic nitinol, for example. The cable can include at least two wires or strands 36. The two strands 36 can be twisted, and heat set to maintain the shape of the cable. In some embodiments, the clips 34A, 34B can include one end crimp 38, or a pair of end crimps 38. The end crimp 38 can be in the form of a tube that surrounds the end of the cable. The cable need not be substantially linear in geometry. For example, the clip 34A can be V shaped as shown in FIG. 33. The clip 34B can be a circular design having a single end crimp 38 as shown in FIG. 33. Depending on the desired clinical result, U shapes, other arcuate shapes including oval shapes, triangular, square, rectangular, or other shapes can also be utilized.

Figure 34:
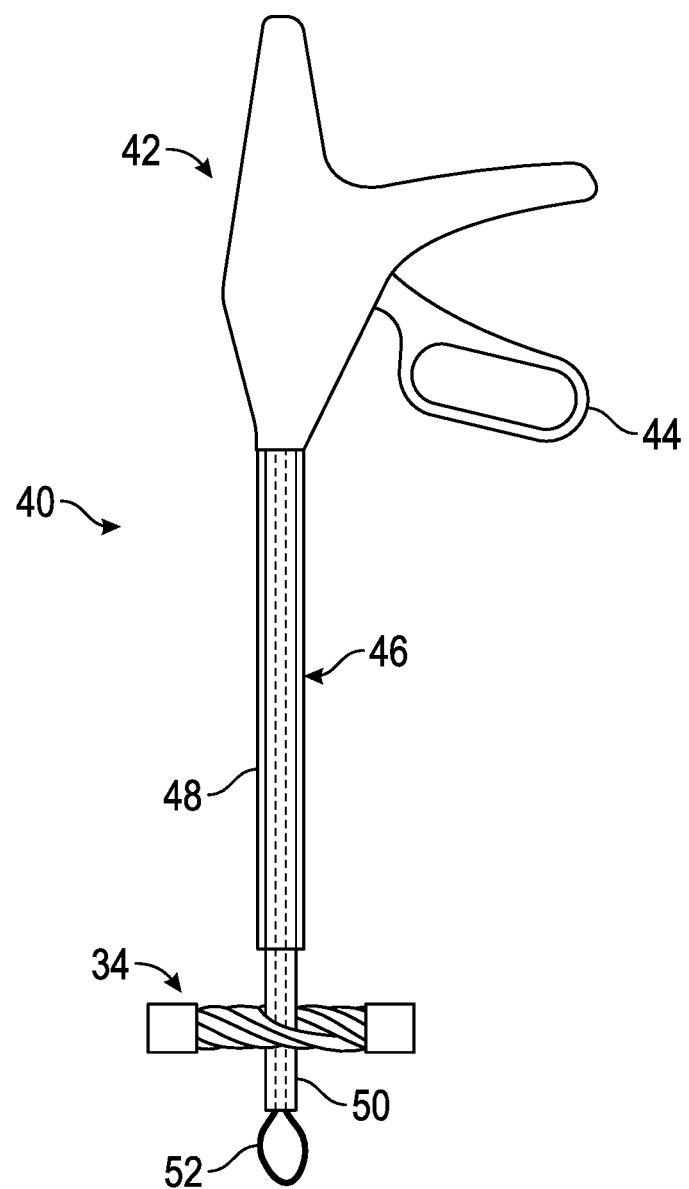
FIG. 34 illustrates an embodiment a tool for use with the suture clip of FIG. 32.

FIG. 34 illustrates an embodiment of a clip driver 40. The clip driver 40 can be used for deploying clips. While clip 34 is shown, other clips described herein can be used with the clip driver 40. The clip driver 40 can include a proximal control handle 42 including a control 44, such as a trigger mechanism as shown. The clip driver 40 can include an elongate body 46. The elongate body 46 can include an outer sleeve 48 and an inner shaft 50. The clip 34 (or other clips described herein) can be removably carried on the inner shaft 50 as shown. In some embodiments, the inner shaft 50 passes through a slot formed by the two strands 36. The inner shaft 50 passes from one side of the clip 34 to the other side of the clip 34. The strands 36 can provide tension to maintain the clip 34 on the inner shaft 50.

The distal end of the clip driver 40 can include a snare 52. The snare 52 can be a lasso. The snare can extend through a lumen of the inner shaft 50. In some embodiments, the inner shaft 50 has a single lumen. In other embodiments, the inner shaft 50 has two lumens, one for each end of the snare 52. The snare 52 can be coupled to the proximal control handle 42. The proximal control handle 42 can retract the snare 52 within the outer sleeve 48. The proximal control handle 42 can retract the snare 52 within the inner shaft 50. The driver can also include an end crimp as illustrated.

Figure 35:
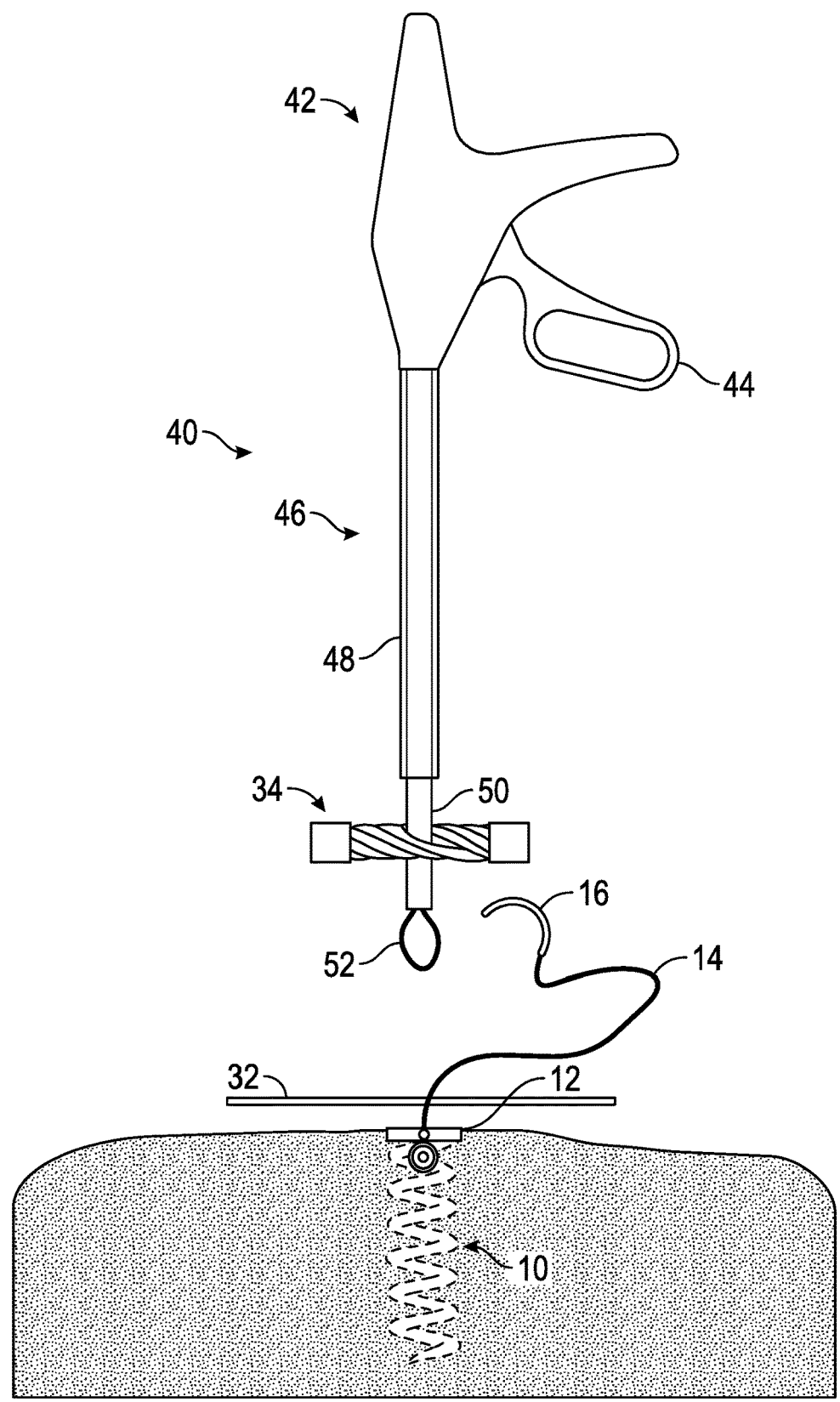
FIG. 35 illustrates a method step in some methods of use of the suture clip of FIG. 32.

FIG. 35 illustrates the clip driver 40 during use. The anchor 10 can be a helical or other anchor as previously described. The anchor 10 can be anchored into tissue. The tissue can be cardiac tissue. The suture 14 can extend from the anchor 10. The implant 32 can be positioned relative to the anchor. The implant 32 can be a cardiac implant or other body implant. The suture 14 and the needle 16 from the anchor 10 can be threaded through the implant 32 as previously described. The driver 40 can be moved toward the implant 32. The driver 40 can be moved in position relative to the suture 14.

Figure 36:
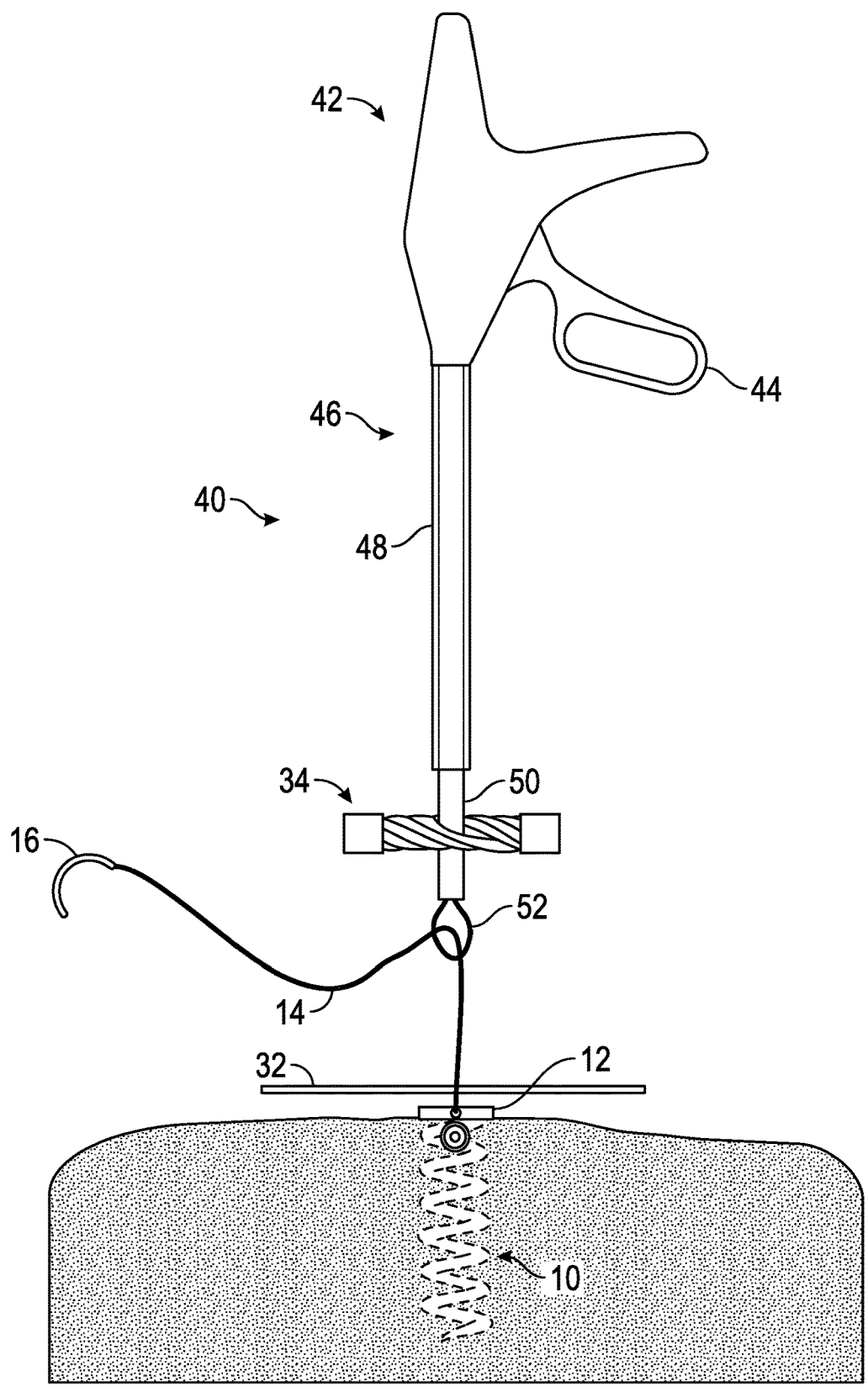
FIG. 36 illustrates a method step in some methods of use of the suture clip of FIG. 32.
Figure 37:
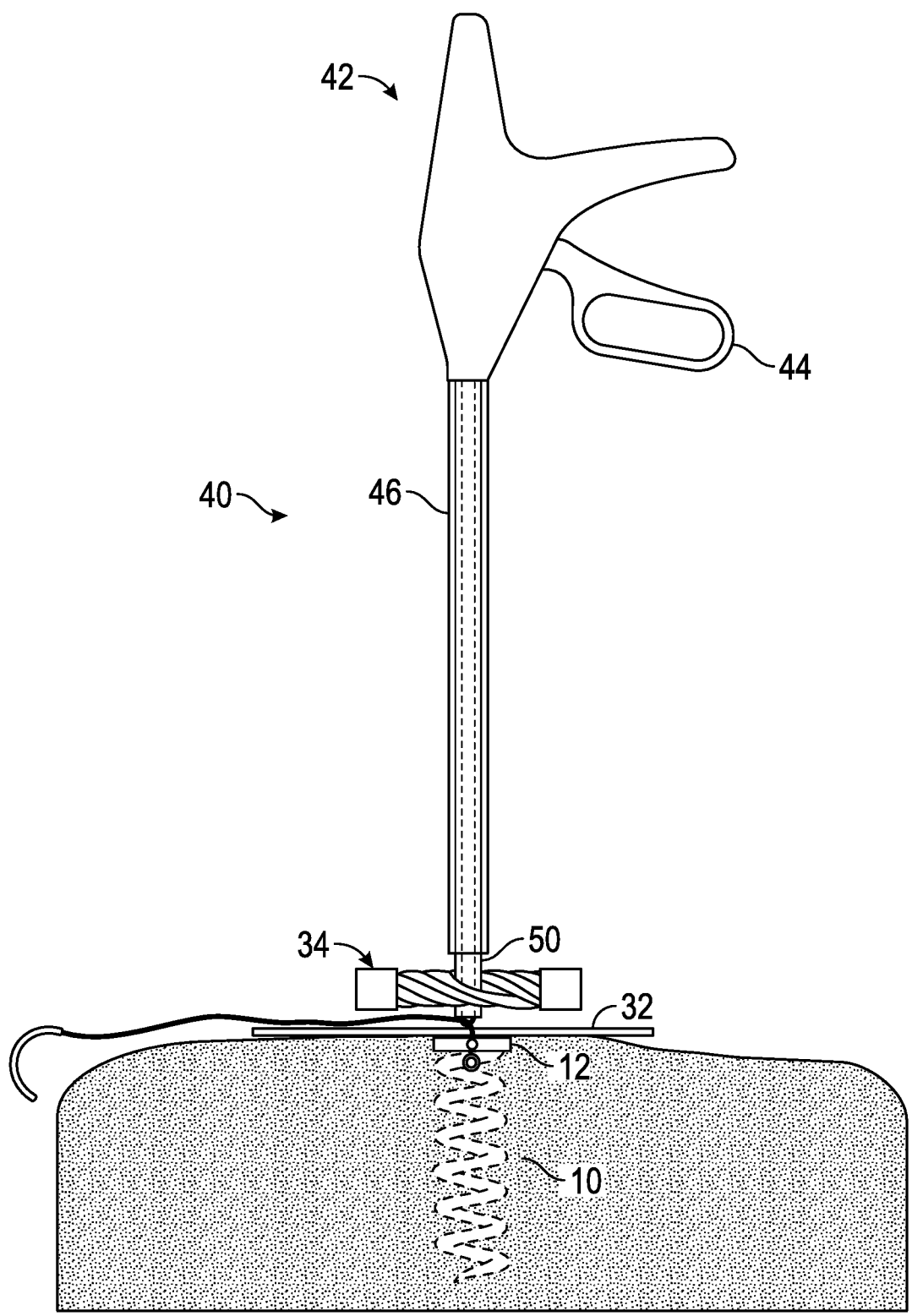
FIG. 37 illustrates a method step in some methods of use of the suture clip of FIG. 32.

FIG. 36 illustrates another method step in some methods, where the suture 14 is threaded through the snare 52. The needle 16 can be threaded through the snare 52. The snare 52 can be looped around the suture 14. The snare 52 can be looped around the needle 16. The suture 14 and/or the needle 16 can be threaded through the snare 52 before the clip 34 is deployed. As illustrated in FIG. 37, the suture 14 is then pulled gently in the direction of the arrow. The clip driver 40 can be moved toward the implant 32. The inner shaft 50 can be positioned adjacent to the implant 32. The clip is placed over the implant 32 before the clip 34 is deployed.

Figure 38:
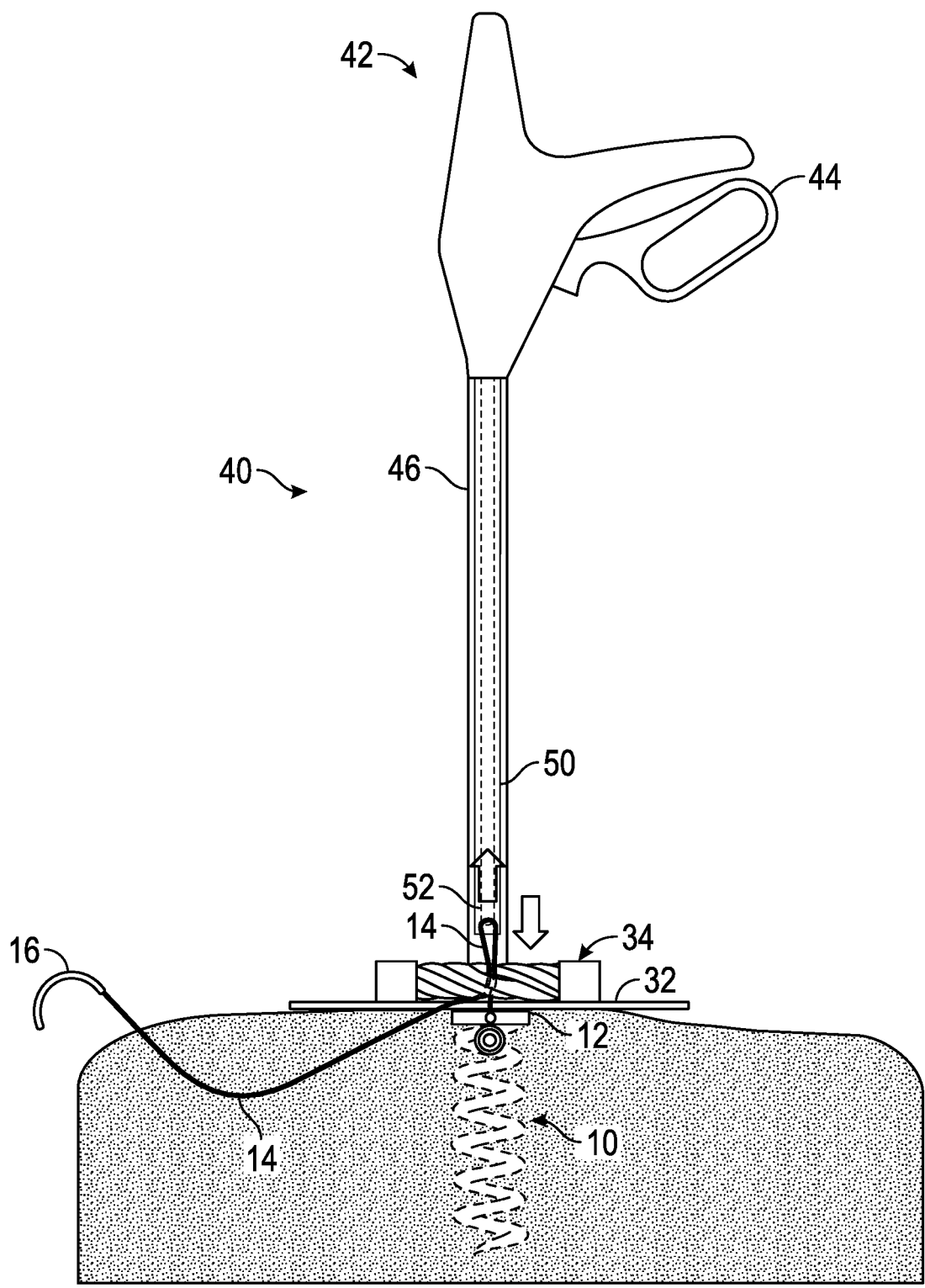
FIG. 38 illustrates a method step in some methods of use of the suture clip of FIG. 32.

By activating the control 44 (e.g., the trigger mechanism) to a first position, the clip 34 can be deployed. FIG. 38 illustrates the step where the control 44 is pulled proximally. This action can retract the inner shaft 50. The inner shaft 50 can be retracted into the outer sleeve 48. The outer sleeve 48 can be moved toward the implant 32. The outer sleeve 48 can be positioned adjacent to the implant.

This action can retract the snare 52 with the inner shaft. The snare 52 can be retracted into the outer sleeve 48. The snare 52 retracts the suture 14 with the snare 52. The snare 52 passes through the clip 34. The snare 52 brings the suture 14 through the clip. After the suture 14 is pulled into the inner shaft 50, the clip 34 is advanced by the outer sleeve 48. The clip 34 is deployed over the suture 34. In some embodiments, separate mechanism or movements retract the inner shaft 50 and the snare 52. In some embodiments, only the inner shaft 50 is retracted. In some embodiments, both the inner shaft 50 and the snare 52 are retracted.

Figure 39:
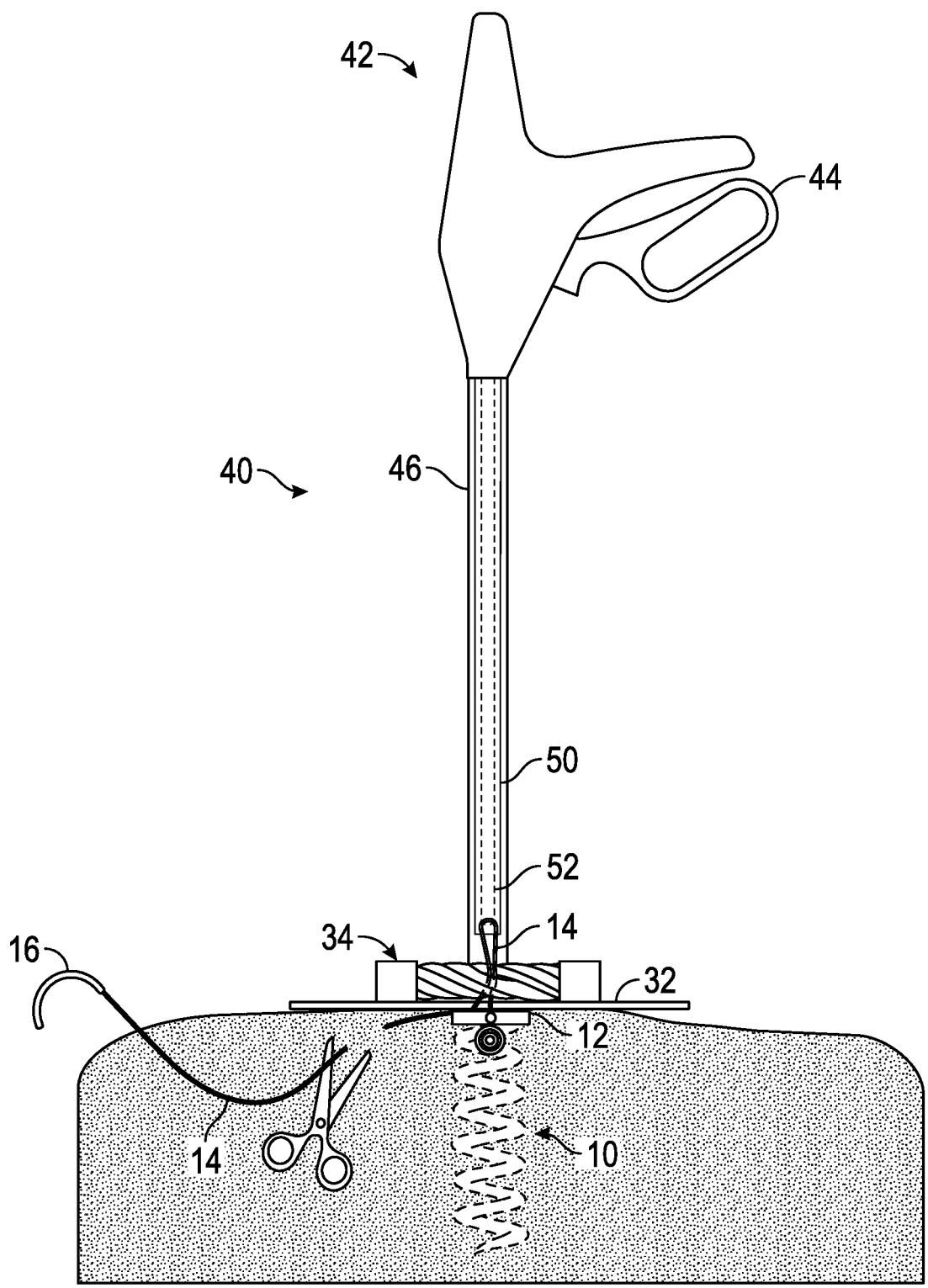
FIG. 39 illustrates a method step in some methods of use of the suture clip of FIG. 32.
Figure 40:
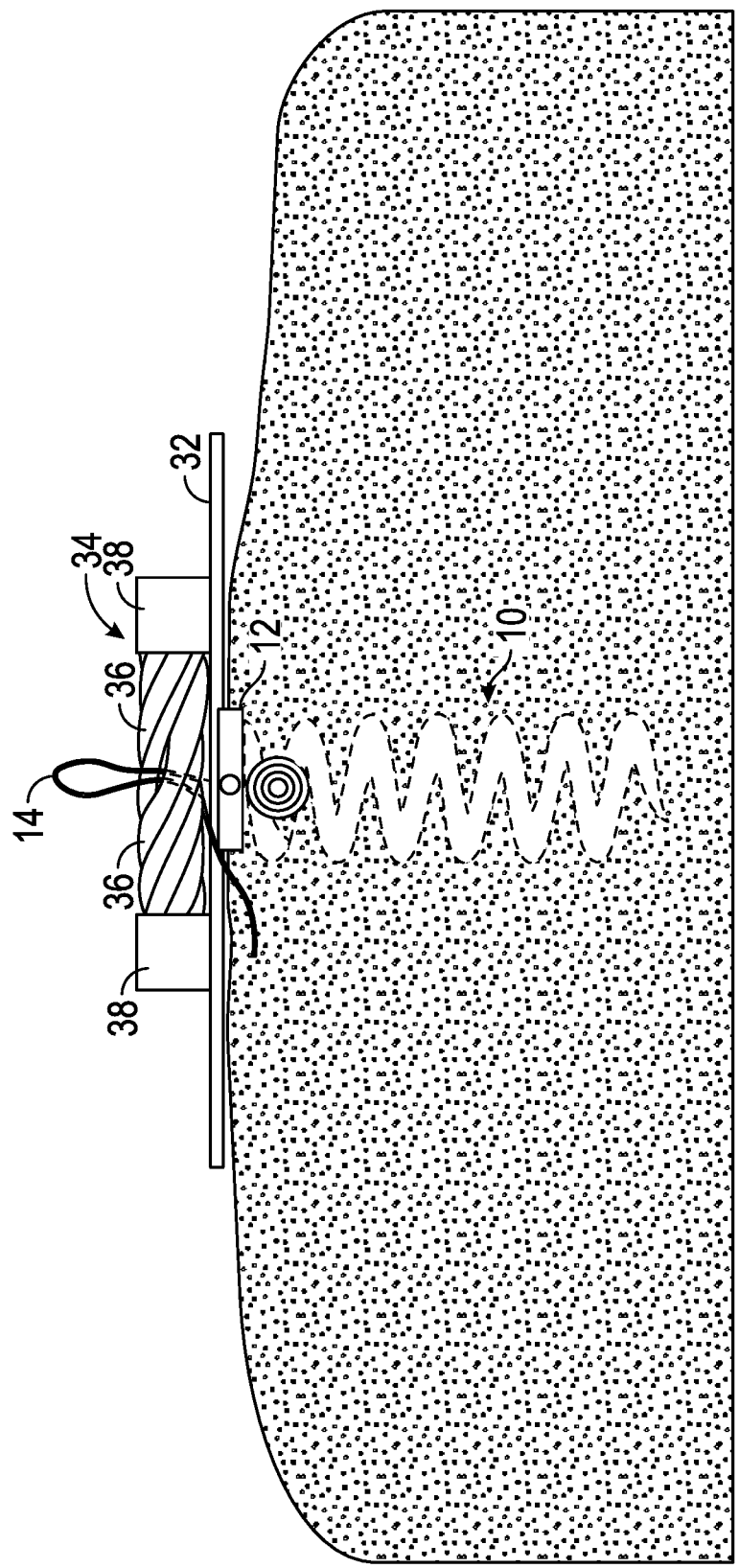
FIG. 40 illustrates a method step in some methods of use of the suture clip of FIG. 32.

As illustrated in FIG. 39, the clip 34 is deployed over the suture 14, tension can be applied to the suture 14 to firmly attach the implant 32 to tissue. Excess suture 14 can then be trimmed. Following deployment of the clip 34 at a desired location, the suture 14 can be cut by activating the control 44 (e.g., the trigger mechanism) to a second position. The second position can be associated with cutting the suture 14. As illustrated in FIG. 40, the clip driver 40 is then removed. In some embodiments, the suture 14 forms a loop through the cable of the clip 34. In some embodiment, the suture 14 forms a suture path from the anchor 10, through the implant 32, through the clip 34, and curving and extending back through the clip 34. Other suture paths are contemplated. The method steps described herein can be repeated several times, including 2, 3, 4, 5, 6, 7, 8, 9, 10, 15, 20, 25, or more times (e.g., in a replacement mitral valve procedure) at selected locations. The clips 34 can be used for anchors 10 on the annulus. The clips 34 can be used for every anchor or selected anchors. The clips 34 can be used to attach the artificial mitral valve to the annulus. Other uses for the clips 34 and anchors 10 are contemplated.

Figure 41:
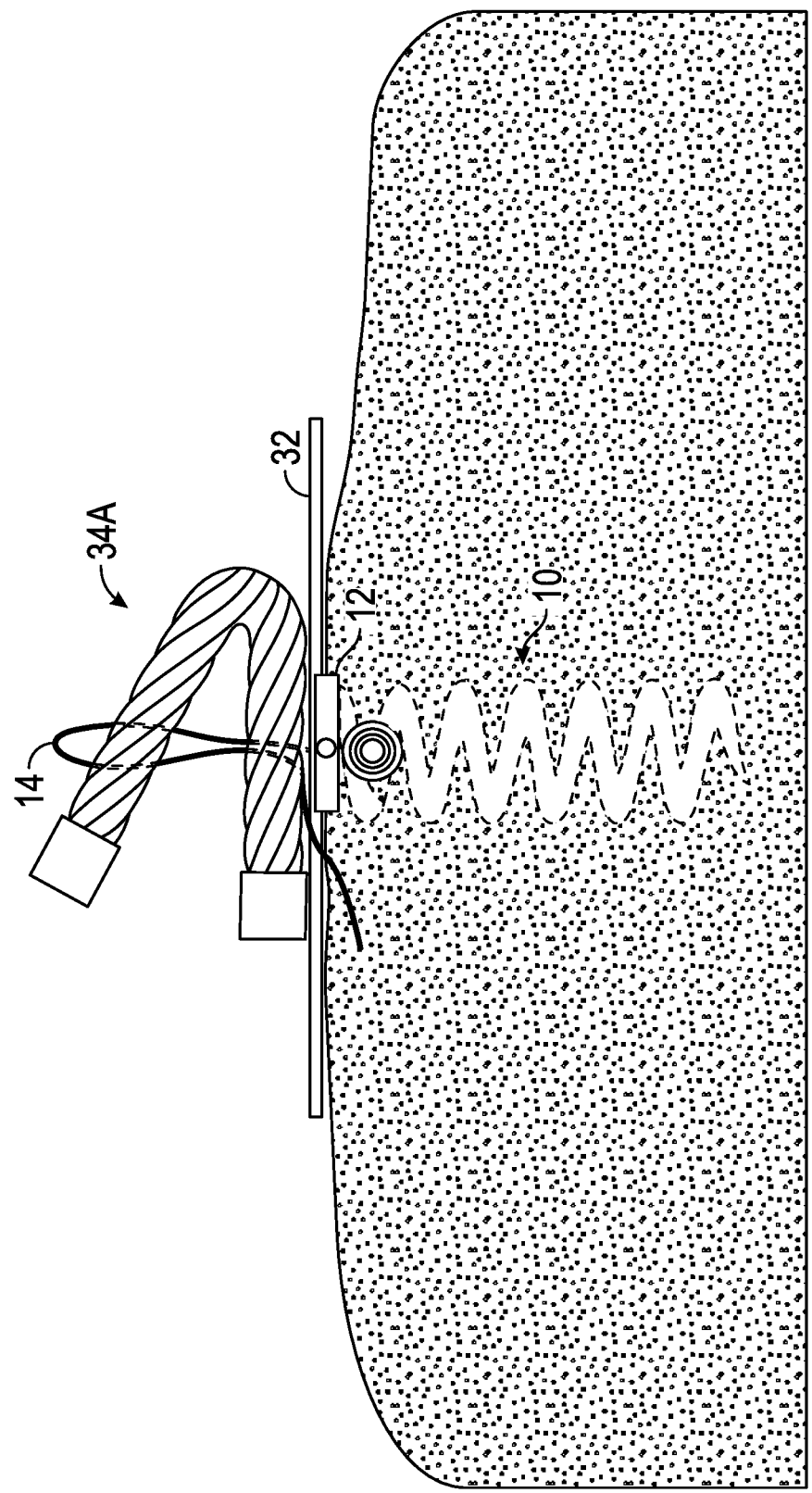
FIG. 41 illustrates a method step in some methods of use of the suture clip of FIG. 33.
Figure 42:
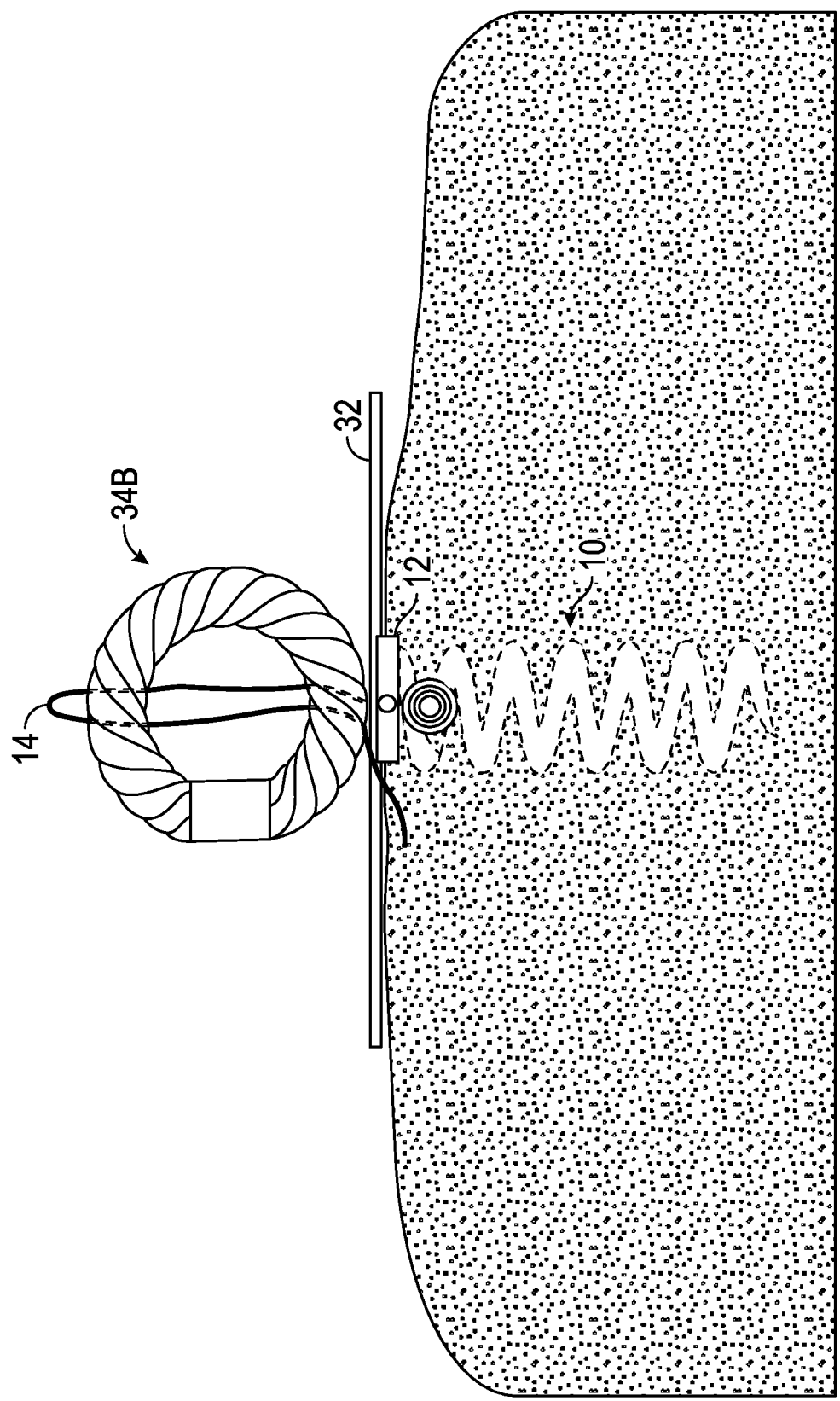
FIG. 42 illustrates a method step in some methods of use of the suture clip of FIG. 33.

FIG. 41 illustrates the clip 34A of FIG. 33 following deployment. FIG. 42 illustrates the clip 34B of FIG. 33 following deployment. The clips 34A, 34B operably connected to the implant 32 and the anchors 10. The clips 34A, 34B are described herein in connection with FIG. 33.

FIGS. 43A-43C illustrates embodiments of an anchor 10. The anchor 10 can have a helical shaft as shown or other geometry configured to engage tissue. The anchor 10 can be made of an appropriate material, such as nitinol for example. The proximal end of the helical shaft can include a central cross pin 18. The central cross pin 18 can be created by laser welding for example. The helical shaft can include any desired number of coil turns or revolutions appropriate for tissue anchoring, such as 1, 2, 3, 4, 5, 6, or more turns. The distal tip of the anchor 10 can have a sharp point grind tip as illustrated. The tip can be the distal most feature of the anchor 10. In some embodiments, the helix can have an outer diameter of between about 3-5 mm, such as about 4.3 mm. The helical shaft can be made of a wire having a diameter, in some embodiments, of between about 0.010" and about 0.030", such as about 0.020" in some cases. The pitch can be, in some embodiments, between about 1 mm and about 2 mm, such as about 1.5 mm in some embodiments. The gap between coils can be, for example, between about 0.5 mm and about 2 mm, such as about 1 mm in some embodiments.

FIGS. 43D-43G illustrate method steps of using a loading suture 54. The loading suture 54 can be used to transfer a slip knot of a tether. The tether can include suture 14 and needle 16. The suture 14 can be 2-0, 3-0, 4-0, or 5-0 suture in some embodiments. The loading suture 54 forms a loop and is passed under the cross pin 18 of the proximal end of the anchor 10. The suture 14 is passed around the loop of the loading suture 54. The suture 14 can have one or more needles 16 attached to the suture 14, as previously described. The loading suture 54 is pulled therefore passing the loop of the suture 14 to the other side of the cross pin 18. The ends of the suture 14 can be passed through the loop of the suture 14, therefore forming a girth hitch knot around the cross pin 18 as shown.

Figure 44A:
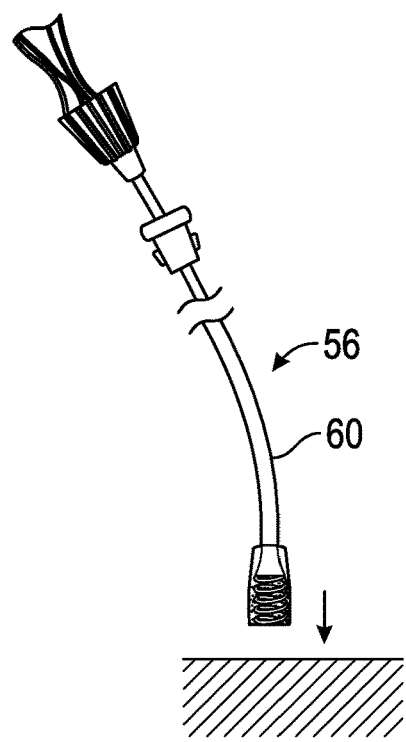
FIGS. 44A-44C illustrates embodiments of an anchor driver.
Figure 44B:
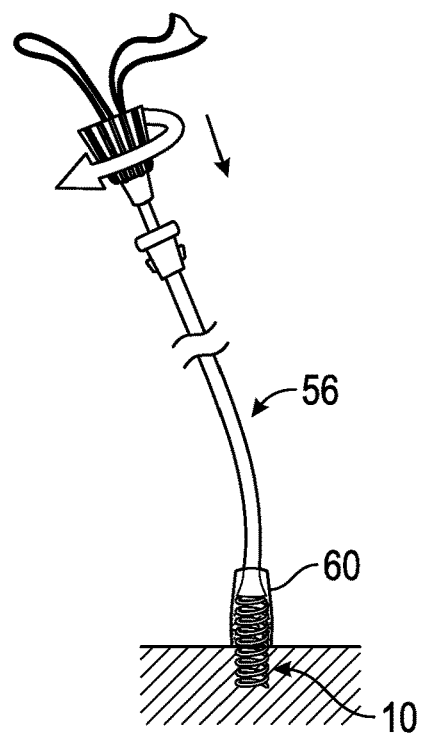
Figure 44C:
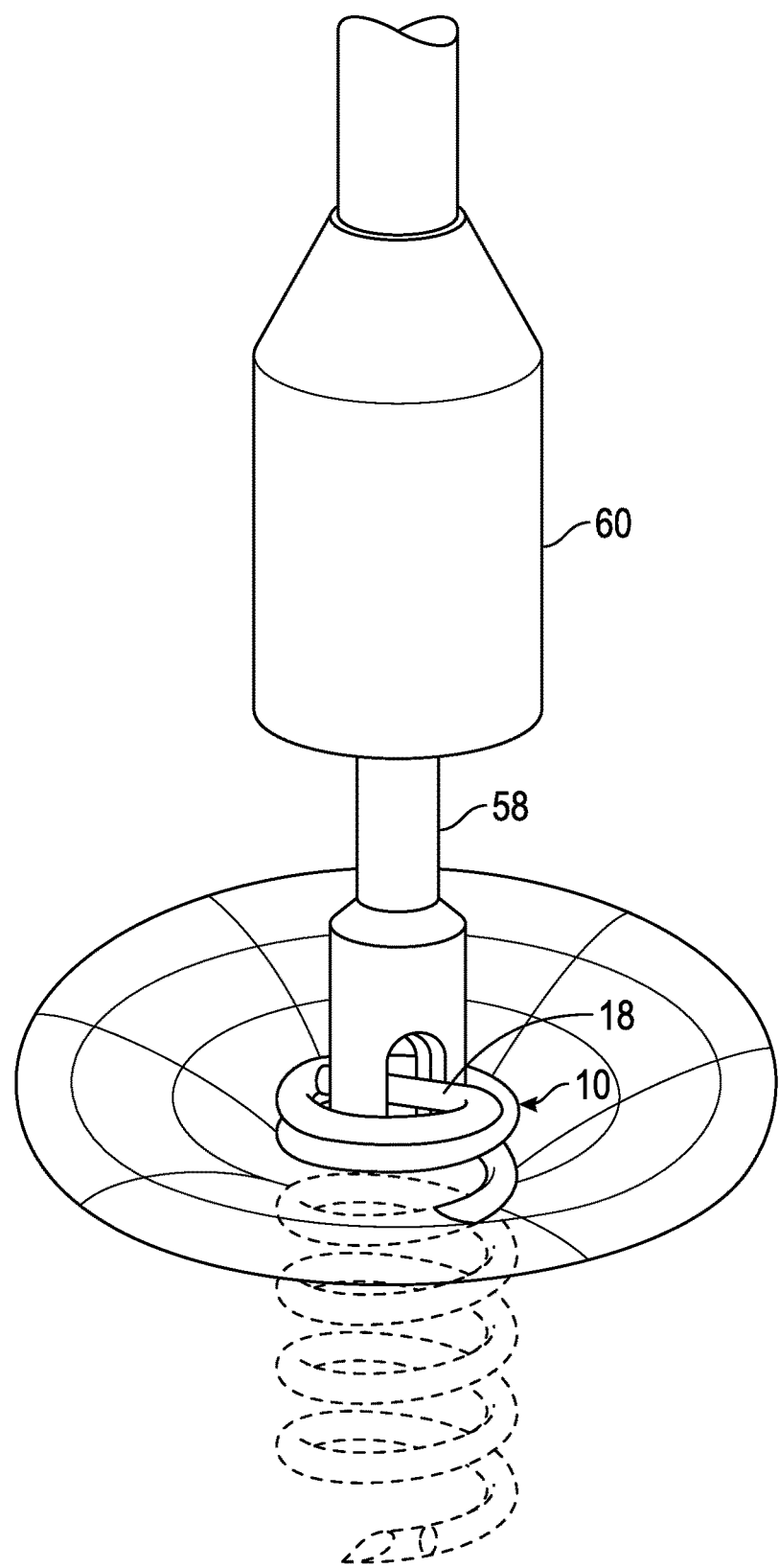

FIGS. 44A-44C illustrates an embodiment of an anchor driver 56. The anchor driver 56 can, for example, include features illustrated and described in connection with FIG. 26-28. The distal tip of the anchor driver 56 can be positioned proximate the tissue. With forward pressure on the anchor 10, the torque shaft control can be rotated in an appropriate direction, such as clockwise, to rotate a torque shaft 58. The anchor 10 is coupled to the torque shaft 58 such that rotation of the toque shaft control causes rotation of the anchor 10. Further rotation of the torque shaft control drives the anchor 10 into the tissue. The anchor driver 56 can include a distal housing 60. The distal housing 60 can be retracted in order to visualize the anchor engagement. If needed, the distal housing 60 can be advanced back over the proximal end of the anchor 10 and additional torque can be applied to further drive and secure the anchor 10 into tissue. Further inspection can be done following the additional torqueing, and repeated as necessary. In some embodiments, the cross pin 18 of the anchor 10 can fit into a cutout at the tip of the torque shaft 58.

The anchor driver 56 can include a Tuohy-Borst or similar leak-resistant valve or adapter. The adapter can be located on the proximal end of a handle of the anchor driver 56. The adapter can secure the suture 14 or loading suture 54 while the anchor 10 is being driven into the tissue. Once satisfied with anchor engagement, the adapter can be undone to loosen the suture 14 or loading suture 54. The anchor driver 56 can be removed. If a loading suture 54 is coupled to the anchor 10, then the method steps described previously can be used. The suture 14 (e.g., 3-0 or 4-0 suture in some embodiments) can be loaded through the loop of the loading suture 54. The suture 14 can be pulled through the anchor cross pin 18 as illustrated and described in connection with FIG. 43. In some methods, the loading suture 54 can be fully retracted to "dock" the cross pin 18 of the anchor 10 into the cutout at the tip of the torque shaft 58. The suture 14 can be secured via the Tuohy-Borst or other adapter.

Figure 45A:
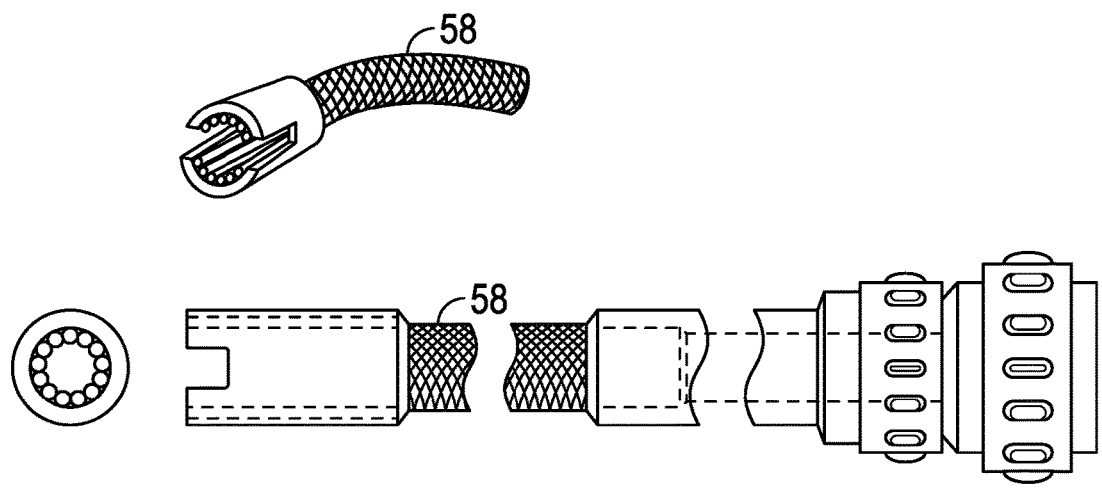
FIGS. 45A-45B illustrates an embodiment of the dimensions of the anchor driver of FIGS. 44A-44C.
Figure 45B:
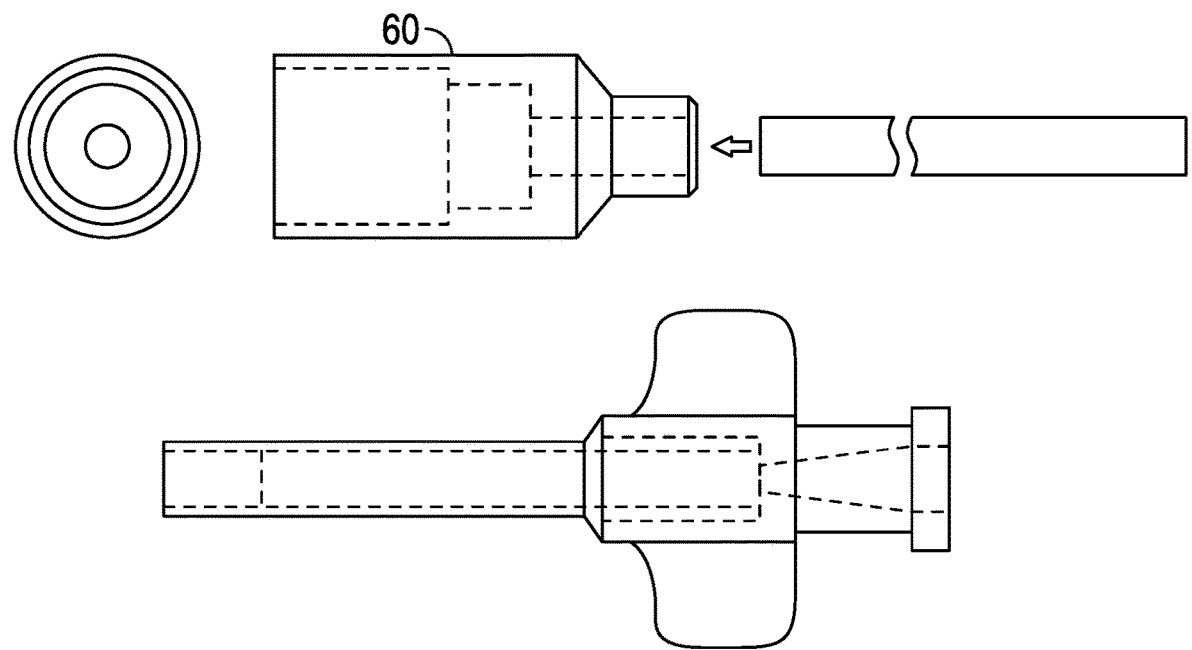
Figure 46A:
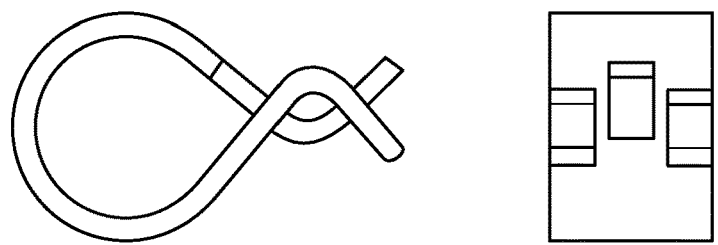
FIGS. 46A-46E illustrates an embodiment of a suture clip.
Figure 46B:
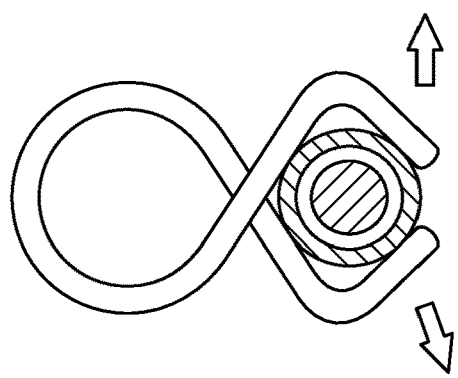
Figure 46C:
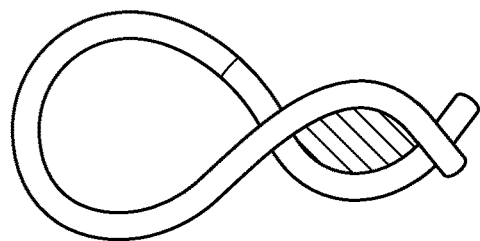
Figure 46D:
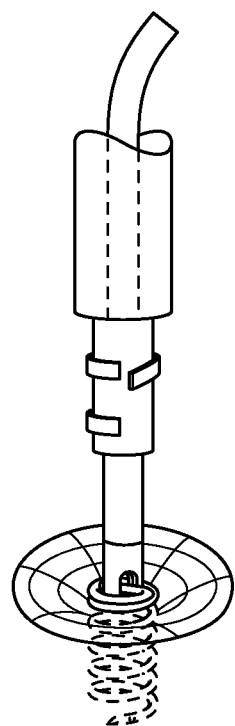
Figure 46E:

FIGS. 45A-45B illustrate non-limiting dimensions for embodiments of the anchor driver 56, including the torque shaft 58. In some embodiments, the dimensions are approximately the dimensions listed. Schematic and cross-sectional views are also shown.

FIGS. 46A-46E illustrate an embodiment of a clip. The clip can be shape-set. The clip can be made of a shape memory material such as nitinol. The clip can include two lever arms, a fulcrum cross-over point, and a loop portion as illustrated. In some methods of use, the clip can be loaded onto a thin-walled hypotube of an inserter. In some methods of use, the clip can be pushed off the hypotube using a pusher tube. The clip can cinch down onto the suture 14, immobilizing the implant 32 against the anchor 10. The clip can have a loaded state in which the hypotube and the suture 14 are at least partially surrounded by the lever arms of the clip. The clip can have a clipped state in which the suture is compressed as the lever arms close in together. Also illustrated is the clip removably attached over the sidewall of the hypotube as part of the delivery system. Distal movement of the pusher can move the clip distally off the hypotube and onto the suture 14. The suture 14 can be attached, such as pre-attached to the anchor 10, such as a helical anchor as previously described. In some embodiments, the implant surface and implant grommet is sown over the tissue. The anchor 10 shown below the tissue in dashed lines. Excess suture can be removed as previously described.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a coaptation assist body proximate the mitral valve" includes "instructing the inserting of a coaptation assist body proximate the mitral valve." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system comprising:
an anchor comprising a proximal end and a distal end, wherein the distal end is configured to be secured to tissue, wherein the anchor comprises a cross pin, wherein the anchor comprises a helical shaft,
a coaptation assistance device comprising a first surface configured to be disposed toward a posterior leaflet of a valve when implanted and a second surface, opposed to the first surface, the second surface configured to be disposed toward an anterior leaflet of the valve when implanted, where the first surface and the second surface are bounded by a first lateral edge, a second lateral edge, an inferior edge, and a superior edge, the coaptation assistance device comprising a support structure comprising a shape memory material configured to maintain the shape and functionality of the coaptation assistance device as the heart contracts and dilates and exerts pressure on the coaptation assistance device, wherein the anchor is configured to secure the coaptation assistance device to an annulus, wherein the coaptation assistance device is configured to directly engage the anterior leaflet for coaptation without reshaping the annulus, wherein the coaptation assistance device provides a new coaptation surface over the posterior leaflet, wherein opposition or engagement of coaptation assistance device and the anterior leaflet against each other provides closure or sealing of the valve,
an anchor driver comprising a distal housing and a torque shaft, wherein the cross pin of the anchor is configured to fit into a cutout at a distal end of the torque shaft, wherein the anchor is disposed within the distal housing during delivery, wherein the anchor is configured to be rotated by the torque shaft relative to the distal housing to secure the anchor into tissue of the annulus, and
a loading suture configured to hold the anchor in position while the anchor is being driven into tissue, wherein the loading suture is releasably secured to the anchor such that the loading suture is configured to slip from the anchor to release the loading suture from the anchor after the anchor is driven into tissue.

2. The system of claim 1, wherein the distal housing comprises a tapered portion.

3. The system of claim 1, wherein the anchor driver is configured to secure the loading suture during delivery.

4. The system of claim 3, wherein the loading suture is configured to be loosened once the anchor is secured.

5. The system of claim 1, wherein the distal end of the anchor comprises a sharpened tip.

6. The system of claim 1, wherein the helical shaft comprises an outer diameter of between about 3-5 mm.

7. The system of claim 1, wherein the helical shaft comprises a wire having a diameter between about 0.010" and about 0.030".

8. The system of claim 1, wherein the helical shaft has a pitch between about 1 mm and about 2 mm.

9. The system of claim 1, wherein the helical shaft has a gap between coils between about 0.5 mm and about 2 mm.

10. A system comprising:
an anchor comprising a proximal end and a distal end, wherein the distal end is configured to engage tissue, wherein the anchor comprises a cross pin and a helical shaft,
a coaptation assistance device comprising a first surface configured to be disposed toward a posterior leaflet when implanted and a second surface configured to be disposed toward an anterior leaflet when implanted, wherein the anchor is configured to secure the coaptation assistance device to an annulus,
an anchor driver comprising a distal housing and a torque shaft, wherein the cross pin of the anchor is configured to fit into a forked end of the torque shaft, wherein the anchor is configured to be delivered to a tissue site within the distal housing, wherein the anchor is configured to be rotated by the torque shaft to engage tissue of the annulus, and
a loading suture engaging the anchor when the anchor is rotated, the loading suture extending through the anchor driver and extending proximally from the anchor driver, wherein the anchor driver is configured to apply tension on the loading suture during delivery of the anchor, wherein tension on the loading suture holds the anchor against the torque shaft during rotation of the anchor.

11. The system of claim 10, wherein the distal housing comprises a tapered portion.

12. The system of claim 10, wherein the distal end of the anchor comprises a sharpened tip.

13. The system of claim 10, wherein the helical shaft comprises an outer diameter of between about 3-5 mm.

14. The system of claim 10, wherein the helical shaft comprises a wire having a diameter between about 0.010" and about 0.030".

15. The system of claim 10, wherein the helical shaft has a pitch between about 1 mm and about 2 mm.

16. The system of claim 10, wherein the helical shaft has a gap between coils between about 0.5 mm and about 2 mm.

17. A system comprising:
a primary anchor comprising a proximal end and a distal end, wherein the distal end is configured to be driven into tissue, wherein the primary anchor comprises a cross pin, wherein the anchor comprises a helical shaft,
a coaptation assistance device comprising a support structure comprising a shape memory material configured to maintain the shape and functionality of the coaptation assistance device, wherein the coaptation assistance device comprises a tubular extension connected to the support structure and extending upward from the support structure, wherein the tubular extension is configured to receive the primary anchor, wherein the primary anchor is configured to secure the coaptation assistance device to an annulus, wherein the coaptation assistance device comprises a superior edge configured to reside within the annulus, an inferior edge configured to extend toward the ventricle, and lateral edges extending between the superior edge and the inferior edge, wherein the lateral edges taper inward from the superior edge to the inferior edge such that the coaptation assistance device is generally triangular, wherein the coaptation assistance device comprising a first surface configured to be overlie a posterior leaflet of a valve when implanted and a second surface, opposed to the first surface, configured to be disposed toward an anterior leaflet of the valve when implanted, where the first surface and the second surface are bounded by the superior edge, the inferior edge, the lateral edges, wherein the coaptation assistance device provides a new coaptation surface over the posterior leaflet, wherein opposition or engagement of coaptation assistance device and the anterior leaflet against each other provides closure or sealing of the valve,
an anchor driver comprising a distal housing and a torque shaft, wherein the cross pin of the primary anchor is configured to fit within a distal end of the torque shaft, wherein the torque shaft and the primary anchor are disposed within the distal housing, wherein the torque shaft and the primary anchor are rotatable relative to the distal housing to drive the primary anchor into tissue, and at least one secondary anchor spaced from the tubular extension and the primary anchor, the one or more secondary anchors having a different configuration than the primary anchor.

18. The system of claim 17, wherein the anchor driver is configured to secure a suture during delivery.

19. The system of claim 17, wherein the helical shaft comprises an outer diameter of between about 3-5 mm.

20. The system of claim 17, wherein the helical shaft comprises a wire having a diameter between about 0.010" and about 0.030".

\* \* \* \* \*